(12) United States Patent
Kitajima et al.

(10) Patent No.: US 9,341,616 B2
(45) Date of Patent: May 17, 2016

(54) SWEET TASTE RECEPTOR CHIMERIC PROTEINS AND USE THEREOF

(71) Applicant: AJINOMOTO CO., INC., Tokyo (JP)

(72) Inventors: Seiji Kitajima, Kanagawa (JP); Yutaka Ishiwatari, Kanagawa (JP)

(73) Assignee: AJINOMOTO CO., INC., Tokyo (JP)

( * ) Notice: Subject to any disclaimer, the term of this patent is extended or adjusted under 35 U.S.C. 154(b) by 0 days.

(21) Appl. No.: 14/666,606

(22) Filed: Mar. 24, 2015

(65) Prior Publication Data
US 2015/0276710 A1   Oct. 1, 2015

(30) Foreign Application Priority Data

Mar. 28, 2014 (JP) ................. 2014-069884

(51) Int. Cl.
| | |
|---|---|
| C07K 14/705 | (2006.01) |
| C07K 19/00 | (2006.01) |
| G01N 33/557 | (2006.01) |
| G01N 33/50 | (2006.01) |
| C07K 14/72 | (2006.01) |

(52) U.S. Cl.
CPC ............ *G01N 33/502* (2013.01); *C07K 14/705* (2013.01); *C07K 14/723* (2013.01); *G01N 2333/705* (2013.01); *G01N 2500/02* (2013.01)

(58) Field of Classification Search
None
See application file for complete search history.

(56) References Cited

U.S. PATENT DOCUMENTS

| | | | |
|---|---|---|---|
| 6,818,747 B2 | 11/2004 | Yao et al. |
| 7,041,457 B2 | 5/2006 | Yao et al. |
| 7,241,880 B2 | 7/2007 | Adler et al. |
| 7,291,485 B2 | 11/2007 | Yao et al. |
| 7,435,552 B2 | 10/2008 | Adler et al. |
| 7,534,577 B2 | 5/2009 | Adler et al. |
| 7,588,916 B2 | 9/2009 | Adler et al. |
| 7,655,422 B2 | 2/2010 | Adler et al. |
| 7,781,181 B2 | 8/2010 | Adler et al. |
| 7,786,263 B2 | 8/2010 | Adler et al. |
| 7,919,236 B2 | 4/2011 | Slack et al. |
| 8,067,539 B2 | 11/2011 | Adler et al. |
| 8,138,322 B2 | 3/2012 | Adler et al. |
| 8,153,774 B2 | 4/2012 | Adler et al. |
| 8,361,729 B2 | 1/2013 | Adler et al. |
| 8,436,143 B2 | 5/2013 | Adler et al. |
| 8,450,457 B2 | 5/2013 | Adler et al. |
| 8,609,362 B2 | 12/2013 | Slack et al. |
| 2002/0128433 A1 | 9/2002 | Yao et al. |
| 2002/0143151 A1 | 10/2002 | Yao et al. |
| 2003/0054448 A1 | 3/2003 | Adler et al. |
| 2003/0232407 A1 | 12/2003 | Zoller et al. |
| 2004/0209286 A1 | 10/2004 | Adler et al. |
| 2005/0032158 A1 | 2/2005 | Adler et al. |
| 2005/0085625 A1 | 4/2005 | Li et al. |
| 2005/0136512 A1 | 6/2005 | Yao et al. |
| 2006/0084117 A1 | 4/2006 | Yao et al. |
| 2006/0275765 A1 | 12/2006 | Slack et al. |
| 2007/0292944 A1 | 12/2007 | Adler et al. |
| 2008/0214784 A1 | 9/2008 | Adler et al. |
| 2008/0220451 A1 | 9/2008 | Adler et al. |
| 2009/0047736 A1 | 2/2009 | Adler et al. |
| 2009/0098579 A1 | 4/2009 | Adler et al. |
| 2009/0275125 A1 | 11/2009 | Adler et al. |
| 2010/0075412 A1 | 3/2010 | Adler et al. |
| 2011/0177545 A1 | 7/2011 | Slack et al. |
| 2012/0164664 A1 | 6/2012 | Adler et al. |
| 2012/0171674 A1 | 7/2012 | Adler et al. |
| 2012/0271035 A1 | 10/2012 | Adler et al. |
| 2013/0345092 A1 | 12/2013 | Adler et al. |
| 2014/0030380 A1 | 1/2014 | Kitajima et al. |

FOREIGN PATENT DOCUMENTS

| | | |
|---|---|---|
| EP | 2520647 A1 | 11/2012 |
| WO | WO00/06593 A1 | 2/2000 |
| WO | WO2005/015158 A2 | 2/2005 |
| WO | WO2007/121599 A1 | 11/2007 |

OTHER PUBLICATIONS

Zhang et al., Molecular mechanism for the umami taste synergism, Dec. 30, 2008, PNAS 105(52):20930-20934.*
Toda et al., Two Distinct Determinants of Ligand Specificity in T1R1/T1R3 (the Umami Taste Receptor), Dec. 27, 2013, The Journal of Biological Chemistry, vol. 288, No. 52, pp. 36863-36877.*
Shimizu et al., Distinct Human and Mouse Membrane Trafficking Systems for Sweet Taste Receptors T1r2 and T1, Jul. 2014, PLOS ONE 9(7):e10425, 11 pages.*
Koizumi et al., Taste-modifying sweet protein, neoculin, is received at human T1R3 amino terminal domain, Jun. 29, 2007, Biochemical and Biophysical Research Communications 358(2): 585-589.*
Nelson, G., et al., "Mammalian Sweet Taste Receptors," Cell 2001;106:381-390.
Nelson, G., et al., "An amino-acid taste receptor," Nature 2002;416:199-202.
Ohta, K., et al., "The cysteine-rich domain of human T1R3 is necessary for the interaction between human T1R2-T1R3 sweet receptors and a sweet-tasting proteins, thaumatin," Biochem. Biophys. Res. Comm. 2011;406:435-438.
Jiang, P., et al., "The Cysteine-rich Region of T1R3 Determines Responses to Intensely Sweet Proteins," J. Biol. Chem. 2004;279(43):45068-45075.
Hoon, M. A., et al., "Functional expression of the taste specific G-protein, α-gustducin," Biochem. Journal 1995;309:629-636.
Extended European Search Report for European Patent App. No. 15161102.7 (Jul. 7, 2015).

* cited by examiner

*Primary Examiner* — John Ulm
(74) *Attorney, Agent, or Firm* — Shelly Guest Cermak; Cermak Nakajima & McGowan LLP

(57) ABSTRACT

A sweet taste substance or a sweet taste-regulating substance is detected by contacting a test substance with a cell that expresses a chimeric protein of human T1R2 and mouse T1R2, and/or a chimeric protein of human T1R3 and mouse T1R3, and may further express a G protein α subunit, and by detecting an interaction between the chimeric proteins and the test substance.

17 Claims, 10 Drawing Sheets

US 9,341,616 B2

SWEET TASTE RECEPTOR CHIMERIC PROTEINS AND USE THEREOF

This application claims priority under 35 U.S.C. §119 to Japanese Patent Application No. 2014-069884, filed Mar. 28, 2014, the entirety of which is incorporated by reference herein. Also, the Sequence Listing filed electronically herewith is hereby incorporated by reference (File name: 2015-03-24T_Seq_List; File size: 219 KB; Date recorded: Mar. 24, 2015).

BACKGROUND OF THE INVENTION

1. Field of the Invention

The present invention relates to sweet taste receptor chimeric proteins, chimeric G proteins, and their uses. A cell that expresses a sweet taste receptor protein or G protein is useful to detect a sweet-tasting substance or a sweet taste-regulating substance, and so forth.

2. Brief Description of the Related Art

The T1R family of receptors are known to be involved in taste perception, and have also been identified as seven-transmembrane G protein-coupled receptors (GPCR). It is known that the T1R family includes three kinds of subunits, T1R1, T1R2, and T1R3, and the heterodimer of T1R2 and T1R3 functions as a sweet taste receptor (Nelson, G. et al., Cell, 106:381-390 (2001) for mouse, and WO2002/064631 for human). It is also known that the heterodimer of T1R1 and T1R3 functions as an umami taste receptor (Nelson G. et al., Nature, 416:199-202 (2002) for mouse, and WO2002/064631). Furthermore, a method has been proposed to detect a ligand compound that specifically binds to a sweet taste receptor, such as a sweet-tasting substance or a substance that regulates sweet taste, by using a cell that expresses a sweet taste receptor and the G protein α subunit ($G_\alpha$) (WO2002/064631).

Furthermore, a chimeric protein of human T1R2 and mouse T1R2 (Ohta, K., et al., Biochem. Biophys. Res. Commun., 406:435-438 (2011)), and a chimeric protein of human T1R3 and mouse T1R3 (ibid. and Jiang and P. et al., J. Biol. Chem., 279(43):45068-45075 (2004)) have been produced, and a cysteine-rich domain (CRD) has been identified as being necessary for perception of sweet taste. However, it is not known whether or not a chimeric T1R2 or chimeric T1R3 having a specific structure is more suitable for detection of a sweet taste receptor-activating substance as compared to naturally occurring T1R2 and T1R3.

As taste-specific G proteins, the $G_q$ family, gustducin, transducin, and so forth, are known, and gustducin and transducin have been reported to have the same function when interacting with a receptor (Hoon, M. A. et al., Biochem. J., 309:629-636 (1995)).

As for $G_\alpha$, a chimeric protein consisting of a mutant $G_{\alpha q}$ protein in which the C-terminal part is replaced with 44 amino acid residues of the C-terminus of the mouse transducin α subunit has been reported (WO2002/036622). It is disclosed that this chimeric protein shows increased promiscuity (WO2002/036622). In addition, this reference describes that the amino acid residues of the C-terminus of the transducin α subunit to be used should be 44 residues or less.

Furthermore, a chimeric G protein consisting of the rat $G_{\alpha 15}$ protein in which the last 44 amino acid residues are replaced with the last 44 amino acid residues of the gustducin α subunit has been reported (WO2004/055048).

SUMMARY OF THE INVENTION

The present invention provides a chimeric T1R2 and chimeric T1R3 useful for detecting a sweet taste substance or a sweet taste-regulating substance, as well as a technique for detecting a sweet taste substance or sweet taste-regulating substance.

The present invention describes chimeric T1R2 and chimeric T1R3 receptors having a specific structure that are useful, at least, for detecting a sweet taste substance or a sweet taste-regulating substance.

An aspect of the present invention is to provide a method for detecting a sweet taste substance or a sweet taste-regulating substance comprising the steps of:

contacting a test substance with a cell that expresses a T1R2 protein and a T1R3 protein, and detecting an interaction of the T1R2 protein and/or T1R3 protein and the test substance, wherein a) the T1R2 protein is selected from the group consisting of:

a1) a chimeric T1R2 protein comprising the region of positions 1 to 470 of the human T1R2 protein, and the region of positions 475 to 843 of the mouse T1R2 protein, which are fused in this order, a2) a chimeric T1R2 protein comprising the region of positions 1 to 480 of the human T1R2 protein, and the region of positions 485 to 843 of the mouse T1R2 protein, which are fused in this order, a3) a chimeric T1R2 protein comprising the region of positions 1 to 489 of the human T1R2 protein, and the region of positions 494 to 843 of the mouse T1R2 protein, which are fused in this order, and/or wherein b) the T1R3 protein is selected from the group consisting of:

b1) a chimeric T1R3 protein comprising the region of positions 1 to 63 of the human T1R3 protein, the region of positions 64 to 539 of the mouse T1R3 protein, and the region of positions 535 to 852 of the human T1R3 protein, which are fused in this order, b2) a chimeric T1R3 protein comprising the region of positions 1 to 63 of the mouse T1R3 protein, the region of positions 64 to 162 of the human T1R3 protein, the region of positions 163 to 539 of the mouse T1R3 protein, and the region of positions 535 to 852 of the human T1R3 protein, which are fused in this order, b3) a chimeric T1R3 protein comprising the region of positions 1 to 162 of the mouse T1R3 protein, the region of positions 163 to 242 of the human T1R3 protein, the region of positions 243 to 539 of the mouse T1R3 protein, and the region of positions 535 to 852 of the human T1R3 protein, which are fused in this order.

It is a further aspect of the present invention to provide the method as described above, wherein said contacting comprises also contacting a sweet taste substance to the cell that expresses a T1R2 protein and a T1R3 protein.

It is a further aspect of the present invention to provide the method as described above, wherein at least the T1R2 protein is chimeric.

It is a further aspect of the present invention to provide the method as described above, wherein both the T1R2 protein and the T1R3 protein are chimeric.

It is a further aspect of the present invention to provide the method as described above, wherein the chimeric T1R2 protein has an amino acid sequence having a SEQ ID NO: selected from the group consisting of SEQ ID NOS: 18, 22, and 14.

It is a further aspect of the present invention to provide the method as described above, wherein the chimeric T1R3 protein has an amino acid sequence having a SEQ ID NO: selected from the group consisting of SEQ ID NOS: 30, 37, and 41.

It is a further aspect of the present invention to provide the method as described above, wherein the cell further expresses a G protein α subunit.

It is a further aspect of the present invention to provide the method as described above, wherein the G protein α subunit is a chimeric $G_\alpha$ protein comprising the region of positions 1 to 327 of the rat $G_{\alpha 15}$, and the region of positions 307 to 354 of the transducin α subunit, which are fused in this order, and the methionine residue at position 312, and the valine residue at position 316 of the transducin α subunit are replaced with a leucine residue, and an aspartic acid residue, respectively.

It is a further aspect of the present invention to provide the method as described above, wherein the chimeric $G_\alpha$ protein has the amino acid sequence of SEQ ID NO: 50.

It is a further aspect of the present invention to provide the method as described above, wherein said detecting is conducted by measuring the change of intracellular free calcium ion concentration.

It is a further aspect of the present invention to provide the method as described above, wherein the cell is an animal cell, an insect cell, or a yeast cell.

It is a further aspect of the present invention to provide the method as described above, wherein the cell is a cultured cell isolated from human.

It is a further aspect of the present invention to provide the method as described above, wherein the cell is an HEK cell.

It is a further aspect of the present invention to provide a cell that expresses a T1R2 protein and a T1R3 protein, wherein a) the T1R2 protein is selected from the group consisting of:

a1) a chimeric T1R2 protein comprising the region of positions 1 to 470 of the human T1R2 protein, and the region of positions 475 to 843 of the mouse T1R2 protein, which are fused in this order, a2) a chimeric T1R2 protein comprising the region of positions 1 to 480 of the human T1R2 protein, and the region of positions 485 to 843 of the mouse T1R2 protein, which are fused in this order, a3) a chimeric T1R2 protein comprising the region of positions 1 to 489 of the human T1R2 protein, and the region of positions 494 to 843 of the mouse T1R2 protein, which are fused in this order, and/or b) the T1R3 protein is selected from the group consisting of:

b1) a chimeric T1R3 protein comprising the region of positions 1 to 63 of the human T1R3 protein, the region of positions 64 to 539 of the mouse T1R3 protein, and the region of positions 535 to 852 of the human T1R3 protein, which are fused in this order, b2) a chimeric T1R3 protein comprising the region of positions 1 to 63 of the mouse T1R3 protein, the region of positions 64 to 162 of the human T1R3 protein, the region of positions 163 to 539 of the mouse T1R3 protein, and the region of positions 535 to 852 of the human T1R3 protein, which are fused in this order, b3) a chimeric T1R3 protein comprising the region of positions 1 to 162 of the mouse T1R3 protein, the region of positions 163 to 242 of the human T1R3 protein, the region of positions 243 to 539 of the mouse T1R3 protein, and the region of positions 535 to 852 of the human T1R3 protein, which are fused in this order.

It is a further aspect of the present invention to provide the cell as described above, which further expresses a G protein α subunit.

It is a further aspect of the present invention to provide a chimeric T1R2 protein selected from the group consisting of:

a1) a chimeric T1R2 protein comprising the region of positions 1 to 470 of the human T1R2 protein, and the region of positions 475 to 843 of the mouse T1R2 protein, which are fused in this order, a2) a chimeric T1R2 protein comprising the region of positions 1 to 480 of the human T1R2 protein, and the region of positions 485 to 843 of the mouse T1R2 protein, which are fused in this order, and a3) a chimeric T1R2 protein comprising the region of positions 1 to 489 of the human T1R2 protein, and the region of positions 494 to 843 of the mouse T1R2 protein, which are fused in this order.

It is a further aspect of the present invention to provide a chimeric T1R3 protein selected from the following chimeric T1R3 proteins of b1) to b3):

b1) a chimeric T1R3 protein comprising the region of positions 1 to 63 of the human T1R3 protein, the region of positions 64 to 539 of the mouse T1R3 protein, and the region of positions 535 to 852 of the human T1R3 protein, which are fused in this order, b2) a chimeric T1R3 protein comprising the region of positions 1 to 63 of the mouse T1R3 protein, the region of positions 64 to 162 of the human T1R3 protein, the region of positions 163 to 539 of the mouse T1R3 protein, and the region of positions 535 to 852 of the human T1R3 protein, which are fused in this order, and b3) a chimeric T1R3 protein comprising the region of positions 1 to 162 of the mouse T1R3 protein, the region of positions 163 to 242 of the human T1R3 protein, the region of positions 243 to 539 of the mouse T1R3 protein, and the region of positions 535 to 852 of the human T1R3 protein, which are fused in this order.

It is a further aspect of the present invention to provide a polynucleotide coding for the chimeric T1R2 protein as described above.

It is a further aspect of the present invention to provide a polynucleotide coding for the chimeric T1R3 protein as described above.

Chimeric T1R2 proteins, chimeric T1R3 proteins, chimeric G proteins, and a cell that expresses any of these are useful for detecting a sweet taste substance or a sweet taste-regulating substance. With these chimeric proteins and cells as described herein, a sweet taste substance and a sweet taste-regulating substance can be detected at a higher sensitivity as compared to naturally occurring T1R2, T1R3, and cells that express them.

DESCRIPTION OF THE PREFERRED EMBODIMENTS

Figure 1:
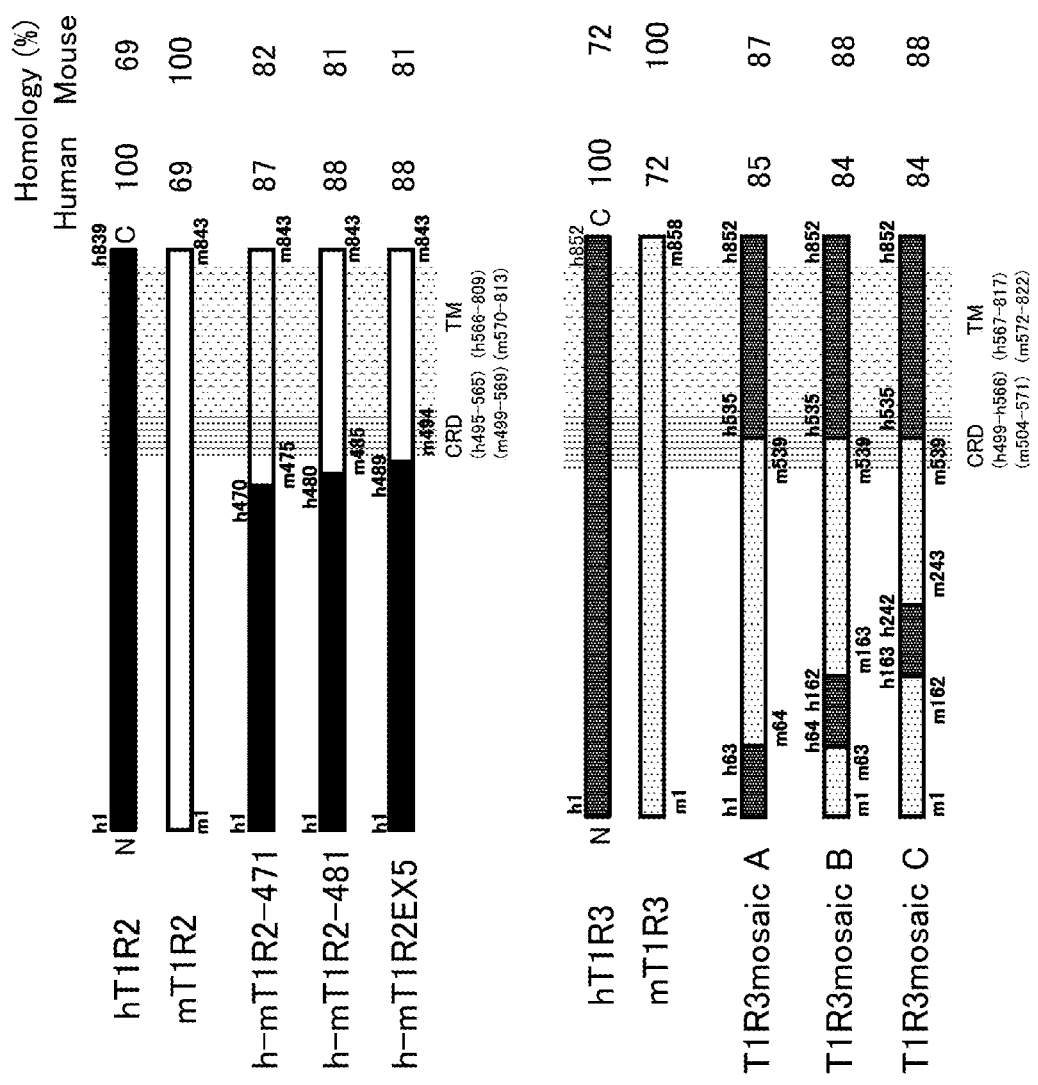
FIG. 1 shows the positions of the regions of chimeric T1R2 and chimeric T1R3 in the human T1R2 (GenBank accession No. NP_689418), mouse T1R2 (GenBank accession No. NP_114079), human T1R3 (GenBank accession No. NP_689414), and mouse T1R3 (GenBank accession No. NP_114078), from which the regions are derived, and homologies of the chimeric T1R2 and chimeric T1R3 to hT1R2, mT1R2, hT1R3, and mT1R3.

The method as described herein is a method for detecting a sweet taste substance or a sweet taste-regulating substance that includes the steps of contacting a test substance with a cell that expresses a T1R2 protein and a T1R3 protein, and detecting an interaction of the T1R2 protein and/or T1R3 protein and the test substance.

In the method, at least one of the T1R2 protein and the T1R3 protein is a chimeric T1R2 protein (henceforth also referred to as "chimeric T1R2") or chimeric T1R3 protein (henceforth also referred to as "chimeric T1R3") having a specific structure. Both the T1R2 and T1R3 proteins can be chimeric proteins.

The chimeric T1R2 is one of the following proteins:

a1) a chimeric T1R2 having the region of positions 1 to 470 of the human T1R2 protein, and the region of positions 475 to 843 of the mouse T1R2 protein, which are fused in this order, a2) a chimeric T1R2 having the region of positions 1 to 480 of the human T1R2 protein, and the region of positions 485 to 843 of the mouse T1R2 protein, which are fused in this order, a3) a chimeric T1R2 having the region of positions 1 to 489 of the human T1R2 protein, and the region of positions 494 to 843 of the mouse T1R2 protein, which are fused in this order.

The chimeric T1R3 is one of the following proteins:

b1) a chimeric T1R3 having the region of positions 1 to 63 of the human T1R3 protein, the region of positions 64 to 539 of the mouse T1R3 protein, and the region of positions 535 to 852 of the human T1R3 protein, which are fused in this order, b2) a chimeric T1R3 having the region of positions 1 to 63 of the mouse T1R3 protein, the region of positions 64 to 162 of the human T1R3 protein, the region of positions 163 to 539 of the mouse T1R3 protein, and the region of positions 535 to 852 of the human T1R3 protein, which are fused in this order, b3) a chimeric T1R3 having the region of positions 1 to 162 of the mouse T1R3 protein, the region of positions 163 to 242 of the human T1R3 protein, the region of positions 243 to 539 of the mouse T1R3 protein, and the region of positions 535 to 852 of the human T1R3 protein, which are fused in this order.

The structures of the chimeric T1R2 and chimeric T1R3, and the regions of human T1R2, mouse T1R2, human T1R3, and mouse T1R3, which are the origins of the chimeric proteins, are shown in FIG. 1. In FIG. 1, CRD represents a cysteine-rich domain, and TM represents a transmembrane domain. The characters and numbers described above or under the chimeric proteins represent the origins and positions from the N-terminus. For example, "h1" for T1R2 represents the first amino acid residue from the N-terminus of the human T1R2.

<1> T1R2 protein and T1R3 protein

T1R2 and T1R3 from which the chimeric T1R2 protein and chimeric T1R3 protein are derived are explained below. When the term "T1R2" and "T1R3" are used without the indication of chimeric, they represent T1R2 and T1R3 that are not chimeric proteins.

Examples of human T1R2 include a protein having the amino acid sequence of SEQ ID NO: 52. Examples of the nucleotide sequence coding for human T1R2 include the nucleotide sequence of SEQ ID NO: 51.

Examples of mouse T1R2 include a protein having the amino acid sequence of SEQ ID NO: 54. Examples of the nucleotide sequence coding for mouse T1R2 include the nucleotide sequence of SEQ ID NO: 53.

Examples of human T1R3 include a protein having the amino acid sequence of SEQ ID NO: 56. Examples of the nucleotide sequence coding for human T1R3 include the nucleotide sequence of SEQ ID NO: 55.

Examples of mouse T1R3 include a protein having the amino acid sequence of SEQ ID NO: 58. Examples of the nucleotide sequence coding for mouse T1R3 include the nucleotide sequence of SEQ ID NO: 57.

T1R2 and T1R3 can be a protein having one of the aforementioned amino acid sequences including substitution, deletion, insertion, or addition of one or several amino acid residues at one or several positions, so long the function of a sweet taste receptor is maintained. Although the number meant by the term "one or several" can differ depending on types of amino acid residues and positions of the same in the conformations of the proteins, it specifically means a number of, for example, 1 to 50, 1 to 40, or 1 to 30, 1 to 20, 1 to 10, 1 to 5, or 1 to 3.

The aforementioned substitution, deletion, insertion, or addition of one or several amino acid residues is a conservative mutation that maintains normal function of the protein. Typical examples of the conservative mutation are conservative substitutions. The conservative substitution is a mutation wherein substitution takes place mutually among Phe, Trp, and Tyr, if the substitution site is an aromatic amino acid; among Leu, Ile and Val, if it is a hydrophobic amino acid; between Gln and Asn, if it is a polar amino acid; among Lys, Arg and His, if it is a basic amino acid; between Asp and Glu, if it is an acidic amino acid; and between Ser and Thr, if it is an amino acid having a hydroxyl group. Examples of substitutions considered conservative substitutions include, specifically, substitution of Ser or Thr for Ala, substitution of Gln, His or Lys for Arg, substitution of Glu, Gln, Lys, His or Asp for Asn, substitution of Asn, Glu or Gln for Asp, substitution of Ser or Ala for Cys, substitution of Asn, Glu, Lys, His, Asp or Arg for Gln, substitution of Gly, Asn, Gln, Lys or Asp for Glu, substitution of Pro for Gly, substitution of Asn, Lys, Gln, Arg or Tyr for His, substitution of Leu, Met, Val or Phe for Ile, substitution of Ile, Met, Val or Phe for Leu, substitution of Asn, Glu, Gln, His or Arg for Lys, substitution of Ile, Leu, Val or Phe for Met, substitution of Trp, Tyr, Met, Ile or Leu for Phe, substitution of Thr or Ala for Ser, substitution of Ser or Ala for Thr, substitution of Phe or Tyr for Trp, substitution of His, Phe or Trp for Tyr, and substitution of Met, Ile or Leu for Val. Furthermore, such substitution, deletion, insertion, addition, inversion, or the like of amino acid residues as described above includes a naturally occurring mutation due to an individual difference or difference of species of an organism from which the protein is derived (mutant or variant).

Furthermore, T1R2 and T1R3 may be a protein showing a homology of 80% or more, 90% or more, 95% or more, 97% or more, 99% or more, to the total amino acid sequence of any of the amino acid sequences described above, so long as the protein maintains the original function. In this specification, "homology" can mean "identity".

Furthermore, T1R2 and T1R3 can be a protein encoded by a DNA that is able to hybridize with a probe that can be prepared from any of the nucleotide sequences coding for T1R2 or T1R3 described above, for example, a sequence complementary to the whole or a part of such a nucleotide sequence under stringent conditions, so long as the encoded T1R2 and T1R3 can constitute a sweet taste receptor. Such a probe can be prepared by, for example, PCR using oligonucleotides prepared on the basis of such a nucleotide sequence as described above as primers and a DNA fragment containing such a nucleotide sequence as described above as the template. The "stringent conditions" refer to conditions under which a so-called specific hybrid is formed, and a non-specific hybrid is not formed. Examples of the stringent conditions include conditions under which highly homologous DNAs hybridize to each other, for example, DNAs not less than 80% homologous, less than 90% homologous, not less than 95% homologous, not less than 97% homologous, not less than 99% homologous, hybridize to each other, and DNAs less homologous than the above do not hybridize to each other, and conditions of washing once, or 2 or 3 times, at a salt concentration and temperature corresponding to those used for washing in typical Southern hybridization, i.e., 1×SSC, 0.1% SDS at 60° C., 0.1×SSC, 0.1% SDS at 60° C., or 0.1×SSC, 0.1% SDS at 68° C. When a DNA fragment having a length of about 300 bp is used as the probe, the washing conditions of the hybridization can be, for example, 50° C., 2×SSC and 0.1% SDS.

The above descriptions concerning the conservative mutation, and so forth are similarly applied to the G protein α subunit to be described later.

<2> Sweet Taste Receptor Chimeric Protein

The chimeric T1R2 and the chimeric T1R3 have any one of the structures of a1 to a3 described above, and any one of the structures of b1 to b3 described above, respectively.

The positions of the regions or amino acid residues of the chimeric T1R2 originating in the human T1R2 and the mouse T1R2, or the positions of the regions or amino acid residues of the chimeric T1R3 originating in the human T1R3 and the mouse T1R3 do not necessarily mean the absolute positions from the N-terminus in the amino acid sequences of the proteins, and mean relative positions with respect to the amino acid sequences shown as SEQ ID NO: 52, 54, 56, and 58. For example, if one amino acid residue of the human T1R2 having the amino acid sequence of SEQ ID NO: 52 is deleted at a position on the N-terminal side with respect to a position n, this position "n" becomes position "n−1" from the N-terminus. However, even in such a case, the amino acid residue of this position is regarded as the amino acid residue of the position "n". Position of amino acid residue can be determined on the basis of alignment of amino acid sequence of an objective T1R2 and the amino acid sequence of SEQ ID NO: 52. The same shall apply to the mouse T1R2, human T1R3, mouse T1R3, and the G protein α subunit to be described later.

Such alignment can be performed by using known gene analysis software. Specific examples of such software include DNASIS produced by Hitachi Solutions, GENETYX produced by Genetyx, and so forth (Elizabeth C. Tyler et al., Computers and Biomedical Research, 24(1), 72-96, 1991; Barton G. J. et al., Journal of Molecular Biology, 198 (2), 327-37, 1987).

Examples of the chimeric T1R2 of a1 described above include a protein having the amino acid sequence of SEQ ID NO: 18. Examples of the nucleotide sequence coding for the chimeric T1R2 of this type include the nucleotide sequence of SEQ ID NO: 17.

Examples of the chimeric T1R2 of a2 described above include a protein having the amino acid sequence of SEQ ID NO: 22. Examples of the nucleotide sequence coding for the chimeric T1R2 of this type include the nucleotide sequence of SEQ ID NO: 21.

Examples of the chimeric T1R2 of a3 described above include a protein having the amino acid sequence of SEQ ID NO: 14. Examples of the nucleotide sequence coding for the chimeric T1R2 of this type include the nucleotide sequence of SEQ ID NO: 13.

Examples of the chimeric T1R3 of b1 described above include a protein having the amino acid sequence of SEQ ID NO: 30. Examples of the nucleotide sequence coding for the chimeric T1R3 of this type include the nucleotide sequence of SEQ ID???? Examples of the chimeric T1R3 of b2 described above include a protein having the amino acid sequence of SEQ ID NO: 37. Examples of the nucleotide sequence coding for the chimeric T1R3 of this type include the nucleotide sequence of SEQ ID NO: 36.

Examples of the chimeric T1R3 of b3 described above include a protein having the amino acid sequence of SEQ ID NO: 41. Examples of the nucleotide sequence coding for the chimeric T1R3 of this type include the nucleotide sequence of SEQ ID NO: 40.

The nucleotide sequences coding for the chimeric T1R2 and chimeric T1R3 can be a nucleotide sequence in which an arbitrary original codon is replaced with an equivalent codon. For example, the nucleotide sequence coding for the chimeric T1R2 and chimeric T1R3 can be modified so that it has optimal codons according to the codon usage of the host.

A polynucleotide coding for the chimeric T1R2 can be prepared by ligating polynucleotides coding for the human T1R2 and mouse T1R2, so that the resulting polynucleotide codes for a protein having any one of the structures of a1 to a3 described above. A polynucleotide coding for the chimeric T1R3 can be prepared by ligating polynucleotides coding for the human T1R3 and mouse T1R3, so that the resulting polynucleotide codes for a protein having any one of the structures of b1 to b3 described above. A DNA coding for such a chimeric protein can be prepared by, for example, ligating fragments prepared by PCR using a marketed kit (for example, GENEART Seamless Cloning and Assembly Kit (A13288, Invitrogen, Life Technologies).

If a polynucleotide coding for a chimeric T1R2 is expressed in an appropriate host, the chimeric T1R2 can be obtained. If a polynucleotide coding for a chimeric T1R3 is expressed in an appropriate host, the chimeric T1R3 can be obtained.

<2> Cell that Expresses Chimeric T1R2 and/or Chimeric T1R3

A cell that expresses a chimeric T1R2 and/or a chimeric T1R3 can be used for detection of a sweet taste substance or a sweet taste-regulating substance. That is, it is considered that a cell that expresses a chimeric T1R2 and/or a chimeric T1R3 can constitute a sweet taste receptor.

Although it is sufficient that at least one of T1R2 and T1R3 expressed by the cell is a chimeric protein, it is preferred that both are chimeric proteins.

A cell that expresses T1R2 and T1R3, at least one of which is the aforementioned chimeric T1R2 or chimeric T1R3 (also simply referred to as "cell that expresses a chimeric protein"), can be obtained by introducing polynucleotide(s) coding for the chimeric protein(s) into an appropriate host cell in an expressible form. For example, by introducing a linear DNA coding for a chimeric protein or a vector containing a sequence coding for a chimeric protein into a host cell, the chimeric protein can be expressed. The expressible form can be obtained by, for example, introducing sequences required for transcription and translation at a position upstream of a sequence coding for the chimeric protein so that the chimeric protein can be produced on the basis of the information of the DNA. Furthermore, a cell that expresses a chimeric protein can also be obtained by injecting a cRNA coding for the chimeric protein into a host cell. In this case, the cRNA contains sequences required for translation on the 5' end side. Examples of the sequences required for transcription include expression control sequences such as promoter and enhancer. Furthermore, a transcription terminator sequence can also be contained. Examples of the sequences required for translation also include ribosome-binding site. Furthermore, for example, processing information sites such as RNA splicing site, and polyadenylation site can also be contained, if needed. Examples of promoter include promoters originating in immunoglobulin gene, SV40, adenovirus, bovine papilloma virus, cytomegalovirus, and so forth. Non-chimeric T1R2 or T1R3 can also be expressed in the same manner as that used for the chimeric proteins.

As the cell into which a polynucleotide coding for a chimeric protein is introduced, animal cells including those of mammals such as human and amphibians such as frog, insect cells, and yeast cells are preferred, and human cells and animal cells are particularly preferred. For example, fractions in which taste cells are concentrated, isolated taste cells, tissues isolated from an organ selected from tongue epithelium, suprarenal gland, pineal body, thyroid, melanocyte, and kidney, and so forth can also be used. Specific examples of cells considered to be a cell in which a functional chimeric protein can be transiently expressed by introducing a recombinant vector that expresses a polynucleotide coding for the chimeric protein include *Xenopus* oocyte, Chinese hamster ovary cell (CHO), human embryonic kidney (HEK) cell, Sf-9 insect cell, and so forth. The present invention also provides a cell introduced with a polynucleotide coding for such a chimeric protein as described above in an expressible form. As the cell, oocyte or taste cell is preferred, and taste cell is especially preferred for use in detection (including screening) of a sweet taste substance or a sweet taste-regulating substance.

T1R2 and T1R3 (at least one of them is a chimeric protein) can be each introduced into a cell by using separate vectors, or they can be introduced into a cell by using a single vector containing a polynucleotide coding for them.

As the method for introducing a polynucleotide coding for a chimeric protein into a host cell, known methods can be used. Techniques required for such operations as introduction of a polynucleotide into a cell are described in Sambrook, J., Fritsch, E. F., and Maniatis, T., "Molecular Cloning A Laboratory Manual, Second Edition", Cold Spring Harbor Laboratory Press (1989), and so forth.

Such a cell that expresses a chimeric protein as described above can further express the G protein α subunit. T1R2 and T1R3 constitute GPCR (G protein-coupled receptor), and transmit a signal generated upon receiving a sweet taste substance via the G protein. Therefore, if the cell that expresses a chimeric protein also expresses a G protein, reception of a sweet taste substance can be detected by detecting signaling via the G protein.

The G protein consists of $G_\alpha$ subunit (α subunit) and $G_{\beta\gamma}$ subunits, and for the aforementioned purpose, it is sufficient that at least the $G_\alpha$ subunit is expressed. The $G_{\beta\gamma}$ subunits can also be expressed together with the $G_\alpha$ subunit. The $G_\alpha$ subunit is not particularly limited so long as it can couple with T1R2 and T1R3, and examples of the $G_\alpha$ subunit include $G_{\alpha 15}/G_{\alpha 16}$ (referred to as $G_{\alpha 15}$ for rat, and referred to as $G_{\alpha 16}$ for human). Furthermore, the $G_\alpha$ subunit can be a chimeric protein derived from different kinds of G protein α subunits, or a modified version of such a chimeric protein.

Specific examples of the chimeric $G_\alpha$ protein include a chimeric protein of the rat $G_{\alpha 15}$ and the transducin α subunit. More specifically, there can be mentioned a chimeric $G_\alpha$ protein having the region of the positions 1 to 327 of the rat $G_{\alpha 15}$ and the region of positions 307 to 354 of the transducin α subunit, which are fused in this order, wherein, in the region of the positions 307 to 354 of the transducin α subunit, the methionine residue at the position 312 is replaced with a leucine residue, and the valine residue at the position 316 is replaced with the aspartic acid residue.

Examples of such a chimeric $G_\alpha$ protein include a protein having the amino acid sequence of SEQ ID NO: 50. Examples of the nucleotide sequence coding for such a chimeric $G_\alpha$ protein include the nucleotide sequence of SEQ ID NO: 49.

The nucleotide sequence coding for the rat $G_{\alpha 15}$ is shown as SEQ ID NO: 59, and the amino acid sequence encoded by this nucleotide sequence is shown as SEQ ID NO: 60. Furthermore, the nucleotide sequence coding for the rat transducin α subunit is shown as SEQ ID NO: 61, and the amino acid sequence encoded by this nucleotide sequence is shown as SEQ ID NO: 62.

The rat $G_{\alpha 15}$ and the rat transducin α subunit can be a conservative mutant so long as they can couple with the chimeric T1R2 and chimeric T1R3. As for the conservative mutation, the above descriptions for T1R2 and T1R3 are applied. Furthermore, the positions of the regions and amino acid residues in the rat $G_{\alpha 15}$ and the rat transducin α subunit mean relative positions with respect to the amino acid sequences of SEQ ID NOS: 60 and 62, as described for the chimeric T1R2 and chimeric T1R3.

For making a cell that can express the $G_\alpha$ protein, a nucleotide coding for the $G_\alpha$ protein can be introduced into a host cell in an expressible form. The vector and promoter to be used, gene transfer, and so forth can be the same as those described for the chimeric T1R2 and chimeric T1R3.

When the host cell can inherently express a G protein that can couple with a chimeric T1R2 and chimeric T1R3, it is not necessary to introduce a nucleotide coding for the $G_\alpha$ protein into the cell, but it can be introduced.

<3> Detection of Sweet Taste Substance or Sweet Taste-regulating Substance

By contacting a test substance with such a cell that expresses T1R2 and T1R3 (at least one of them is a chimeric protein) as described above, a cell that can further expresses a G$_\alpha$ protein, and detect an interaction of the proteins and the test substance, a sweet taste substance or sweet taste-regulating substance can be detected. When a sweet taste-regulating substance is detected by the above method, the sweet taste substance can be placed in contact with the cell that expresses the T1R2 protein and the T1R3 protein together with the test substance.

The expression of "detecting an interaction of T1R2 protein and/or T1R3 protein and a test substance" does not necessarily mean only directly detecting an interaction of a T1R2 protein and/or T1R3 protein and a test substance, but such an interaction can be indirectly detected. For example, the interaction can be detected by measuring a signal transmitted via a G protein. This signal can be measured on the basis of production of a second messenger. Examples of the second messenger include calcium ion, cAMP, cGMP, and so forth, and it differs depending on the type of the G protein. For example, when the G protein is one belonging to the Gq family such as GIs/Gm, the signal can be measured on the basis of change of intracellular calcium ion concentration. If the interaction increases, the intracellular calcium concentration becomes higher. Detection of signal transfer by GPCR is described in Methods Enzymol, vols. 237 and 238 (1994), Bourne, H. R. et al., Nature, 348:125-132 (1990), and so forth.

Furthermore, "interaction of T1R2 protein and/or T1R3 protein and a test substance" can also be expressed as interaction of a sweet taste receptor and a test substance.

After a test substance is contacted with a cell that expresses a T1R2 protein and T1R3 protein (at least one of them is a chimeric protein), if the interaction of these proteins and the test substance increases as compared to that observed without contact with the test substance, it is judged that the test substance activates a sweet taste receptor channel, and if the interaction decreases as compared to that observed in the absence of contact with the test substance, it is judged that the test substance inactivates a sweet taste receptor channel. A substance that activates a sweet taste receptor channel is judged to be a sweet taste substance. Furthermore, when a test substance and a sweet taste substance are contacted with the cell, if the interaction increases as compared to that observed in the absence of contact with the test substance, it is judged that the test substance is a sweet taste substance, or a substance that enhances sweet taste of the sweet taste substance. Furthermore, when a test substance and a sweet taste substance are placed in contact with the cell, if the interaction decreases as compared to that observed in the absence of contact with the test substance, it is judged that the test substance is a substance that reduces sweet taste of the sweet taste substance. The sweet taste-regulating substance means such a substance that enhances or reduces sweet taste of a sweet taste substance.

EXAMPLES

Hereafter, the present invention will be more specifically explained with reference to the following non-limiting examples.

Example 1

Construction of Taste Receptor Protein Expression Vectors

1. Construction of Human T1R2 Protein (hT1R2) Expression Vector

The sequence of the full length cDNA coding for the human T1R2 protein is registered at GenBank of NCBI (accession No. NM_152232), and by referring to this sequence, the full length cDNA can be cloned from, for example, human mRNA. However, it can also be purchased as a corresponding full length cDNA (IMAGE:100014762) included in The Mammalian Gene Collection (mgc.nci.nih.gov/) (catalog number OHS4559-99620754, Open Biosystems). By using this plasmid as the template, an oligonucleotide having the nucleotide sequence of SEQ ID NO: 1 (the EcoRI recognition sequence was added to the 5' end) as the forward primer, and an oligonucleotide having the nucleotide sequence of SEQ ID NO: 2 (the XbaI recognition sequence was added to the 5' end) as the reverse primer, PCR was performed. The obtained DNA fragment was digested with the restriction enzymes EcoRI and XbaI, and then the digestion product was subcloned into the plasmid pcDNA3.1(+) (Life Technologies) at the same restriction sites. The resulting recombinant vector is henceforth referred to as "phT1R2". The plasmid pcDNA3.1 (+) described above has the promoter sequence of cytomegalovirus, and it can be used to express a polypeptide encoded by a cloned fragment in an animal cell.

2. Construction of Mouse T1R2 Protein (mT1R2) Expression Vector

The sequence of the full length cDNA coding for the mouse T1R2 protein is registered at GenBank of NCBI (accession No. NM_031873), and by referring to this sequence, the full length cDNA can be cloned from, for example, mouse mRNA. By using mouse mRNA as the template, an oligonucleotide having the nucleotide sequence of SEQ ID NO: 3 (the EcoRI recognition sequence was added to the 5' end) as the forward primer, and an oligonucleotide having the nucleotide sequence of SEQ ID NO: 4 (the NotI recognition sequence was added to the 5' end) as the reverse primer, RT-PCR was performed. The obtained DNA fragment was digested with the restriction enzymes EcoRI and NotI, and then the digestion product was subcloned into the plasmid pcDNA3.1(+) (Life Technologies) at the same restriction sites. The resulting recombinant vector is henceforth referred to as "pmT1R2".

3. Construction of Human T1R3 Protein (hT1R3) Expression Vector

The sequence of the full length cDNA coding for the human T1R3 protein is registered at GenBank of NCBI (accession No. NM_152228), and by referring to this sequence, the full length cDNA can be cloned from, for example, human mRNA. By using human mRNA as the template, an oligonucleotide having the nucleotide sequence of SEQ ID NO: 5 as the forward primer, and an oligonucleotide having the nucleotide sequence of SEQ ID NO: 6 as the reverse primer, RT-PCR was performed. The obtained DNA fragment was subcloned into the plasmid pcDNA3.1(+) at the EcoRV site. The resulting recombinant vector in which the coding region for hT1R3 is inserted in the sense direction is henceforth referred to as "phT1R3".

4. Construction of Mouse T1R3 Protein (mT1R3) Expression Vector

The sequence of the full length cDNA coding for the mouse T1R3 protein is registered at GenBank of NCBI (accession No. NM_031872), and by referring to this sequence, the full length cDNA can be cloned from, for example, mouse mRNA. However, it can also be purchased as a corresponding full length cDNA (IMAGE:100016422) included in The Mammalian Gene Collection (mgc.nci.nih.gov/) (catalog number OMM4760-99847609, Open Biosystems). By using this plasmid as the template, an oligonucleotide having the nucleotide sequence of SEQ ID NO: 7 (the EcoRI recognition sequence was added to the 5' end) as the forward primer, and an oligonucleotide having the nucleotide sequence of SEQ ID NO: 8 (the XbaI recognition sequence was added to the 5' end) as the reverse primer, PCR was performed. The obtained DNA fragment was digested with the restriction enzymes EcoRI and XbaI, and then the digestion product was subcloned into the plasmid pcDNA3.1(+) at the same restriction sites. The obtained recombinant vector is henceforth referred to as "pmT1R3".

The nucleotide sequences coding for the human T1R2, mouse T1R2, human T1R3, and mouse T1R3 are shown as SEQ ID NOS: 51, 53, 55, and 57, respectively. The amino acid sequences encoded by them are shown as SEQ ID NOS: 52, 54, 56, and 58, respectively.

Example 2

Preparation of Chimeric Genes Coding for Chimeric Proteins of Human T1R2 and Mouse T1R2 (h-mT1R2-EX5, h-mT1R2-481, and h-mT1R2-471), and Construction of Expression Vectors By PCR using the aforementioned hT1R2 and mT1R2 expression vectors (phT1R2 and pmT1R2) as the template, and primers, fragments serving as the components of the chimeric genes were each amplified, and genes coding for chimeric proteins were cloned into the plasmid pcDNA3.1(+) by using a recombination technique. Three kinds of chimeric proteins (h-mT1R2-471, h-mT1R2-481, and h-mT1R2-EX5) were prepared. Each of them was a chimeric protein that included an N-terminal part of the human T1R2, and a C-terminal part of the mouse T1R2. The positions of the parts of the chimeric proteins in the human T1R2 (GenBank accession No. NP_689418) or the mouse T1R2 (GenBank accession No. NP_114079), from which the parts were derived, and homologies of the chimeric proteins to hT1R2 and mT1R2 are shown in Table 1 and FIG. 1. For example, the indication "h(1-470)+m(475-843)" means a protein consisting of the region of positions 1 to 470 of hT1R2 and the region of positions 475 to 843 of mT1R2, which are fused in this order.

TABLE 1

| Chimeric T1R2 | Structure | Homology to hT1R2 | Homology to mT1R2 |
| --- | --- | --- | --- |
| h-mT1R2-471 | h(1-470) + m(475-843) | 87% | 82% |
| h-mT1R2-481 | h(1-480) + m(485-843) | 88% | 81% |
| h-mT1R2-EX5 | h(1-489) + m(494-843) | 88% | 81% |

1. h-mT1R2-EX5-expressing Vector

A vector that expresses h-mT1R2-EX5 was prepared by ligating two fragments as follows. By using phT1R2 as the template, an oligonucleotide having the nucleotide sequence of SEQ ID NO: 9 as the forward primer, and an oligonucleotide having the nucleotide sequence of SEQ ID NO: 10 as the reverse primer, PCR was performed. Separately, by using pmT1R2 as the template, an oligonucleotide having the nucleotide sequence of SEQ ID NO: 11 as the forward primer, and an oligonucleotide having the nucleotide sequence of SEQ ID NO: 12 as the reverse primer, PCR was performed. The obtained fragments were subcloned into the plasmid pcDNA3.1(+) at the HindIII-EcoRI site by using GENEART Seamless Cloning and Assembly Kit (A13288, Invitrogen, Life Technologies). The obtained recombinant vector was designated as ph-mT1R2-EX5, and the chimeric protein encoded by it was designated as h-mT1R2-EX5. The sequence of the coding region for h-mT1R2-EX5 is shown as SEQ ID NO: 13. The amino acid sequence of the protein encoded by this sequence is shown as SEQ ID NO: 14.

2. h-mT1R2-471-expressing Vector

A vector that expresses h-mT1R2-471 was prepared by ligating two fragments as follows. By using phT1R2 as the template, an oligonucleotide having the nucleotide sequence of SEQ ID NO: 9 as the forward primer, and an oligonucleotide having the nucleotide sequence of SEQ ID NO: 15 as the reverse primer, PCR was performed. Separately, by using pmT1R2 as the template, an oligonucleotide having the nucleotide sequence of SEQ ID NO: 16 as the forward primer, and an oligonucleotide having the nucleotide sequence of SEQ ID NO: 12 as the reverse primer, PCR was performed. The obtained fragments were subcloned into the plasmid pcDNA3.1(+) at the HindIII-EcoRI site by using GENEART Seamless Cloning and Assembly Kit (A13288, Invitrogen, Life Technologies). The obtained recombinant vector was designated as ph-mT1R2-471, and the chimeric protein encoded by it was designated as h-mT1R2-471. The sequence of the coding region for h-mT1R2-471 is shown as SEQ ID NO: 17. The amino acid sequence of the protein encoded by this sequence is shown as SEQ ID NO: 18.

3. h-mT1R2-481-expressing Vector

A vector that expresses h-mT1R2-481 was prepared by ligating two fragments as follows. By using phT1R2 as the template, an oligonucleotide having the nucleotide sequence of SEQ ID NO: 9 as the forward primer, and an oligonucleotide having the nucleotide sequence of SEQ ID NO: 19 as the reverse primer, PCR was performed. Separately, by using pmT1R2 as the template, an oligonucleotide having the nucleotide sequence of SEQ ID NO: 20 as the forward primer, and an oligonucleotide having the nucleotide sequence of SEQ ID NO: 12 as the reverse primer, PCR was performed. The obtained fragments were subcloned into the plasmid pcDNA3.1(+) at the HindIII-EcoRI site by using GENEART Seamless Cloning and Assembly Kit (A13288, Invitrogen, Life Technologies). The obtained recombinant vector was designated as ph-mT1R2-481, and the chimeric protein encoded by it was designated as h-mT1R2-481. The sequence of the coding region for h-mT1R2-481 is shown as SEQ ID NO: 21. The amino acid sequence of the protein encoded by this sequence is shown as SEQ ID NO: 22.

Example 3

Preparation of Chimeric Genes Coding for Chimeric Proteins of Human T1R3 and Mouse T1R3 (T1R3mosaicA, T1R3mosaicB, and T1R3mosaicC), and Construction of Expression Vectors By PCR using the aforementioned hT1R3 and mT1R3 expression vectors (phT1R3 and pmT1R3) as the template and primers, fragments serving as the components of the chimeric genes were each amplified, and genes coding for chimeric proteins were cloned into the plasmid pcDNA3.1(+) by using a recombination technique. Three kinds of chimeric proteins (T1R3mosaicA, T1R3mosaicB, and T1R3mosaicC) were prepared. In all of them, the C-terminal part was derived from human T1R3, but the N-terminal part contained both a part derived from the human T1R3, and a part derived from the mouse T1R3. The positions of the parts of the chimeric proteins in the human T1R3 (GenBank accession No. NP_689414) or the mouse T1R3 (GenBank accession No. NP_114078), from which the parts were derived, and homologies of the chimeric proteins to hT1R3 and mT1R3 are shown in Table 2 and FIG. 1. For example, the indication "h(1-63)+m(64-539)+h(535-852)" means a protein having the region of the positions 1 to 63 of hT1R3, the region of the positions 64 to 539 of mT1R3, and the region of the positions 535 to 852 of hT1R3, which are fused in this order.

TABLE 2

| Chimeric T1R3 | Structure | Homology to hT1R3 | Homology to mT1R3 |
| --- | --- | --- | --- |
| T1R3mosaicA | h(1-63) + m(64-539) + h(535-852) | 85% | 87% |
| T1R3mosaicB | m(1-63) + h(64-162) + m(163-539) + h(535-852) | 84% | 88% |
| T1R3mosaicC | m(1-162) + h(163-242) + m(243-539) + h(535-852) | 84% | 88% |

1. T1R3mosaicA-expressing Vector

A vector that expresses T1R3mosaicA was prepared by ligating three fragments as follows. By using phT1R3 as the template, an oligonucleotide having the nucleotide sequence of SEQ ID NO: 23 as the forward primer, and an oligonucleotide having the nucleotide sequence of SEQ ID NO: 24 as the reverse primer, PCR was performed to amplify the first fragment. Furthermore, by using phT1R3 as the template, an oligonucleotide having the nucleotide sequence of SEQ ID NO: 25 as the forward primer, and an oligonucleotide having the nucleotide sequence of SEQ ID NO: 26 as the reverse primer, PCR was performed to amplify the second fragment. Separately, by using pmT1R3 as the template, an oligonucleotide having the nucleotide sequence of SEQ ID NO: 27 as the forward primer, and an oligonucleotide having the nucleotide sequence of SEQ ID NO: 28 as the reverse primer, PCR was performed to obtain the third fragment. These three kinds of fragments were subcloned into the plasmid pcDNA3.1(+) at the HindIII-XbaI site by using GENEART Seamless Cloning and Assembly Kit (A13288, Invitrogen, Life Technologies). The obtained recombinant vector was designated as pT1R3mosaicA, and the chimeric protein encoded by it was designated as T1R3mosaicA. The sequence of the coding region for T1R3mosaicA is shown as SEQ ID NO: 29. The amino acid sequence of the protein encoded by this sequence is shown as SEQ ID NO: 30.

2. T1R3mosaicB-expressing Vector

A vector that expresses T1R3mosaicB was prepared by ligating three fragments as follows. By using pmT1R3 as the template, an oligonucleotide having the nucleotide sequence of SEQ ID NO: 31 as the forward primer, and an oligonucleotide having the nucleotide sequence of SEQ ID NO: 32 as the reverse primer, PCR was performed to amplify the first fragment. Furthermore, by using phT1R3 as the template, an oligonucleotide having the nucleotide sequence of SEQ ID NO: 33 as the forward primer, and an oligonucleotide having the nucleotide sequence of SEQ ID NO: 34 as the reverse primer, PCR was performed to amplify the second fragment. Separately, by using pT1R3mosaicA as the template, an oligonucleotide having the nucleotide sequence of SEQ ID NO: 35 as the forward primer, and an oligonucleotide having the nucleotide sequence of SEQ ID NO: 26 as the reverse primer, PCR was performed to obtain the third fragment. These three fragments were subcloned into the plasmid pcDNA3.1(+) at the HindIII-XbaI site by using GENEART Seamless Cloning and Assembly Kit (A13288, Invitrogen, Life Technologies). The obtained recombinant vector was designated as pT1R3mosaicB, and the chimeric protein encoded by it was designated as T1R3mosaicB. The sequence of the coding region for T1R3mosaicB is shown as SEQ ID NO: 36. The amino acid sequence of the protein encoded by this sequence is shown as SEQ ID NO: 37.

3. T1R3mosaicC-expressing Vector

A vector that expresses T1R3mosaicC was prepared by ligating three fragments as follows. By using pmT1R3 as the template, an oligonucleotide having the nucleotide sequence of SEQ ID NO: 31 as the forward primer, and an oligonucleotide having the nucleotide sequence of SEQ ID NO: 34 as the reverse primer, PCR was performed to amplify the first fragment. Furthermore, by using phT1R3 as the template, an oligonucleotide having the nucleotide sequence of SEQ ID NO: 35 as the forward primer, and an oligonucleotide having the nucleotide sequence of SEQ ID NO: 38 as the reverse primer, PCR was performed to amplify the second fragment. Separately, by using pT1R3mosaicA as the template, an oligonucleotide having the nucleotide sequence of SEQ ID NO: 39 as the forward primer, and an oligonucleotide having the nucleotide sequence of SEQ ID NO: 26 as the reverse primer, PCR was performed to obtain the third fragment. These three fragments were subcloned into the plasmid pcDNA3.1(+) at the HindIII-XbaI site by using GENEART Seamless Cloning and Assembly Kit (A13288, Invitrogen, Life Technologies). The obtained recombinant vector was designated as pT1R3mosaicC, and the chimeric protein encoded by it was designated as T1R3mosaicC. The sequence of the coding region for T1R3mosaicC is shown as SEQ ID NO: 40. The amino acid sequence of the protein encoded by this sequence is shown as SEQ ID NO: 41.

Example 4

Cloning of $G_{\alpha 15}$ Gene and Transducin α Subunit Gene

1. Cloning of Rat $G_{\alpha 15}$ Gene

The sequence of the full length cDNA coding for the rat $G_\alpha 15$ protein is registered at GenBank of NCBI (accession No. NM_053542), and can be cloned from rat mRNA with reference to the registered sequence. From RNA prepared from rat tongue epithelium, cDNA was prepared by using SuperScriptIII First-Strand Synthesis System for RT-PCR (18080-051, Invitrogen, Life Technologies), and PCR was performed by using the prepared cDNA as the template, an oligonucleotide having the nucleotide sequence of SEQ ID NO: 42 as the forward primer, and an oligonucleotide having the nucleotide sequence of SEQ ID NO: 43 as the reverse primer. The obtained fragment was subcloned into the plasmid pcDNA3.1(+) at the HindIII-XbaI site by using GENEART Seamless Cloning and Assembly Kit (A13288, Invitrogen, Life Technologies).

2. Cloning of Rat Transducin α Subunit Gene

The sequence of the full length cDNA coding for the rat transducin α subunit is registered at GenBank of NCBI (accession No. NM_001108950), and can be cloned from rat mRNA with reference to the registered sequence. From RNA prepared from rat tongue epithelium, cDNA was prepared by using SuperScriptIII First-Strand Synthesis System for RT-PCR (18080-051, Invitrogen, Life Technologies), and PCR was performed by using the prepared cDNA as the template, an oligonucleotide having the nucleotide sequence of SEQ ID NO: 44 as the forward primer, and an oligonucleotide having the nucleotide sequence of SEQ ID NO: 45 as the reverse primer. The obtained fragment was subcloned into the plasmid pcDNA3.1(+) at the HindIII-XbaI site by using GENEART Seamless Cloning and Assembly Kit (A13288, Invitrogen, Life Technologies).

Example 5

Preparation of Gene Coding for $G_{\alpha15}$-transducin α Subunit Chimeric Protein and Construction of Expression Vector A gene coding for a $G_{\alpha15}$-transducin α subunit chimeric protein was prepared from the DNA sequences coding for the rat $G_{\alpha15}$ and the transducin α subunit obtained in Example 4. This chimeric protein corresponds to the $G_{\alpha15}$ protein in which 48 amino acid residues on the C-terminal side are replaced with 48 amino acid residues on the C-terminal side of the transducin α subunit. In addition, in the 48 amino acid residues on the C-terminal side of the transducin α subunit, the methionine residue at the position 43 from the C-terminus is replaced with a leucine residue, and the valine residue at the position 39 is replaced with an aspartic acid residue.

PCR was performed by using the nucleotide sequence coding for the rat $G_{\alpha15}$ as the template, an oligonucleotide having the nucleotide sequence of SEQ ID NO: 42 as the forward primer, and an oligonucleotide having the nucleotide sequence of SEQ ID NO: 46 as the reverse primer to obtain a fragment of a coding region for the N-terminal side of $G_{\alpha15}$. PCR was performed by using the nucleotide sequence coding for the rat transducin α subunit as the template, an oligonucleotide having the nucleotide sequence of SEQ ID NO: 47 as the forward primer, and an oligonucleotide having the nucleotide sequence of SEQ ID NO: 48 as the reverse primer to obtain a fragment of a coding region for the C-terminal side of the transducin a subunit. These two kinds of fragments were subcloned into the plasmid pcDNA3.1(+) at the HindIII-EcoRI site by using GENEART Seamless Cloning and Assembly Kit (A13288, Invitrogen Life Technologies). The obtained recombinant vector was designated as $pG_{\alpha15}$-trans48LD, and the chimeric protein encoded by it was designated as $G_{\alpha15}$-trans48LD. The sequence of the coding region for $G_{\alpha15}$-trans48LD is shown as SEQ ID NO: 49. The amino acid sequence of the protein encoded by this sequence is shown as SEQ ID NO: 50.

Example 6

Gene Transfer into Cultured Cell and Evaluation of Activity of Sweet Taste Receptor and Measurement Sensitivity The HEK293E cells maintained by using the DMEM/Ham's F-12 medium (Nakarai Tesque) containing 10% fetal bovine serum (NICHIREI) and 1% Pen Strep (GIBCO) were washed with D-PBS(-) (Nakarai Tesque), and collected from the flask by using 0.25% Trypsin EDTA (GIBCO). The cells were centrifuged (1,200 rpm, 3 minutes), and after the supernatant was removed, suspended in 5% FBS DMEM/Ham's F-12 at a density of $0.75 \times 10^7$ cell/ml. This suspension (10 ml) was put into a 150 cm³ flask (IWAKI), and culture was performed overnight (37° C., 5% $CO_2$). On the next day, the medium was exchanged with Opti-MEM (30 ml, Invitrogen, Life Technologies), a sweet taste receptor gene mixture ($G_{\alpha15}$-trans48LD gene, various kinds of T1R2 chimeric genes, and various kinds of T1R3 chimeric genes, 63.8 μg in total) prepared by using Opti-MEM and Lipofectamin 2000 (Invitrogen, Life Technologies) was slowly added to the cell suspension, and incubation was performed (37° C., 5% $CO_2$) for 6 hours to attain gene transfer.

After the gene transfer, the cells were washed with D-PBS (-), then removed from the flask by using 0.25% Trypsin EDTA (GIBCO), and collected. After the cell number was counted, the cells were suspended in the 5% FBS DMEM medium (2.78 mM glucose, GIBCO) at a density of $0.5 \times 10^6$ cell/ml. This cell suspension was put into wells of D-Lysine coat 96-well plate (BD bioscience) in such a volume that the cell count is $7.0 \times 10^4$ cells/well, and the cells were cultured overnight.

After the culture, all the medium of the 96 wells were discarded. 200 μl of the staining solution for measurement of intracellular calcium ion' Calcium Assay Kit Express (Molecular Device), diluted 80 times with an assay buffer (20 mM HEPES, 146 mM NaCl, 1 mM MgSO4, 1.39 mM glucose, 1 mM CaC12, 2.5 mM Probenecid, 0.05% bovine serum albumin) was added to each well, and the plate was left standing at 37° C. for 30 minutes and at room temperature for 45 minutes to perform staining. After the staining, 50 μl of a solution of stimulant (sweet taste substance) prepared with the assay buffer was added to each well, and the fluorescence value was measured for 120 seconds after the stimulation by using FDSSμEELL (Hamamatsu Photonics). By measuring the fluorescence value (Ex. 480 nm, Em. 540 nm) before and after the stimulation, the change of the intracellular free calcium ion concentration caused by addition of the stimulant via a sweet taste receptor was quantitatively investigated. The measurement and analysis of the fluorescence value was performed by using the software attached to FDSSμEELL (FDSS7000EX), and ΔF/F value was calculated in accordance with the following equation, and used for the evaluation.

$$\Delta F/F = (\text{Maximum fluorescence value after stimulation} - \text{Minimum fluorescence value after stimulation})/(\text{Fluorescence value before stimulation})$$

Furthermore, by using the ΔF/F values obtained when each sweet taste substance was added, the S/N ratio was calculated. Specifically, the S/N value was calculated by using the minimum value of ΔF/F obtained when each substance was added at various concentrations as noise (N) value, and the similarly obtained maximum value of ΔF/F as the signal (S) value, and used as an index for sensitivity of the measurement of the activity of each receptor. That is, a higher S/N value means a higher sensitivity for detection of an interaction of a sweet taste receptor and a test substance, which makes it easier to detect stimulation with a sweet taste substance or sweet taste-regulating substance of a lower concentration.

The sweet taste substances used as the stimulating substance are acesulfame potassium (Tokyo Kasei Kogyo), sodium saccharin (WAKO), sucralose (SIGMA), sucrose (WAKO), and neotame (SIGMA), as well as aspartame, advantame, and SC-45647 ([3-[(S)-1-phenylethyl]-2-(4-cyanophenyl)guanidino]acetic acid, which were all synthesized in-house.

Figure 2:
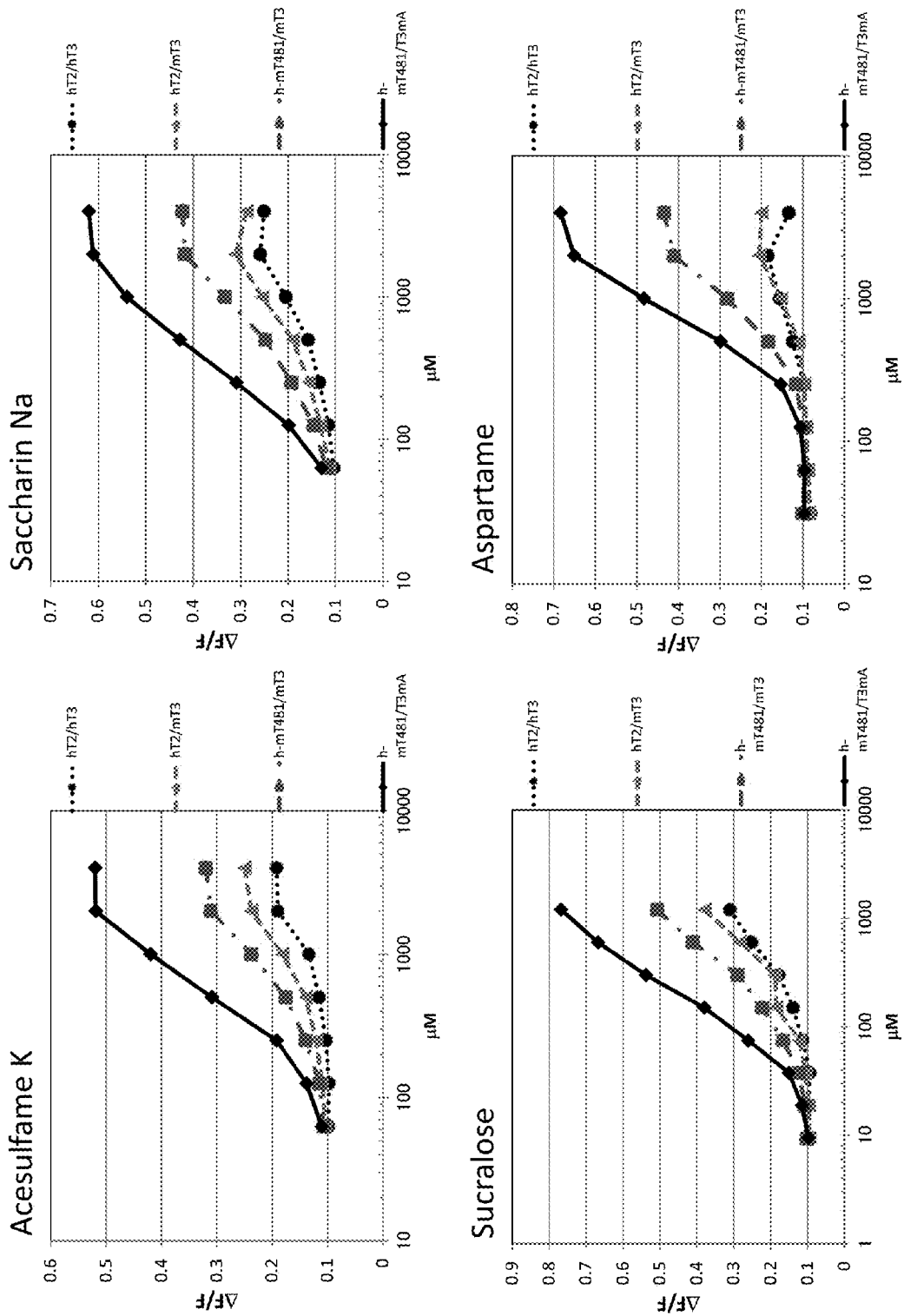
FIG. 2 shows the reaction values (ΔF/F) shown by HEK293E cells that express a chimeric T1R2 (h-mT1R2-481) and a chimeric T1R3 (T1R3mosaicA) for sweet taste substances (acesulfame K, saccharin Na, sucralose, and aspartame). In the graphs, hT2, hT3, mT2, and mT3 represent human T1R2, human T1R3, mouse T1R2, and mouse T1R3, respectively. Further, h-mT481 and T3 mA represent h-mT1R2-481 and T1R3mosaicA, respectively. The same shall apply to the following figures.
Figure 3:
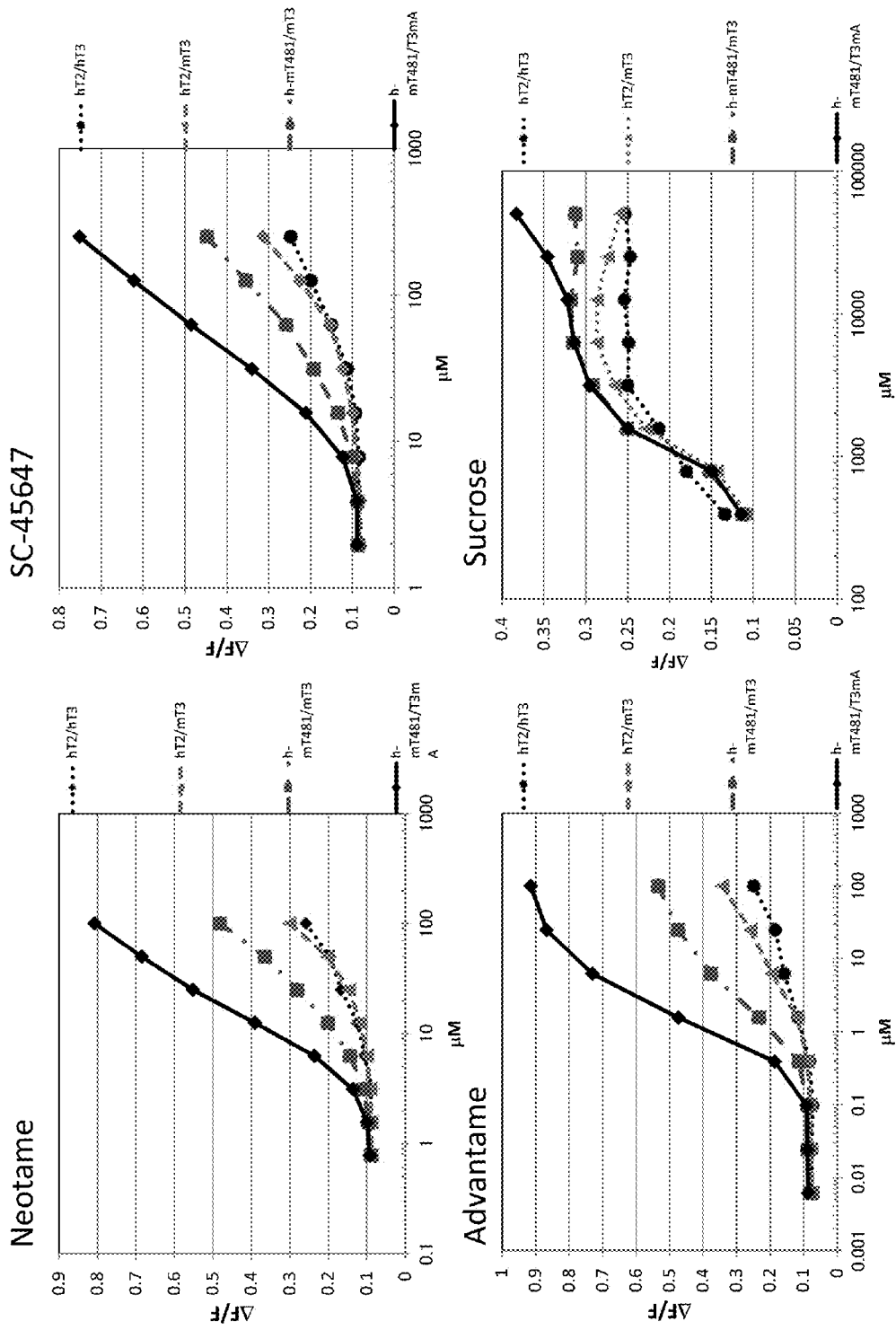
FIG. 3 shows the reaction values (ΔF/F) shown by HEK293E cells that express a chimeric T1R2 (h-mT1R2-481) and a chimeric T1R3 (T1R3mosaicA) for sweet taste substances (neotame, SC-45647, advantame, and sucrose).
Figure 4:
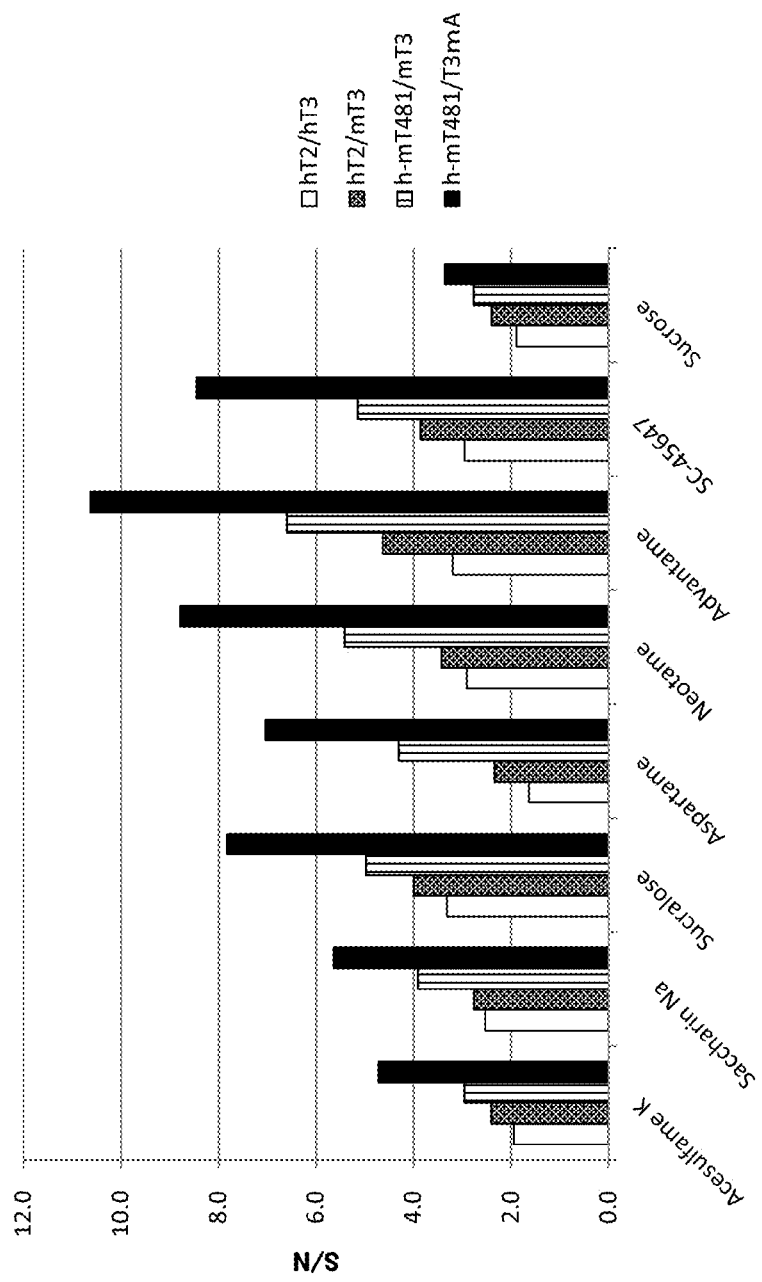
FIG. 4 shows the SN ratios of the reaction values shown by HEK293E cells that express a chimeric T1R2 (h-mT1R2-481) and a chimeric T1R3 (T1R3mosaicA) for various sweet taste substances.

1. Detection of Activity of h-mT1R2-481 and Sensitivity of Measurement hT1R2 or h-mT1R2-481, and mT1R3 or T1R3mosaicA were introduced in combination into the HEK293E cells together with $G_{\alpha15}$-trans48LD, and each sweet taste substance was added. The reaction values ($\Delta F/F$) observed as a result are shown in FIGS. 2 and 3. Furthermore, the S/N ratios are shown in FIG. 4 and Table 3.

As a result, h-mT1R2-481 showed a higher S/N value as compared to that observed with hT1R2 for all the sweet taste substances irrespective of the type of T1R3, i.e., mT1R3 or T1R3mosaicA, and thus it was demonstrated that it enables detection of activating substance for sweet taste receptor at a higher sensitivity.

Figure 5:
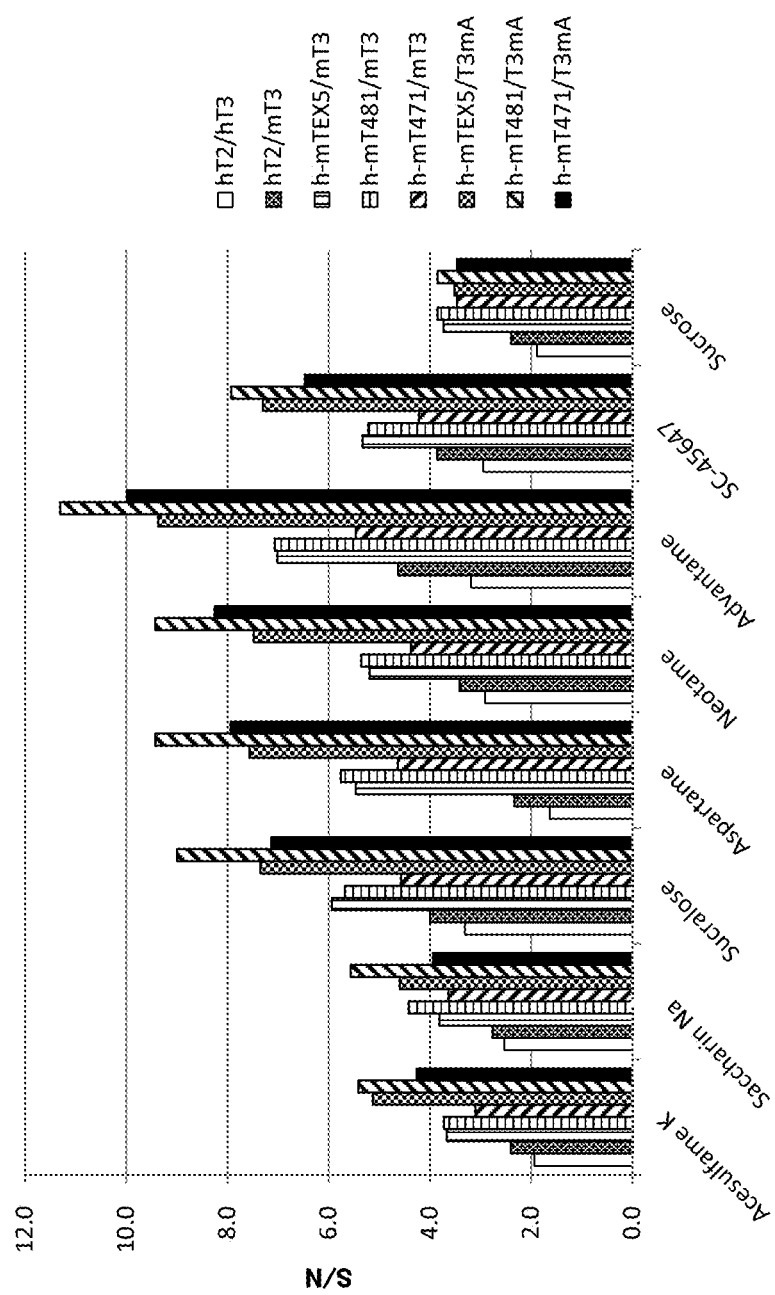
FIG. 5 shows the reaction values (ΔF/F) shown by HEK293E cells that express a chimeric T1R2 (h-mT1R2-EX5, h-mT1R2-481, or h-mT1R2-471) and a chimeric T1R3 (T1R3mosaicA) for various sweet taste substances. In the graph, h-mT471 and h-mTEX5 represent h-mT1R2-471 and h-mT1R2-EX5, respectively.

2. Detection of Activity of h-mT1R2-EX5 and h-mT1R2-471 and Sensitivity of Measurement hT1R2, h-mT1R2-EX5, h-mT1R2-481, or h-mT1R2-471, and hT1R3, mT1R3, or T1R3mosaicA were introduced in combination into the HEK293E cells together with $G_{\alpha15}$-trans48LD, each sweet taste substance was added, and the reaction values ($\Delta F/F$) were measured. The S/N ratios calculated by using the obtained $\Delta F/F$ values are shown in FIG. 5 and Table 4. As a result, h-mT1R2-EX5 and h-mT1R2-471 showed a higher S/N value compared with that observed with hT1R2 for all the sweet taste substances irrespective of the type of T1R3, i.e., mT1R3 or T1R3mosaicA. That is, in addition to h-mT1R2-481, h-mT1R2-EX5 and h-mT1R2-471 also showed a higher S/N value compared with that observed with hT1R2, and thus it was demonstrated that they enable detection of activating substance for sweet taste receptor at a higher sensitivity.

Figure 6:
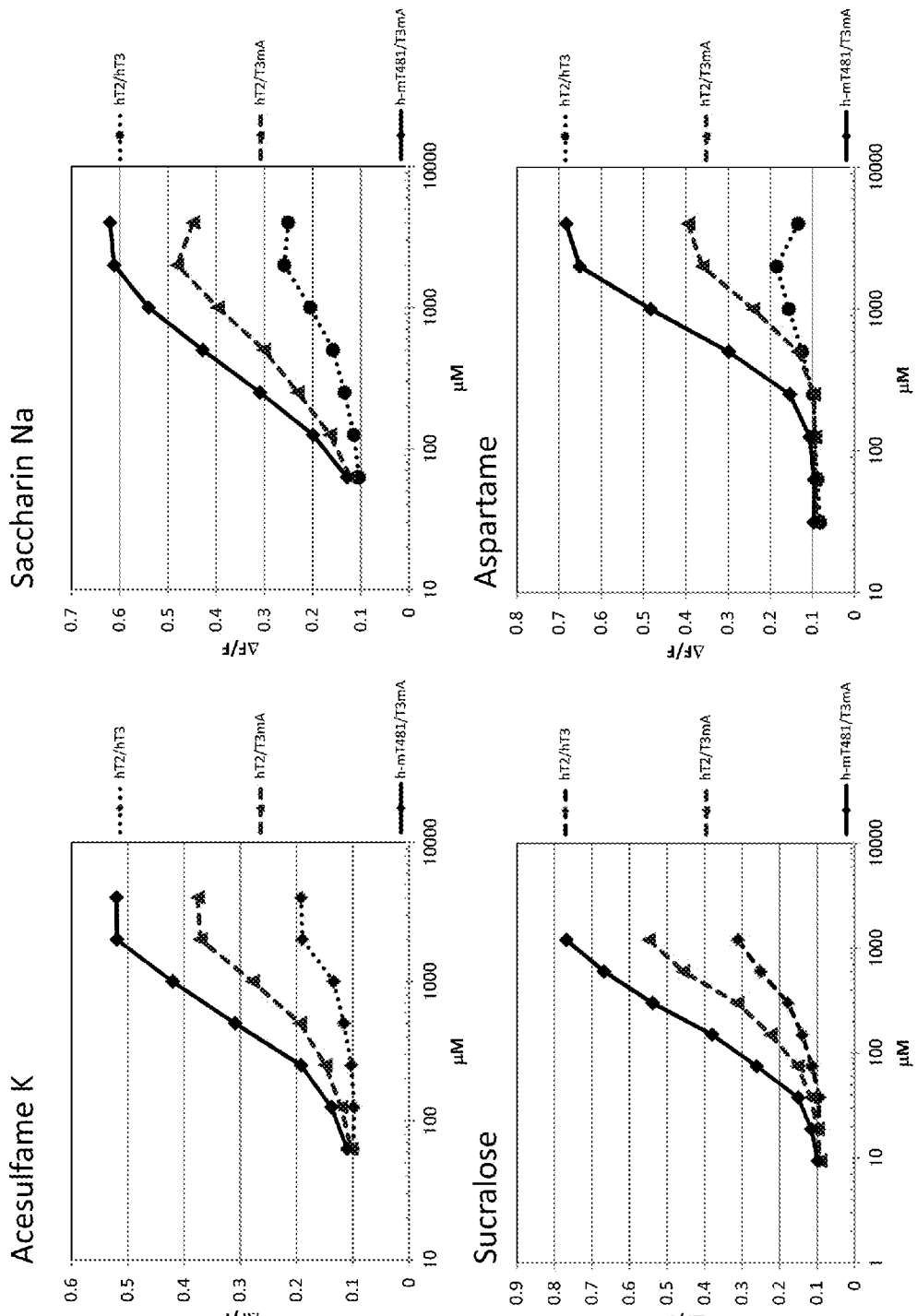
FIG. 6 shows the reaction values (ΔF/F) shown by HEK293E cells that express a chimeric T1R2 (h-mT1R2-481) and a chimeric T1R3 (T1R3mosaicA) for sweet taste substances (acesulfame K, saccharin Na, sucralose, and aspartame).
Figure 7:
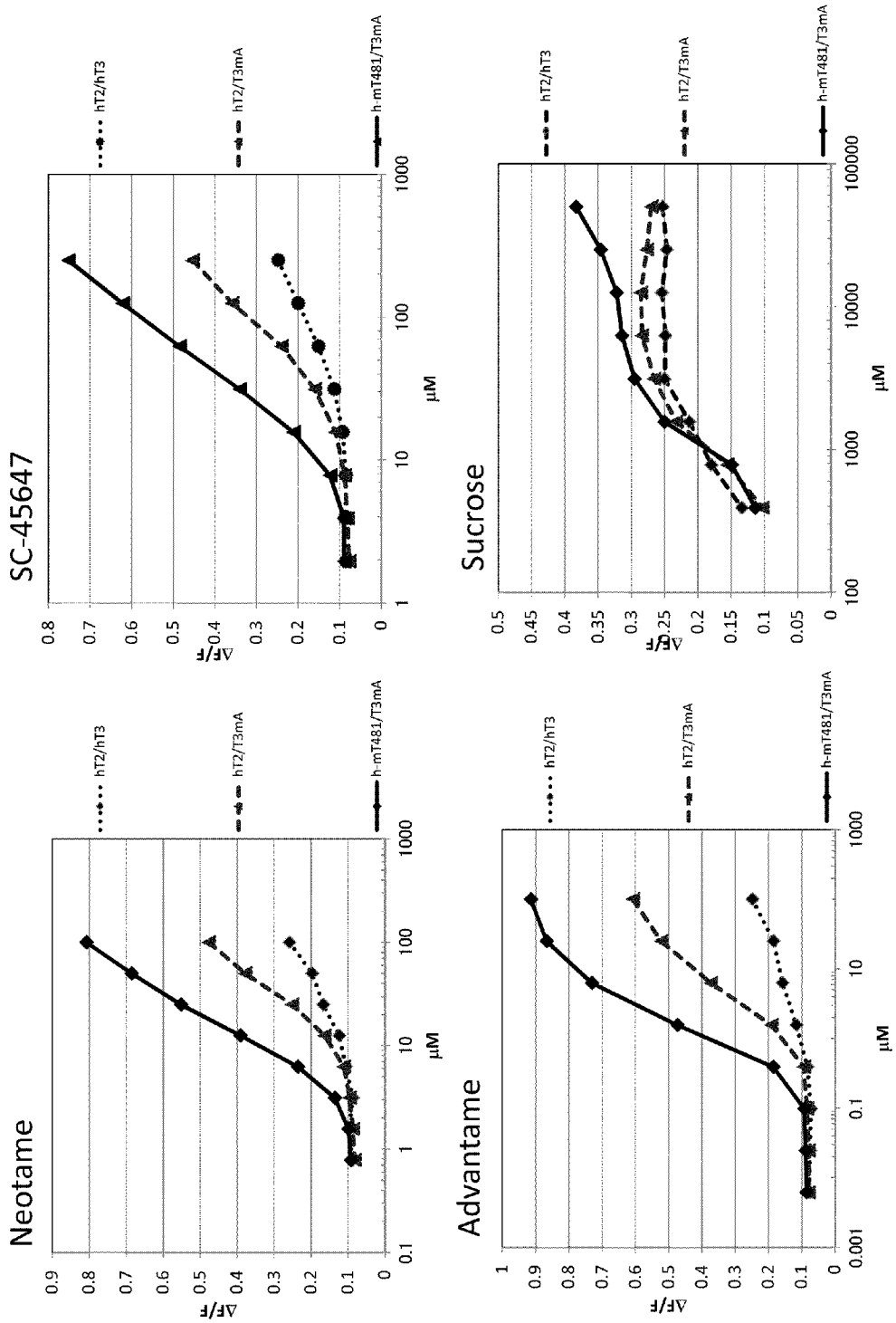
FIG. 7 shows the reaction values (ΔF/F) shown by HEK293E cells that express a chimeric T1R2 (h-mT1R2-481) and a chimeric T1R3 (T1R3mosaicA) for sweet taste substances (neotame, SC-45647, advantame, and sucrose).
Figure 8:
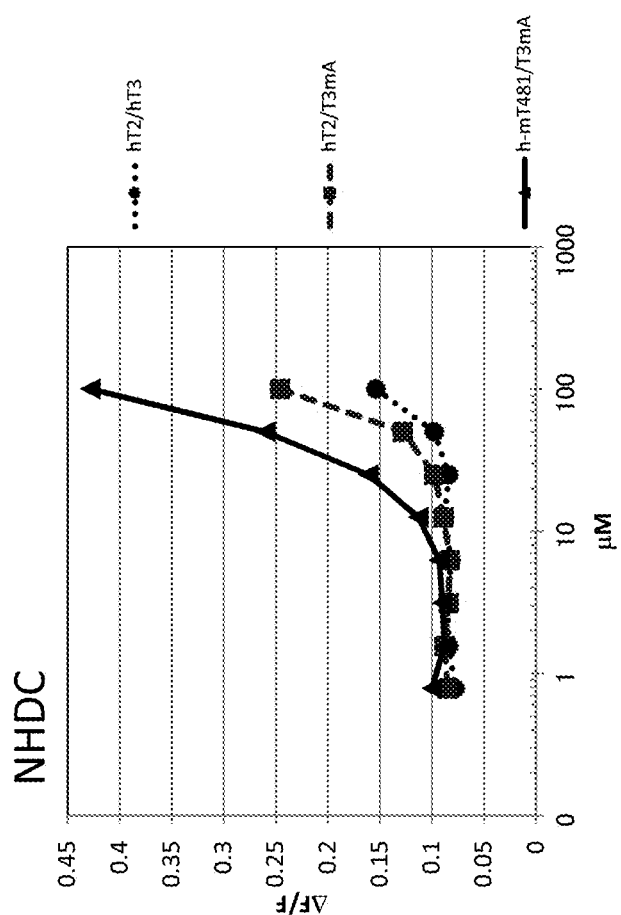
FIG. 8 shows the reaction values (ΔF/F) shown by HEK293E cells that express a chimeric T1R2 (h-mT1R2-481) and a chimeric T1R3 (T1R3mosaicA) for NHDC.
Figure 9:
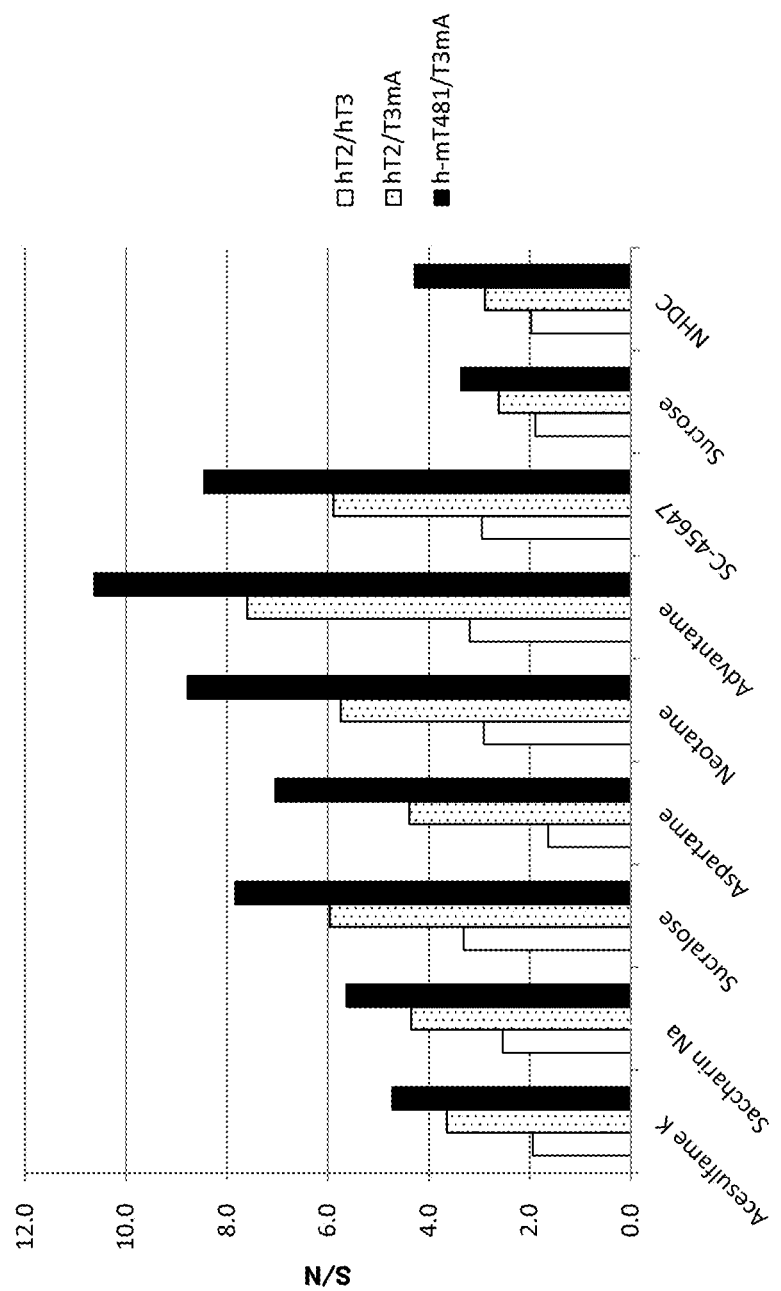
FIG. 9 shows the SN ratios of the reaction values shown by HEK293E cells that express a chimeric T1R2 (h-mT1R2-481) and a chimeric T1R3 (T1R3mosaicA) for various sweet taste substances.

3. Detection of Activity of T1R3mosaicA and Sensitivity of Measurement hT1R2 or h-mT1R2-481, and mT1R3 or T1R3mosaicA were introduced in combination into the HEK293E cells together with $G_{\alpha15}$-trans48LD, and any of the aforementioned sweet taste substances or neohesperidin dihydrochalcone (NHDC, SIGMA) was added. The reaction values ($\Delta F/F$) observed as a result are shown in FIGS. 6, 7, and 8. The S/N ratios are shown in FIG. 9 and Table 5. As a result, T1R3mosaicA showed a higher S/N value compared with that observed with hT1R3 for all the sweet taste substances irrespective of the type of T1R2, i.e., hT1R2 or h-mT1R2-481, and thus it was demonstrated that it enables detection of activating substance for sweet taste receptor at a higher sensitivity.

Figure 10:
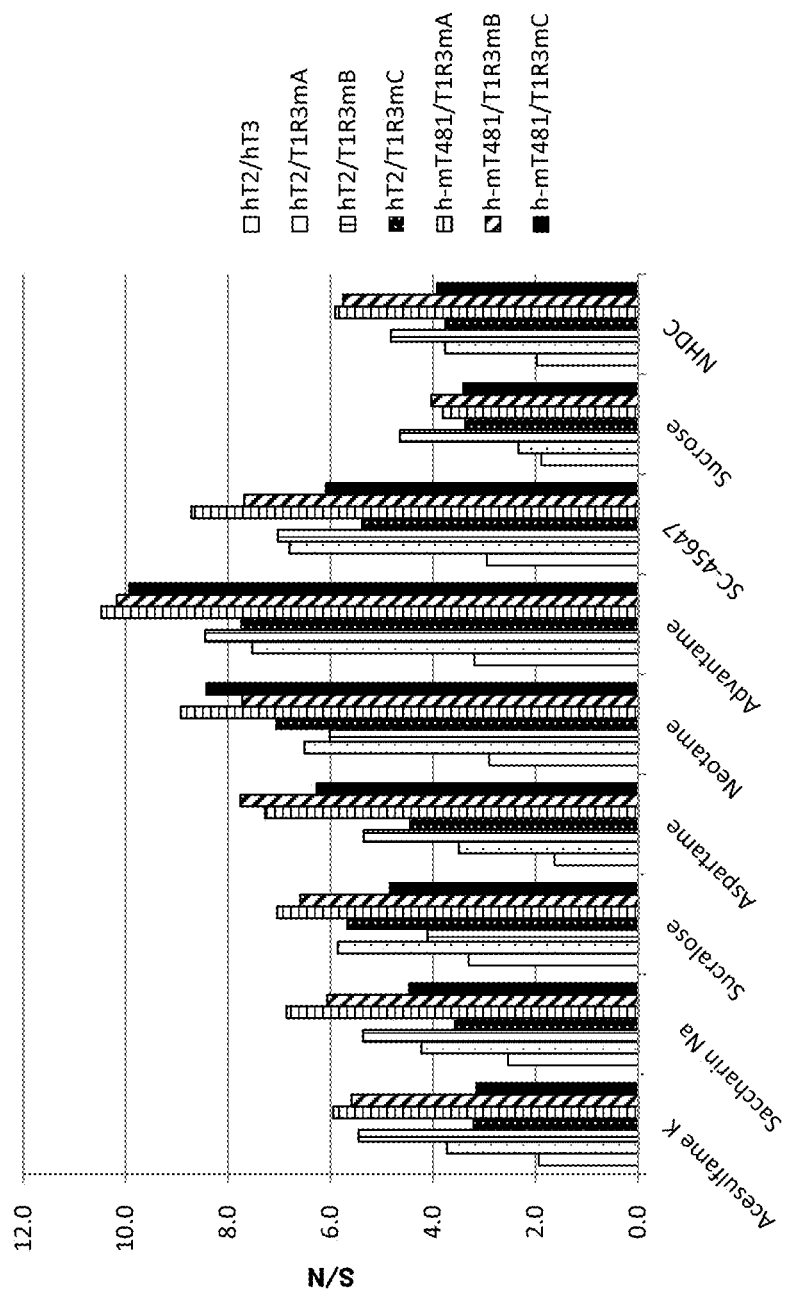
FIG. 10 shows the SN ratios of the reaction values shown by HEK293E cells that express a chimeric T1R2 (h-mT1R2-481) and a chimeric T1R3 (T1R3mosaicA, T1R3mosaicB, or T1R3mosaicC) for various sweet taste substances. T1R3 mA, T1R3mB, and T1R3mC represent T1R3mosaicA, T1R3mosaicB, and T1R3mosaicC, respectively.

4. Detection of Activities of T1R3mosaicB and T1R3mosaicC and Sensitivity of Measurement hT1R2 or h-mT1R2-481, and T1R3mosaicA, T1R3mosaicB, or T1R3mosaicC were introduced in combination into the HEK293E cells together with $G_{\alpha15}$-trans48LD, each sweet taste substance was added, and the reaction values ($\Delta F/F$) were measured. The S/N ratios calculated by using the obtained $\Delta F/F$ values are shown in FIG. 10 and Table 6. As a result, T1R3mosaicB and T1R3mosaicC showed a higher S/N value compared with that observed with hT1R2 for all the sweet taste substances irrespective of the type of T1R2, i.e., hT1R2 or h-mT1R2-481, and thus it was demonstrated that they enable detection of activating substance for sweet taste receptor at a higher sensitivity. That is, in addition to T1R3mosaicA, T1R3mosaicB and T1R3mosaicC also showed a higher S/N value compared with that observed with hT1R3, and thus it was demonstrated that they enable detection of activating substance for sweet taste receptor at a higher sensitivity.

TABLE 3

| | Gene | | S/N | | | | | | | |
|---|---|---|---|---|---|---|---|---|---|---|
| Genes | T1R2 | T1R3 | Acesulfame K | Saccharin Na | Sucralose | Aspartame | Neotame | Advantame | SC-45647 | Sucrose |
| hT2/hT3 | hT1R2 | hT1R3 | 1.9 | 2.5 | 3.3 | 1.6 | 2.9 | 3.2 | 3.0 | 1.9 |
| hT2/mT3 | hT1R2 | mT1R3 | 2.4 | 2.8 | 4.0 | 2.3 | 3.4 | 4.6 | 3.9 | 2.4 |
| h-mT481/mT3 | h-mT1R2-481 | mT1R3 | 3.0 | 3.9 | 5.0 | 4.3 | 5.4 | 6.6 | 5.1 | 2.8 |
| h-mT481/T3mA | h-mT1R2-481 | T1R3mA | 4.7 | 5.6 | 7.8 | 7.0 | 8.8 | 10.6 | 8.4 | 3.4 |

TABLE 4

| | Gene | | S/N | | | | | | | |
|---|---|---|---|---|---|---|---|---|---|---|
| Genes | T1R2 | T1R3 | Acesulfame K | Saccharin Na | Sucralose | Aspartame | Neotame | Advantame | SC-45647 | Sucrose |
| hT2/hT3 | hT1R2 | hT1R3 | 1.9 | 2.5 | 3.3 | 1.6 | 2.9 | 3.2 | 3.0 | 1.9 |
| hT2/mT3 | hT1R2 | mT1R3 | 2.4 | 2.8 | 4.0 | 2.3 | 3.4 | 4.6 | 3.9 | 2.4 |
| h-mTEX5/mT3 | h-mT1R2-EX5 | mT1R3 | 3.7 | 3.8 | 5.9 | 5.5 | 5.2 | 7.0 | 5.3 | 3.7 |
| h-mT481/mT3 | h-mT1R2-481 | mT1R3 | 3.7 | 4.4 | 5.7 | 5.8 | 5.4 | 7.1 | 5.2 | 3.9 |
| h-mT471/mT3 | h-mT1R2-471 | mT1R3 | 3.1 | 3.6 | 4.6 | 4.6 | 4.4 | 5.5 | 4.2 | 3.5 |
| h-mTEX5/T3mA | h-mT1R2-EX5 | T1R3mA | 5.1 | 4.6 | 7.4 | 7.6 | 7.5 | 9.4 | 7.3 | 3.5 |
| h-mT481/T3mA | h-mT1R2-481 | T1R3mA | 5.4 | 5.6 | 9.0 | 9.4 | 9.4 | 11.3 | 7.9 | 3.9 |
| h-mT471/T3mA | h-mT1R2-471 | T1R3mA | 4.3 | 3.9 | 7.1 | 7.9 | 8.3 | 10.0 | 6.5 | 3.5 |

TABLE 5

| Genes | Gene T1R2 | Gene T1R3 | S/N Acesulfame K | Saccharin Na | Sucralose | Aspartame | Neotame | Advantame | SC-45647 | Sucrose | NHDC |
|---|---|---|---|---|---|---|---|---|---|---|---|
| hT2/hT3 | hT1R2 | hT1R3 | 1.9 | 2.5 | 3.3 | 1.6 | 2.9 | 3.2 | 3.0 | 1.9 | 2.0 |
| hT2/T3mA | hT1R2 | T1R3mA | 3.7 | 4.3 | 6.0 | 4.4 | 5.7 | 7.6 | 5.9 | 2.6 | 2.9 |
| h-mT481/T3mA | h-mT1R2-481 | T1R3mA | 4.7 | 5.6 | 7.8 | 7.0 | 8.8 | 10.6 | 8.4 | 3.4 | 4.3 |

TABLE 6

| Genes | Gene T1R2 | Gene T1R3 | S/N Acesulfame K | Saccharin Na | Sucralose | Aspartame | Neotame | Advantame | SC-45647 | Sucrose | NHDC |
|---|---|---|---|---|---|---|---|---|---|---|---|
| hT2/hT3 | hT1R2 | hT1Rm3 | 1.9 | 2.5 | 3.3 | 1.6 | 2.9 | 3.2 | 3.0 | 1.9 | 2.0 |
| hT2/T1R3mA | hT1R2 | T1R3mA | 3.7 | 4.2 | 5.9 | 3.5 | 6.5 | 7.5 | 6.8 | 2.3 | 3.8 |
| hT2/T1R3mB | hT1R2 | T1R3mB | 5.5 | 5.4 | 4.1 | 5.4 | 6.0 | 8.5 | 7.0 | 4.7 | 4.8 |
| hT2/T1R3mC | hT1R2 | T1R3mC | 3.2 | 3.6 | 5.7 | 4.5 | 7.1 | 7.8 | 5.4 | 3.4 | 3.8 |
| h-mT481/T1Rm3A | h-mT1R2-481 | T1R3mA | 6.0 | 6.9 | 7.0 | 7.3 | 8.9 | 10.5 | 8.7 | 3.8 | 5.9 |
| h-mT481/T1R3mB | h-mT1R2-481 | T1R3mB | 5.6 | 6.1 | 6.6 | 7.8 | 7.7 | 10.2 | 7.7 | 4.0 | 5.8 |
| h-mT481/T1R3mC | h-mT1R2-481 | T1R3mC | 3.2 | 4.5 | 4.8 | 6.3 | 8.4 | 9.9 | 6.1 | 3.4 | 3.9 |

Explanation of Sequence Listing

SEQ ID NOS: 1 to 12, 15, 16, 19, 20, 23 to 28, 31 to 35, 38, 39, and 42 to 48,
Nucleotide Sequences of Primers SEQ ID NO: 13, Nucleotide sequence coding for h-mT1R2-EX5

SEQ ID NO: 14, Amino acid sequence of h-mT1R2-EX5

SEQ ID NO: 17, Nucleotide sequence coding for h-mT1R2-471

SEQ ID NO: 18, Amino acid sequence of h-mT1R2-471

SEQ ID NO: 21, Nucleotide sequence coding for h-mT1R2-481

SEQ ID NO: 22, Amino acid sequence of h-mT1R2-481

SEQ ID NO: 29, Nucleotide sequence coding for T1R3mosaicA

SEQ ID NO: 30, Amino acid sequence of T1R3mosaicA

SEQ ID NO: 36, Nucleotide sequence coding for T1R3mosaicB

SEQ ID NO: 37, Amino acid sequence of T1R3mosaicB

SEQ ID NO: 40, Nucleotide sequence coding for T1R3mosaicC

SEQ ID NO: 41, Amino acid sequence of T1R3mosaicC

SEQ ID NO: 49, Nucleotide sequence coding for $G_{\alpha 15}$-trans48LD

SEQ ID NO: 50, Amino acid sequence of $G_{\alpha 15}$-trans48LD

SEQ ID NO: 51, Nucleotide sequence coding for human T1R2

SEQ ID NO: 52, Amino acid sequence of human T1R2

SEQ ID NO: 53, Nucleotide sequence coding for mouse T1R2

SEQ ID NO: 54, Amino acid sequence of mouse T1R2

SEQ ID NO: 55, Nucleotide sequence coding for human T1R3

SEQ ID NO: 56, Amino acid sequence of human T1R3

SEQ ID NO: 57, Nucleotide sequence coding for mouse T1R3

SEQ ID NO: 58, Amino acid sequence of mouse T1R3

SEQ ID NO: 59, Nucleotide sequence coding for rat $G_{\alpha 15}$

SEQ ID NO: 60, Amino acid sequence of rat $G_{\alpha 15}$

SEQ ID NO: 61, Nucleotide sequence coding for rat transducin α subunit

SEQ ID NO: 62, Amino acid sequence of rat transducin α subunit

What is claimed is:

1. A method for detecting a sweet taste substance or a sweet taste-regulating substance comprising the steps of:
   contacting a test substance with a cell that expresses a T1R2 protein and a T1R3 protein, and
   detecting an interaction of the T1R2 protein and/or T1R3 protein and the test substance, wherein
   a) the T1R2 protein is selected from the group consisting of:
      a1) a chimeric T1R2 protein comprising the region of positions 1 to 470 of the human T1R2 protein, and the region of positions 475 to 843 of the mouse T1R2 protein, which are fused in this order,
      a2) a chimeric T1R2 protein comprising the region of positions 1 to 480 of the human T1R2 protein, and the region of positions 485 to 843 of the mouse T1R2 protein, which are fused in this order, and
      a3) a chimeric T1R2 protein comprising the region of positions 1 to 489 of the human T1R2 protein, and the region of positions 494 to 843 of the mouse T1R2 protein, which are fused in this order,
   and wherein
   b) the T1R3 protein is selected from the group consisting of:
      b1) a chimeric T1R3 protein comprising the region of positions 1 to 63 of the human T1R3 protein, the region of positions 64 to 539 of the mouse T1R3 protein, and the region of positions 535 to 852 of the human T1R3 protein, which are fused in this order,
      b2) a chimeric T1R3 protein comprising the region of positions 1 to 63 of the mouse T1R3 protein, the region of positions 64 to 162 of the human T1R3 protein, the region of positions 163 to 539 of the mouse T1R3 protein, and the region of positions 535 to 852 of the human T1R3 protein, which are fused in this order, and
      b3) a chimeric T1R3 protein comprising the region of positions 1 to 162 of the mouse T1R3 protein, the region of positions 163 to 242 of the human T1R3 protein, the region of positions 243 to 539 of the mouse T1R3 protein, and the region of positions 535 to 852 of the human T1R3 protein, which are fused in this order.

2. The method according to claim 1, wherein said contacting step comprises also contacting a sweet taste substance to the cell that expresses a T1R2 protein and a T1R3 protein.

3. The method according to claim 1, wherein the chimeric T1R2 protein has an amino acid sequence having a SEQ ID NO. selected from the group consisting of SEQ ID NOS: 18, 22, and 14.

4. The method according to claim 3, wherein the chimeric T1R3 protein has an amino acid sequence having a SEQ ID NO. selected from the group consisting of SEQ ID NOS: 30, 37, and 41.

5. The method according to claim 4, wherein the cell further expresses a G protein α subunit.

6. The method according to claim 5, wherein the G protein α subunit is a chimeric $G_\alpha$ protein comprising a region of positions 1 to 327 of rat $G_{\alpha 15}$, and a region of positions 307 to 354 of a transducin α subunit, which are fused in this order, and a methionine residue at position 312, and a valine residue at position 316 of the transducin α subunit are replaced with a leucine residue, and an aspartic acid residue, respectively.

7. The method according to claim 6, wherein the chimeric $G_\alpha$ protein has the amino acid sequence of SEQ ID NO: 50.

8. The method according to claim 7, wherein said detecting is conducted by measuring the change of intracellular free calcium ion concentration.

9. The method according to claim 8, wherein the cell is an animal cell, an insect cell, or a yeast cell.

10. The method according to claim 9, wherein the cell is a cultured cell isolated from human.

11. The method according to claim 10, wherein the cell is an HEK cell.

12. A cell that expresses a T1R2 protein and a T1R3 protein, wherein
a) the T1R2 protein is selected from the group consisting of:
   a1) a chimeric T1R2 protein comprising the region of positions 1 to 470 of the human T1R2 protein, and the region of positions 475 to 843 of the mouse T1R2 protein, which are fused in this order,
   a2) a chimeric T1R2 protein comprising the region of positions 1 to 480 of the human T1R2 protein, and the region of positions 485 to 843 of the mouse T1R2 protein, which are fused in this order,
   a3) a chimeric T1R2 protein comprising the region of positions 1 to 489 of the human T1R2 protein, and the region of positions 494 to 843 of the mouse T1R2 protein, which are fused in this order,
and wherein
b) the T1R3 protein is selected from the group consisting of:
   b1) a chimeric T1R3 protein comprising the region of positions 1 to 63 of the human T1R3 protein, the region of positions 64 to 539 of the mouse T1R3 protein, and the region of positions 535 to 852 of the human T1R3 protein, which are fused in this order,
   b2) a chimeric T1R3 protein comprising the region of positions 1 to 63 of the mouse T1R3 protein, the region of positions 64 to 162 of the human T1R3 protein, the region of positions 163 to 539 of the mouse T1R3 protein, and the region of positions 535 to 852 of the human T1R3 protein, which are fused in this order, and
   b3) a chimeric T1R3 protein comprising the region of positions 1 to 162 of the mouse T1R3 protein, the region of positions 163 to 242 of the human T1R3 protein, the region of positions 243 to 539 of the mouse T1R3 protein, and the region of positions 535 to 852 of the human T1R3 protein, which are fused in this order.

13. The cell according to claim 12, which further expresses a G protein α subunit.

14. A chimeric T1R2 protein selected from the group consisting of:
   a1) a chimeric T1R2 protein comprising the region of positions 1 to 470 of the human T1R2 protein, and the region of positions 475 to 843 of the mouse T1R2 protein, which are fused in this order,
   a2) a chimeric T1R2 protein comprising the region of positions 1 to 480 of the human T1R2 protein, and the region of positions 485 to 843 of the mouse T1R2 protein, which are fused in this order, and
   a3) a chimeric T1R2 protein comprising the region of positions 1 to 489 of the human T1R2 protein, and the region of positions 494 to 843 of the mouse T1R2 protein, which are fused in this order.

15. A chimeric T1R3 protein selected from the group consisting of:
   b1) a chimeric T1R3 protein comprising the region of positions 1 to 63 of the human T1R3 protein, the region of positions 64 to 539 of the mouse T1R3 protein, and the region of positions 535 to 852 of the human T1R3 protein, which are fused in this order,
   b2) a chimeric T1R3 protein comprising the region of positions 1 to 63 of the mouse T1R3 protein, the region of positions 64 to 162 of the human T1R3 protein, the region of positions 163 to 539 of the mouse T1R3 protein, and the region of positions 535 to 852 of the human T1R3 protein, which are fused in this order, and
   b3) a chimeric T1R3 protein comprising the region of positions 1 to 162 of the mouse T1R3 protein, the region of positions 163 to 242 of the human T1R3 protein, the region of positions 243 to 539 of the mouse T1R3 protein, and the region of positions 535 to 852 of the human T1R3 protein, which are fused in this order.

16. A polynucleotide coding for a chimeric T1R2 protein selected from the group consisting of:
   a1) a chimeric T1R2 protein comprising the region of positions 1 to 470 of the human T1R2 protein, and the region of positions 475 to 843 of the mouse T1R2 protein, which are fused in this order,
   a1) a chimeric T1R2 protein comprising the region of positions 1 to 480 of the human T1R2 protein, and the region of positions 485 to 843 of the mouse T1R2 protein, which are fused in this order, and
   a3) a chimeric T1R2 protein comprising the region of positions 1 to 489 of the human T1R2 protein, and the region of positions 494 to 843 of the mouse T1R2 protein, which are fused in this order.

17. A polynucleotide coding for a chimeric T1R3 protein selected from the group consisting of:
   b1) a chimeric T1R3 protein comprising the region of positions 1 to 63 of the human T1R3 protein, the region of positions 64 to 539 of the mouse T1R3 protein, and the region of positions 535 to 852 of the human T1R3 protein, which are fused in this order
   b2) a chimeric T1R3 protein comprising the region of positions 1 to 63 of the mouse T1R3 protein, the region of positions 64 to 162 of the human T1R3 protein, the region of positions 163 to 539 of the mouse T1R3 protein, and the region of positions 535 to 852 of the human T1R3 protein, which are fused in this order, and
   b3) a chimeric T1R3 protein comprising the region of positions 1 to 162 of the mouse T1R3 protein, the region of positions 163 to 242 of the human T1R3 protein, the region of positions 243 to 539 of the mouse T1R3 protein, and the region of positions 535 to 852 of the human T1R3 protein, which are fused in this order.

* * * * *

```
                        SEQUENCE LISTING

<160> NUMBER OF SEQ ID NOS: 62

<210> SEQ ID NO 1
<211> LENGTH: 32
<212> TYPE: DNA
<213> ORGANISM: Artificial Sequence
<220> FEATURE:
<223> OTHER INFORMATION: primer

<400> SEQUENCE: 1
cacgaattca ccatggggcc cagggcaaag ac                                   32

<210> SEQ ID NO 2
<211> LENGTH: 29
```

```
<212> TYPE: DNA
<213> ORGANISM: Artificial Sequence
<220> FEATURE:
<223> OTHER INFORMATION: primer

<400> SEQUENCE: 2
cactctagac tagtccctcc tcatggtgt                                              29

<210> SEQ ID NO 3
<211> LENGTH: 32
<212> TYPE: DNA
<213> ORGANISM: Artificial Sequence
<220> FEATURE:
<223> OTHER INFORMATION: primer

<400> SEQUENCE: 3
cacgaattca ccatgggacc ccaggcgagg ac                                          32

<210> SEQ ID NO 4
<211> LENGTH: 31
<212> TYPE: DNA
<213> ORGANISM: Artificial Sequence
<220> FEATURE:
<223> OTHER INFORMATION: primer

<400> SEQUENCE: 4
cacgcggccg cctagctctt cctcatcgtg t                                           31

<210> SEQ ID NO 5
<211> LENGTH: 23
<212> TYPE: DNA
<213> ORGANISM: Artificial Sequence
<220> FEATURE:
<223> OTHER INFORMATION: primer

<400> SEQUENCE: 5
accatgctgg gccctgctgt cct                                                    23

<210> SEQ ID NO 6
<211> LENGTH: 29
<212> TYPE: DNA
<213> ORGANISM: Artificial Sequence
<220> FEATURE:
<223> OTHER INFORMATION: primer

<400> SEQUENCE: 6
tcactcatgt ttcccctgat ttcctgtgt                                              29

<210> SEQ ID NO 7
<211> LENGTH: 32
<212> TYPE: DNA
<213> ORGANISM: Artificial Sequence
<220> FEATURE:
<223> OTHER INFORMATION: primer

<400> SEQUENCE: 7
cacgaattca ccatgccagc tttggctatc at                                          32

<210> SEQ ID NO 8
<211> LENGTH: 29
<212> TYPE: DNA
<213> ORGANISM: Artificial Sequence
<220> FEATURE:
<223> OTHER INFORMATION: primer

<400> SEQUENCE: 8
```

```
cactctagat cattcattgt gtccctgag                                              29

<210> SEQ ID NO 9
<211> LENGTH: 39
<212> TYPE: DNA
<213> ORGANISM: Artificial Sequence
<220> FEATURE:
<223> OTHER INFORMATION: primer

<400> SEQUENCE: 9
tagcgtttaa acttaccacc atggggccca gggcaaaga                                    39

<210> SEQ ID NO 10
<211> LENGTH: 35
<212> TYPE: DNA
<213> ORGANISM: Artificial Sequence
<220> FEATURE:
<223> OTHER INFORMATION: primer

<400> SEQUENCE: 10
ggggaccgtg ttgttgatgg tgtgccagga gatgt                                        35

<210> SEQ ID NO 11
<211> LENGTH: 35
<212> TYPE: DNA
<213> ORGANISM: Artificial Sequence
<220> FEATURE:
<223> OTHER INFORMATION: primer

<400> SEQUENCE: 11
aacaacacgg tccccatatc catgtgttct aagag                                        35

<210> SEQ ID NO 12
<211> LENGTH: 42
<212> TYPE: DNA
<213> ORGANISM: Artificial Sequence
<220> FEATURE:
<223> OTHER INFORMATION: primer

<400> SEQUENCE: 12
gctggatatc tgcagctagc tcttcctcat cgtgtagccc tg                                42

<210> SEQ ID NO 13
<211> LENGTH: 2520
<212> TYPE: DNA
<213> ORGANISM: Artificial Sequence
<220> FEATURE:
<223> OTHER INFORMATION: chimeric gene
<220> FEATURE:
<221> NAME/KEY: CDS
<222> LOCATION: (1)..(2520)

<400> SEQUENCE: 13 atg ggg ccc agg gca aag acc atc tcc tcc ctg ttc ttc ctc cta tgg           48
Met Gly Pro Arg Ala Lys Thr Ile Ser Ser Leu Phe Phe Leu Leu Trp
1               5                   10                  15 gtc ctg gct gag ccg gct gag aac tcg gac ttc tac ctg cct ggg gat           96
Val Leu Ala Glu Pro Ala Glu Asn Ser Asp Phe Tyr Leu Pro Gly Asp
            20                  25                  30 tac ctc ctg ggt ggc ctc ttc tcc ctc cat gcc aac atg aag ggc att          144
Tyr Leu Leu Gly Gly Leu Phe Ser Leu His Ala Asn Met Lys Gly Ile
        35                  40                  45 gtt cac ctt aac ttc ctg cag gtg ccc atg tgc aag gag tat gaa gtg          192
Val His Leu Asn Phe Leu Gln Val Pro Met Cys Lys Glu Tyr Glu Val
    50                  55                  60
```

-continued

| | | |
|---|---|---|
| aag gtg ata ggc tac aac ctc atg cag gcc atg cgc ttt gcg gtg gag<br>Lys Val Ile Gly Tyr Asn Leu Met Gln Ala Met Arg Phe Ala Val Glu<br>65                              70                        75                        80 | 240 |
| gag atc aac aat gac agc agc ctg ctg cct ggt gtg ctg ctg ggc tat<br>Glu Ile Asn Asn Asp Ser Ser Leu Leu Pro Gly Val Leu Leu Gly Tyr<br>85                          90                        95 | 288 |
| gag atc gtg gat gtg tgc tac atc tcc aac aat gtc cag ccg gtc ctc<br>Glu Ile Val Asp Val Cys Tyr Ile Ser Asn Asn Val Gln Pro Val Leu<br>100                       105                   110 | 336 |
| tac ttc ctg gca cac gag gac aac ctc ctt ccc atc caa gag gac tac<br>Tyr Phe Leu Ala His Glu Asp Asn Leu Leu Pro Ile Gln Glu Asp Tyr<br>115                     120                   125 | 384 |
| agt aac tac att tcc cgt gtg gtg gct gtc att ggc cct gac aac tcc<br>Ser Asn Tyr Ile Ser Arg Val Val Ala Val Ile Gly Pro Asp Asn Ser<br>130                     135                   140 | 432 |
| gag tct gtc atg act gtg gcc aac ttc ctc tcc cta ttt ctc ctt cca<br>Glu Ser Val Met Thr Val Ala Asn Phe Leu Ser Leu Phe Leu Leu Pro<br>145                     150                   155                   160 | 480 |
| cag atc acc tac agc gcc atc agc gat gag ctg cga gac aag gtg cgc<br>Gln Ile Thr Tyr Ser Ala Ile Ser Asp Glu Leu Arg Asp Lys Val Arg<br>                   165                   170                   175 | 528 |
| ttc ccg gct ttg ctg cgt acc aca ccc agc gcc gac cac cac atc gag<br>Phe Pro Ala Leu Leu Arg Thr Thr Pro Ser Ala Asp His His Ile Glu<br>               180                   185                   190 | 576 |
| gcc atg gtg cag ctg atg ctg cac ttc cgc tgg aac tgg atc att gtg<br>Ala Met Val Gln Leu Met Leu His Phe Arg Trp Asn Trp Ile Ile Val<br>               195                   200                   205 | 624 |
| ctg gtg agc agc gac acc tat ggc cgc gac aat ggc cag ctg ctt ggc<br>Leu Val Ser Ser Asp Thr Tyr Gly Arg Asp Asn Gly Gln Leu Leu Gly<br>210                     215                   220 | 672 |
| gag cgc gtg gcc cgg cgc gac atc tgc atc gcc ttc cag gag acg ctg<br>Glu Arg Val Ala Arg Arg Asp Ile Cys Ile Ala Phe Gln Glu Thr Leu<br>225                     230                   235                   240 | 720 |
| ccc aca ctg cag ccc aac cag aac atg acg tca gag gag cgc cag cgc<br>Pro Thr Leu Gln Pro Asn Gln Asn Met Thr Ser Glu Glu Arg Gln Arg<br>               245                   250                   255 | 768 |
| ctg gtg acc att gtg gac aag ctg cag cag agc aca gcg cgc gtc gtg<br>Leu Val Thr Ile Val Asp Lys Leu Gln Gln Ser Thr Ala Arg Val Val<br>               260                   265                   270 | 816 |
| gtc gtg ttc tcg ccc gac ctg acc ctg tac cac ttc ttc aat gag gtg<br>Val Val Phe Ser Pro Asp Leu Thr Leu Tyr His Phe Phe Asn Glu Val<br>               275                   280                   285 | 864 |
| ctg cgc cag aac ttc act ggc gcc gtg tgg atc gcc tcc gag tcc tgg<br>Leu Arg Gln Asn Phe Thr Gly Ala Val Trp Ile Ala Ser Glu Ser Trp<br>290                     295                   300 | 912 |
| gcc atc gac ccg gtc ctg cac aac ctc acg gag ctg cgc cac ttg ggc<br>Ala Ile Asp Pro Val Leu His Asn Leu Thr Glu Leu Arg His Leu Gly<br>305                     310                   315                   320 | 960 |
| acc ttc ctg ggc atc acc atc cag agc gtg ccc atc ccg ggc ttc agt<br>Thr Phe Leu Gly Ile Thr Ile Gln Ser Val Pro Ile Pro Gly Phe Ser<br>               325                   330                   335 | 1008 |
| gag ttc cgc gag tgg ggc cca cag gct ggg ccg cca ccc ctc agc agg<br>Glu Phe Arg Glu Trp Gly Pro Gln Ala Gly Pro Pro Pro Leu Ser Arg<br>               340                   345                   350 | 1056 |
| acc agc cag agc tat acc tgc aac cag gag tgc gac aac tgc ctg aac<br>Thr Ser Gln Ser Tyr Thr Cys Asn Gln Glu Cys Asp Asn Cys Leu Asn<br>355                     360                   365 | 1104 |
| gcc acc ttg tcc ttc aac acc att ctc agg ctc tct ggg gag cgt gtc<br>Ala Thr Leu Ser Phe Asn Thr Ile Leu Arg Leu Ser Gly Glu Arg Val<br>370                     375                   380 | 1152 |

```
gtc tac agc gtg tac tct gcg gtc tat gct gtg gcc cat gcc ctg cac    1200
Val Tyr Ser Val Tyr Ser Ala Val Tyr Ala Val Ala His Ala Leu His
385                 390                 395                 400 agc ctc ctc ggc tgt gac aaa agc acc tgc acc aag agg gtg gtc tac    1248
Ser Leu Leu Gly Cys Asp Lys Ser Thr Cys Thr Lys Arg Val Val Tyr
                405                 410                 415 ccc tgg cag ctg ctt gag gag atc tgg aag gtc aac ttc act ctc ctg    1296
Pro Trp Gln Leu Leu Glu Glu Ile Trp Lys Val Asn Phe Thr Leu Leu
            420                 425                 430 gac cac caa atc ttc ttc gac ccg caa ggg gac gtg gct ctg cac ttg    1344
Asp His Gln Ile Phe Phe Asp Pro Gln Gly Asp Val Ala Leu His Leu
        435                 440                 445 gag att gtc cag tgg caa tgg gac cgg agc cag aat ccc ttc cag agc    1392
Glu Ile Val Gln Trp Gln Trp Asp Arg Ser Gln Asn Pro Phe Gln Ser
    450                 455                 460 gtc gcc tcc tac tac ccc ctg cag cga cag ctg aag aac atc caa gac    1440
Val Ala Ser Tyr Tyr Pro Leu Gln Arg Gln Leu Lys Asn Ile Gln Asp
465                 470                 475                 480 atc tcc tgg cac acc atc aac aac acg gtc ccc ata tcc atg tgt tct    1488
Ile Ser Trp His Thr Ile Asn Asn Thr Val Pro Ile Ser Met Cys Ser
                485                 490                 495 aag agt tgc cag cct ggg caa atg aaa aaa ccc ata ggc ctc cac ccg    1536
Lys Ser Cys Gln Pro Gly Gln Met Lys Lys Pro Ile Gly Leu His Pro
            500                 505                 510 tgc tgc ttc gag tgt gtg gac tgt ccg ccg ggc acc tac ctc aac cga    1584
Cys Cys Phe Glu Cys Val Asp Cys Pro Pro Gly Thr Tyr Leu Asn Arg
        515                 520                 525 tca gta gat gag ttt aac tgt ctg tcc tgc ccg ggt tcc atg tgg tct    1632
Ser Val Asp Glu Phe Asn Cys Leu Ser Cys Pro Gly Ser Met Trp Ser
    530                 535                 540 tac aag aac aac atc gct tgc ttc aag cgg cgg ctg gcc ttc ctg gag    1680
Tyr Lys Asn Asn Ile Ala Cys Phe Lys Arg Arg Leu Ala Phe Leu Glu
545                 550                 555                 560 tgg cac gaa gtg ccc act atc gtg gtg acc atc ctg gcc gcc ctg ggc    1728
Trp His Glu Val Pro Thr Ile Val Val Thr Ile Leu Ala Ala Leu Gly
                565                 570                 575 ttc atc agt acg ctg gcc att ctg ctc atc ttc tgg aga cat ttc cag    1776
Phe Ile Ser Thr Leu Ala Ile Leu Leu Ile Phe Trp Arg His Phe Gln
            580                 585                 590 acg ccc atg gtg cgc tcg gcg ggc ggc ccc atg tgc ttc ctg atg ctg    1824
Thr Pro Met Val Arg Ser Ala Gly Gly Pro Met Cys Phe Leu Met Leu
        595                 600                 605 gtg ccc ctg ctg ctg gcg ttc ggg atg gtc ccc gtg tat gtg ggc ccc    1872
Val Pro Leu Leu Leu Ala Phe Gly Met Val Pro Val Tyr Val Gly Pro
    610                 615                 620 ccc acg gtc ttc tcc tgt ttc tgc cgc cag gct ttc ttc acc gtt tgc    1920
Pro Thr Val Phe Ser Cys Phe Cys Arg Gln Ala Phe Phe Thr Val Cys
625                 630                 635                 640 ttc tcc gtc tgc ctc tcc tgc atc acg gtg cgc tcc ttc cag att gtg    1968
Phe Ser Val Cys Leu Ser Cys Ile Thr Val Arg Ser Phe Gln Ile Val
                645                 650                 655 tgc gtc ttc aag atg gcc aga cgc ctg cca agc gcc tac ggt ttc tgg    2016
Cys Val Phe Lys Met Ala Arg Arg Leu Pro Ser Ala Tyr Gly Phe Trp
            660                 665                 670 atg cgt tac cac ggg ccc tac gtc ttt gtg gcc ttc atc acg gcc gtc    2064
Met Arg Tyr His Gly Pro Tyr Val Phe Val Ala Phe Ile Thr Ala Val
        675                 680                 685 aag gtg gcc ctg gtg gca ggc aac atg ctg gcc acc acc atc aac ccc    2112
Lys Val Ala Leu Val Ala Gly Asn Met Leu Ala Thr Thr Ile Asn Pro
```

```
                690             695             700
att ggc cgg acc gac ccc gat gac ccc aat atc ata atc ctc tcc tgc    2160
Ile Gly Arg Thr Asp Pro Asp Asp Pro Asn Ile Ile Ile Leu Ser Cys
705             710             715             720 cac cct aac tac cgc aac ggg cta ctc ttc aac acc agc atg gac ttg    2208
His Pro Asn Tyr Arg Asn Gly Leu Leu Phe Asn Thr Ser Met Asp Leu
                725             730             735 ctg ctg tcc gtg ctg ggt ttc agc ttc gcg tac gtg ggc aag gaa ctg    2256
Leu Leu Ser Val Leu Gly Phe Ser Phe Ala Tyr Val Gly Lys Glu Leu
            740             745             750 ccc acc aac tac aac gaa gcc aag ttc atc acc ctc agc atg acc ttc    2304
Pro Thr Asn Tyr Asn Glu Ala Lys Phe Ile Thr Leu Ser Met Thr Phe
        755             760             765 tcc ttc acc tcc tcc atc tcc ctc tgc acg ttc atg tct gtc cac gat    2352
Ser Phe Thr Ser Ser Ile Ser Leu Cys Thr Phe Met Ser Val His Asp
    770             775             780 ggc gtg ctg gtc acc atc atg gat ctc ctg gtc act gtg ctc aac ttt    2400
Gly Val Leu Val Thr Ile Met Asp Leu Leu Val Thr Val Leu Asn Phe
785             790             795             800 ctg gcc atc ggc ttg ggg tac ttt ggc ccc aag tgt tac atg atc ctt    2448
Leu Ala Ile Gly Leu Gly Tyr Phe Gly Pro Lys Cys Tyr Met Ile Leu
                805             810             815 ttc tac ccg gag cgc aac act tca gct tat ttc aat agc atg att cag    2496
Phe Tyr Pro Glu Arg Asn Thr Ser Ala Tyr Phe Asn Ser Met Ile Gln
            820             825             830 ggc tac acg atg agg aag agc tag                                     2520
Gly Tyr Thr Met Arg Lys Ser
        835

<210> SEQ ID NO 14
<211> LENGTH: 839
<212> TYPE: PRT
<213> ORGANISM: Artificial sequence
<220> FEATURE:
<223> OTHER INFORMATION: chimeric protein

<400> SEQUENCE: 14

Met Gly Pro Arg Ala Lys Thr Ile Ser Ser Leu Phe Phe Leu Leu Trp
1               5                   10                  15

Val Leu Ala Glu Pro Ala Glu Asn Ser Asp Phe Tyr Leu Pro Gly Asp
            20                  25                  30

Tyr Leu Leu Gly Gly Leu Phe Ser Leu His Ala Asn Met Lys Gly Ile
        35                  40                  45

Val His Leu Asn Phe Leu Gln Val Pro Met Cys Lys Glu Tyr Glu Val
    50                  55                  60

Lys Val Ile Gly Tyr Asn Leu Met Gln Ala Met Arg Phe Ala Val Glu
65                  70                  75                  80

Glu Ile Asn Asn Asp Ser Ser Leu Leu Pro Gly Val Leu Leu Gly Tyr
                85                  90                  95

Glu Ile Val Asp Val Cys Tyr Ile Ser Asn Asn Val Gln Pro Val Leu
            100                 105                 110

Tyr Phe Leu Ala His Glu Asp Asn Leu Leu Pro Ile Gln Glu Asp Tyr
        115                 120                 125

Ser Asn Tyr Ile Ser Arg Val Val Ala Val Ile Gly Pro Asp Asn Ser
    130                 135                 140

Glu Ser Val Met Thr Val Ala Asn Phe Leu Ser Leu Phe Leu Leu Pro
145                 150                 155                 160

Gln Ile Thr Tyr Ser Ala Ile Ser Asp Glu Leu Arg Asp Lys Val Arg
```

```
                    165                 170                 175
Phe Pro Ala Leu Leu Arg Thr Thr Pro Ser Ala Asp His His Ile Glu
                180                 185                 190
Ala Met Val Gln Leu Met Leu His Phe Arg Trp Asn Trp Ile Ile Val
                195                 200                 205
Leu Val Ser Ser Asp Thr Tyr Gly Arg Asp Asn Gly Gln Leu Leu Gly
                210                 215                 220
Glu Arg Val Ala Arg Arg Asp Ile Cys Ile Ala Phe Gln Glu Thr Leu
225                 230                 235                 240
Pro Thr Leu Gln Pro Asn Gln Asn Met Thr Ser Glu Glu Arg Gln Arg
                245                 250                 255
Leu Val Thr Ile Val Asp Lys Leu Gln Gln Ser Thr Ala Arg Val Val
                260                 265                 270
Val Val Phe Ser Pro Asp Leu Thr Leu Tyr His Phe Phe Asn Glu Val
                275                 280                 285
Leu Arg Gln Asn Phe Thr Gly Ala Val Trp Ile Ala Ser Glu Ser Trp
                290                 295                 300
Ala Ile Asp Pro Val Leu His Asn Leu Thr Glu Leu Arg His Leu Gly
305                 310                 315                 320
Thr Phe Leu Gly Ile Thr Ile Gln Ser Val Pro Ile Pro Gly Phe Ser
                325                 330                 335
Glu Phe Arg Glu Trp Gly Pro Gln Ala Gly Pro Pro Leu Ser Arg
                340                 345                 350
Thr Ser Gln Ser Tyr Thr Cys Asn Gln Glu Cys Asp Asn Cys Leu Asn
                355                 360                 365
Ala Thr Leu Ser Phe Asn Thr Ile Leu Arg Leu Ser Gly Glu Arg Val
370                 375                 380
Val Tyr Ser Val Tyr Ser Ala Val Tyr Ala Val Ala His Ala Leu His
385                 390                 395                 400
Ser Leu Leu Gly Cys Asp Lys Ser Thr Cys Thr Lys Arg Val Val Tyr
                405                 410                 415
Pro Trp Gln Leu Leu Glu Glu Ile Trp Lys Val Asn Phe Thr Leu Leu
                420                 425                 430
Asp His Gln Ile Phe Phe Asp Pro Gln Gly Asp Val Ala Leu His Leu
                435                 440                 445
Glu Ile Val Gln Trp Gln Trp Asp Arg Ser Gln Asn Pro Phe Gln Ser
                450                 455                 460
Val Ala Ser Tyr Tyr Pro Leu Gln Arg Gln Leu Lys Asn Ile Gln Asp
465                 470                 475                 480
Ile Ser Trp His Thr Ile Asn Asn Thr Val Pro Ile Ser Met Cys Ser
                485                 490                 495
Lys Ser Cys Gln Pro Gly Gln Met Lys Lys Pro Ile Gly Leu His Pro
                500                 505                 510
Cys Cys Phe Glu Cys Val Asp Cys Pro Pro Gly Thr Tyr Leu Asn Arg
                515                 520                 525
Ser Val Asp Glu Phe Asn Cys Leu Ser Cys Pro Gly Ser Met Trp Ser
                530                 535                 540
Tyr Lys Asn Asn Ile Ala Cys Phe Lys Arg Arg Leu Ala Phe Leu Glu
545                 550                 555                 560
Trp His Glu Val Pro Thr Ile Val Val Thr Ile Leu Ala Ala Leu Gly
                565                 570                 575
Phe Ile Ser Thr Leu Ala Ile Leu Leu Ile Phe Trp Arg His Phe Gln
                580                 585                 590
```

-continued

```
Thr Pro Met Val Arg Ser Ala Gly Gly Pro Met Cys Phe Leu Met Leu
        595                 600                 605

Val Pro Leu Leu Leu Ala Phe Gly Met Val Pro Val Tyr Val Gly Pro
610                 615                 620

Pro Thr Val Phe Ser Cys Phe Cys Arg Gln Ala Phe Phe Thr Val Cys
625                 630                 635                 640

Phe Ser Val Cys Leu Ser Cys Ile Thr Val Arg Ser Phe Gln Ile Val
                645                 650                 655

Cys Val Phe Lys Met Ala Arg Arg Leu Pro Ser Ala Tyr Gly Phe Trp
                660                 665                 670

Met Arg Tyr His Gly Pro Tyr Val Phe Val Ala Phe Ile Thr Ala Val
            675                 680                 685

Lys Val Ala Leu Val Ala Gly Asn Met Leu Ala Thr Thr Ile Asn Pro
690                 695                 700

Ile Gly Arg Thr Asp Pro Asp Pro Asn Ile Ile Leu Ser Cys
705                 710                 715                 720

His Pro Asn Tyr Arg Asn Gly Leu Leu Phe Asn Thr Ser Met Asp Leu
                725                 730                 735

Leu Leu Ser Val Leu Gly Phe Ser Phe Ala Tyr Val Gly Lys Glu Leu
            740                 745                 750

Pro Thr Asn Tyr Asn Glu Ala Lys Phe Ile Thr Leu Ser Met Thr Phe
            755                 760                 765

Ser Phe Thr Ser Ser Ile Ser Leu Cys Thr Phe Met Ser Val His Asp
        770                 775                 780

Gly Val Leu Val Thr Ile Met Asp Leu Leu Val Thr Val Leu Asn Phe
785                 790                 795                 800

Leu Ala Ile Gly Leu Gly Tyr Phe Gly Pro Lys Cys Tyr Met Ile Leu
                805                 810                 815

Phe Tyr Pro Glu Arg Asn Thr Ser Ala Tyr Phe Asn Ser Met Ile Gln
                820                 825                 830

Gly Tyr Thr Met Arg Lys Ser
        835

<210> SEQ ID NO 15
<211> LENGTH: 27
<212> TYPE: DNA
<213> ORGANISM: Artificial Sequence
<220> FEATURE:
<223> OTHER INFORMATION: primer

<400> SEQUENCE: 15
ctcggtgggg tagtaggagg cgacgct                                          27

<210> SEQ ID NO 16
<211> LENGTH: 27
<212> TYPE: DNA
<213> ORGANISM: Artificial Sequence
<220> FEATURE:
<223> OTHER INFORMATION: primer

<400> SEQUENCE: 16
tactacccca ccgagacgag gctgacc                                          27

<210> SEQ ID NO 17
<211> LENGTH: 2520
<212> TYPE: DNA
<213> ORGANISM: Artificial Sequence
<220> FEATURE:
```

<223> OTHER INFORMATION: chimeric gene
<220> FEATURE:
<221> NAME/KEY: CDS
<222> LOCATION: (1)..(2520)

<400> SEQUENCE: 17

```
atg ggg ccc agg gca aag acc atc tcc tcc ctg ttc ttc ctc cta tgg      48
Met Gly Pro Arg Ala Lys Thr Ile Ser Ser Leu Phe Phe Leu Leu Trp
1               5                   10                  15 gtc ctg gct gag ccg gct gag aac tcg gac ttc tac ctg cct ggg gat      96
Val Leu Ala Glu Pro Ala Glu Asn Ser Asp Phe Tyr Leu Pro Gly Asp
            20                  25                  30 tac ctc ctg ggt ggc ctc ttc tcc ctc cat gcc aac atg aag ggc att     144
Tyr Leu Leu Gly Gly Leu Phe Ser Leu His Ala Asn Met Lys Gly Ile
        35                  40                  45 gtt cac ctt aac ttc ctg cag gtg ccc atg tgc aag gag tat gaa gtg     192
Val His Leu Asn Phe Leu Gln Val Pro Met Cys Lys Glu Tyr Glu Val
    50                  55                  60 aag gtg ata ggc tac aac ctc atg cag gcc atg cgc ttt gcg gtg gag     240
Lys Val Ile Gly Tyr Asn Leu Met Gln Ala Met Arg Phe Ala Val Glu
65                  70                  75                  80 gag atc aac aat gac agc agc ctg ctg cct ggt gtg ctg ctg ggc tat     288
Glu Ile Asn Asn Asp Ser Ser Leu Leu Pro Gly Val Leu Leu Gly Tyr
                85                  90                  95 gag atc gtg gat gtg tgc tac atc tcc aac aat gtc cag ccg gtg ctc     336
Glu Ile Val Asp Val Cys Tyr Ile Ser Asn Asn Val Gln Pro Val Leu
            100                 105                 110 tac ttc ctg gca cac gag gac aac ctc ctt ccc atc caa gag gac tac     384
Tyr Phe Leu Ala His Glu Asp Asn Leu Leu Pro Ile Gln Glu Asp Tyr
        115                 120                 125 agt aac tac att tcc cgt gtg gtg gct gtc att ggc cct gac aac tcc     432
Ser Asn Tyr Ile Ser Arg Val Val Ala Val Ile Gly Pro Asp Asn Ser
    130                 135                 140 gag tct gtc atg act gtg gcc aac ttc ctc tcc cta ttt ctc ctt cca     480
Glu Ser Val Met Thr Val Ala Asn Phe Leu Ser Leu Phe Leu Leu Pro
145                 150                 155                 160 cag atc acc tac agc gcc atc agc gat gag ctg cga gac aag gtg cgc     528
Gln Ile Thr Tyr Ser Ala Ile Ser Asp Glu Leu Arg Asp Lys Val Arg
                165                 170                 175 ttc ccg gct ttg ctg cgt acc aca ccc agc gcc gac cac cac atc gag     576
Phe Pro Ala Leu Leu Arg Thr Thr Pro Ser Ala Asp His His Ile Glu
            180                 185                 190 gcc atg gtg cag ctg atg ctg cac ttc cgc tgg aac tgg atc att gtg     624
Ala Met Val Gln Leu Met Leu His Phe Arg Trp Asn Trp Ile Ile Val
        195                 200                 205 ctg gtg agc agc gac acc tat ggc cgc gac aat ggc cag ctg ctt ggc     672
Leu Val Ser Ser Asp Thr Tyr Gly Arg Asp Asn Gly Gln Leu Leu Gly
    210                 215                 220 gag cgc gtg gcc cgg cgc gac atc tgc atc gcc ttc cag gag acg ctg     720
Glu Arg Val Ala Arg Arg Asp Ile Cys Ile Ala Phe Gln Glu Thr Leu
225                 230                 235                 240 ccc aca ctg cag ccc aac cag aac atg acg tca gag gag cgc cag cgc     768
Pro Thr Leu Gln Pro Asn Gln Asn Met Thr Ser Glu Glu Arg Gln Arg
                245                 250                 255 ctg gtg acc att gtg gac aag ctg cag cag agc aca gcg cgc gtc gtg     816
Leu Val Thr Ile Val Asp Lys Leu Gln Gln Ser Thr Ala Arg Val Val
            260                 265                 270 gtc gtg ttc tcg ccc gac ctg acc ctg tac cac ttc ttc aat gag gtg     864
Val Val Phe Ser Pro Asp Leu Thr Leu Tyr His Phe Phe Asn Glu Val
        275                 280                 285
```

```
                                                     -continued ctg cgc cag aac ttc act ggc gcc gtg tgg atc gcc tcc gag tcc tgg    912
Leu Arg Gln Asn Phe Thr Gly Ala Val Trp Ile Ala Ser Glu Ser Trp
    290                 295                 300 gcc atc gac ccg gtc ctg cac aac ctc acg gag ctg cgc cac ttg ggc    960
Ala Ile Asp Pro Val Leu His Asn Leu Thr Glu Leu Arg His Leu Gly
305                 310                 315                 320 acc ttc ctg ggc atc acc atc cag agc gtg ccc atc ccg ggc ttc agt    1008
Thr Phe Leu Gly Ile Thr Ile Gln Ser Val Pro Ile Pro Gly Phe Ser
                325                 330                 335 gag ttc cgc gag tgg ggc cca cag gct ggg ccg cca ccc ctc agc agg    1056
Glu Phe Arg Glu Trp Gly Pro Gln Ala Gly Pro Pro Pro Leu Ser Arg
            340                 345                 350 acc agc cag agc tat acc tgc aac cag gag tgc gac aac tgc ctg aac    1104
Thr Ser Gln Ser Tyr Thr Cys Asn Gln Glu Cys Asp Asn Cys Leu Asn
        355                 360                 365 gcc acc ttg tcc ttc aac acc att ctc agg ctc tct ggg gag cgt gtc    1152
Ala Thr Leu Ser Phe Asn Thr Ile Leu Arg Leu Ser Gly Glu Arg Val
    370                 375                 380 gtc tac agc gtg tac tct gcg gtc tat gct gtg gcc cat gcc ctg cac    1200
Val Tyr Ser Val Tyr Ser Ala Val Tyr Ala Val Ala His Ala Leu His
385                 390                 395                 400 agc ctc ctc ggc tgt gac aaa agc acc tgc acc aag agg gtg gtc tac    1248
Ser Leu Leu Gly Cys Asp Lys Ser Thr Cys Thr Lys Arg Val Val Tyr
                405                 410                 415 ccc tgg cag ctg ctt gag gag atc tgg aag gtc aac ttc act ctc ctg    1296
Pro Trp Gln Leu Leu Glu Glu Ile Trp Lys Val Asn Phe Thr Leu Leu
            420                 425                 430 gac cac caa atc ttc ttc gac ccg caa ggg gac gtg gct ctg cac ttg    1344
Asp His Gln Ile Phe Phe Asp Pro Gln Gly Asp Val Ala Leu His Leu
        435                 440                 445 gag att gtc cag tgg caa tgg gac cgg agc cag aat ccc ttc cag agc    1392
Glu Ile Val Gln Trp Gln Trp Asp Arg Ser Gln Asn Pro Phe Gln Ser
    450                 455                 460 gtc gcc tcc tac tac ccc acc gag acg agg ctg acc tac att agc aat    1440
Val Ala Ser Tyr Tyr Pro Thr Glu Thr Arg Leu Thr Tyr Ile Ser Asn
465                 470                 475                 480 gtg tcc tgg tac acc ccc aac aac acg gtc ccc ata tcc atg tgt tct    1488
Val Ser Trp Tyr Thr Pro Asn Asn Thr Val Pro Ile Ser Met Cys Ser
                485                 490                 495 aag agt tgc cag cct ggg caa atg aaa aaa ccc ata ggc ctc cac ccg    1536
Lys Ser Cys Gln Pro Gly Gln Met Lys Lys Pro Ile Gly Leu His Pro
            500                 505                 510 tgc tgc ttc gag tgt gtg gac tgt ccg ccg ggc acc tac ctc aac cga    1584
Cys Cys Phe Glu Cys Val Asp Cys Pro Pro Gly Thr Tyr Leu Asn Arg
        515                 520                 525 tca gta gat gag ttt aac tgt ctg tcc tgc ccg ggt tcc atg tgg tct    1632
Ser Val Asp Glu Phe Asn Cys Leu Ser Cys Pro Gly Ser Met Trp Ser
    530                 535                 540 tac aag aac aac atc gct tgc ttc aag cgg cgg ctg gcc ttc ctg gag    1680
Tyr Lys Asn Asn Ile Ala Cys Phe Lys Arg Arg Leu Ala Phe Leu Glu
545                 550                 555                 560 tgg cac gaa gtg ccc act atc gtg gtg acc atc ctg gcc gcc ctg ggc    1728
Trp His Glu Val Pro Thr Ile Val Val Thr Ile Leu Ala Ala Leu Gly
                565                 570                 575 ttc atc agt acg ctg gcc att ctg ctc atc ttc tgg aga cat ttc cag    1776
Phe Ile Ser Thr Leu Ala Ile Leu Leu Ile Phe Trp Arg His Phe Gln
            580                 585                 590 acg ccc atg gtg cgc tcg gcg ggc ggc ccc atg tgc ttc ctg atg ctg    1824
Thr Pro Met Val Arg Ser Ala Gly Gly Pro Met Cys Phe Leu Met Leu
        595                 600                 605
```

```
gtg ccc ctg ctg ctg gcg ttc ggg atg gtc ccc gtg tat gtg ggc ccc      1872
Val Pro Leu Leu Leu Ala Phe Gly Met Val Pro Val Tyr Val Gly Pro
    610                 615                 620 ccc acg gtc ttc tcc tgt ttc tgc cgc cag gct ttc ttc acc gtt tgc      1920
Pro Thr Val Phe Ser Cys Phe Cys Arg Gln Ala Phe Phe Thr Val Cys
625                 630                 635                 640 ttc tcc gtc tgc ctc tcc tgc atc acg gtg cgc tcc ttc cag att gtg      1968
Phe Ser Val Cys Leu Ser Cys Ile Thr Val Arg Ser Phe Gln Ile Val
                645                 650                 655 tgc gtc ttc aag atg gcc aga cgc ctg cca agc gcc tac ggt ttc tgg      2016
Cys Val Phe Lys Met Ala Arg Arg Leu Pro Ser Ala Tyr Gly Phe Trp
            660                 665                 670 atg cgt tac cac ggg ccc tac gtc ttt gtg gcc ttc atc acg gcc gtc      2064
Met Arg Tyr His Gly Pro Tyr Val Phe Val Ala Phe Ile Thr Ala Val
        675                 680                 685 aag gtg gcc ctg gtg gca ggc aac atg ctg gcc acc acc atc aac ccc      2112
Lys Val Ala Leu Val Ala Gly Asn Met Leu Ala Thr Thr Ile Asn Pro
    690                 695                 700 att ggc cgg acc gac ccc gat gac ccc aat atc ata atc ctc tcc tgc      2160
Ile Gly Arg Thr Asp Pro Asp Asp Pro Asn Ile Ile Ile Leu Ser Cys
705                 710                 715                 720 cac cct aac tac cgc aac ggg cta ctc ttc aac acc agc atg gac ttg      2208
His Pro Asn Tyr Arg Asn Gly Leu Leu Phe Asn Thr Ser Met Asp Leu
                725                 730                 735 ctg ctg tcc gtg ctg ggt ttc agc ttc gcg tac gtg ggc aag gaa ctg      2256
Leu Leu Ser Val Leu Gly Phe Ser Phe Ala Tyr Val Gly Lys Glu Leu
            740                 745                 750 ccc acc aac tac aac gaa gcc aag ttc atc acc ctc agc atg acc ttc      2304
Pro Thr Asn Tyr Asn Glu Ala Lys Phe Ile Thr Leu Ser Met Thr Phe
        755                 760                 765 tcc ttc acc tcc tcc atc tcc ctc tgc acg ttc atg tct gtc cac gat      2352
Ser Phe Thr Ser Ser Ile Ser Leu Cys Thr Phe Met Ser Val His Asp
    770                 775                 780 ggc gtg ctg gtc acc atc atg gat ctc ctg gtc act gtg ctc aac ttt      2400
Gly Val Leu Val Thr Ile Met Asp Leu Leu Val Thr Val Leu Asn Phe
785                 790                 795                 800 ctg gcc atc ggc ttg ggg tac ttt ggc ccc aag tgt tac atg atc ctt      2448
Leu Ala Ile Gly Leu Gly Tyr Phe Gly Pro Lys Cys Tyr Met Ile Leu
                805                 810                 815 ttc tac ccg gag cgc aac act tca gct tat ttc aat agc atg att cag      2496
Phe Tyr Pro Glu Arg Asn Thr Ser Ala Tyr Phe Asn Ser Met Ile Gln
            820                 825                 830 ggc tac acg atg agg aag agc tag                                      2520
Gly Tyr Thr Met Arg Lys Ser
        835
```

<210> SEQ ID NO 18
<211> LENGTH: 839
<212> TYPE: PRT
<213> ORGANISM: Artificial Sequence
<220> FEATURE:
<223> OTHER INFORMATION: chimeric protein

<400> SEQUENCE: 18

```
Met Gly Pro Arg Ala Lys Thr Ile Ser Ser Leu Phe Phe Leu Leu Trp
1               5                   10                  15

Val Leu Ala Glu Pro Ala Glu Asn Ser Asp Phe Tyr Leu Pro Gly Asp
            20                  25                  30

Tyr Leu Leu Gly Gly Leu Phe Ser Leu His Ala Asn Met Lys Gly Ile
        35                  40                  45
```

```
Val His Leu Asn Phe Leu Gln Val Pro Met Cys Lys Glu Tyr Glu Val
    50                  55                  60

Lys Val Ile Gly Tyr Asn Leu Met Gln Ala Met Arg Phe Ala Val Glu
65                  70                  75                  80

Glu Ile Asn Asn Asp Ser Ser Leu Leu Pro Gly Val Leu Leu Gly Tyr
                85                  90                  95

Glu Ile Val Asp Val Cys Tyr Ile Ser Asn Asn Val Gln Pro Val Leu
            100                 105                 110

Tyr Phe Leu Ala His Glu Asp Asn Leu Leu Pro Ile Gln Glu Asp Tyr
        115                 120                 125

Ser Asn Tyr Ile Ser Arg Val Val Ala Val Ile Gly Pro Asp Asn Ser
    130                 135                 140

Glu Ser Val Met Thr Val Ala Asn Phe Leu Ser Leu Phe Leu Leu Pro
145                 150                 155                 160

Gln Ile Thr Tyr Ser Ala Ile Ser Asp Glu Leu Arg Asp Lys Val Arg
                165                 170                 175

Phe Pro Ala Leu Leu Arg Thr Thr Pro Ser Ala Asp His His Ile Glu
            180                 185                 190

Ala Met Val Gln Leu Met Leu His Phe Arg Trp Asn Trp Ile Ile Val
        195                 200                 205

Leu Val Ser Ser Asp Thr Tyr Gly Arg Asp Asn Gly Gln Leu Leu Gly
    210                 215                 220

Glu Arg Val Ala Arg Arg Asp Ile Cys Ile Ala Phe Gln Glu Thr Leu
225                 230                 235                 240

Pro Thr Leu Gln Pro Asn Gln Asn Met Thr Ser Glu Glu Arg Gln Arg
                245                 250                 255

Leu Val Thr Ile Val Asp Lys Leu Gln Gln Ser Thr Ala Arg Val Val
            260                 265                 270

Val Val Phe Ser Pro Asp Leu Thr Leu Tyr His Phe Asn Glu Val
        275                 280                 285

Leu Arg Gln Asn Phe Thr Gly Ala Val Trp Ile Ala Ser Glu Ser Trp
    290                 295                 300

Ala Ile Asp Pro Val Leu His Asn Leu Thr Glu Leu Arg His Leu Gly
305                 310                 315                 320

Thr Phe Leu Gly Ile Thr Ile Gln Ser Val Pro Ile Pro Gly Phe Ser
                325                 330                 335

Glu Phe Arg Glu Trp Gly Pro Gln Ala Gly Pro Pro Leu Ser Arg
            340                 345                 350

Thr Ser Gln Ser Tyr Thr Cys Asn Gln Glu Cys Asp Asn Cys Leu Asn
        355                 360                 365

Ala Thr Leu Ser Phe Asn Thr Ile Leu Arg Leu Ser Gly Glu Arg Val
    370                 375                 380

Val Tyr Ser Val Tyr Ser Ala Val Tyr Ala Val Ala His Ala Leu His
385                 390                 395                 400

Ser Leu Leu Gly Cys Asp Lys Ser Thr Cys Thr Lys Arg Val Val Tyr
                405                 410                 415

Pro Trp Gln Leu Leu Glu Glu Ile Trp Lys Val Asn Phe Thr Leu Leu
            420                 425                 430

Asp His Gln Ile Phe Phe Asp Pro Gln Gly Asp Val Ala Leu His Leu
        435                 440                 445

Glu Ile Val Gln Trp Gln Trp Asp Arg Ser Gln Asn Pro Phe Gln Ser
    450                 455                 460
```

```
Val Ala Ser Tyr Tyr Pro Thr Glu Thr Arg Leu Thr Tyr Ile Ser Asn
465                 470                 475                 480

Val Ser Trp Tyr Thr Pro Asn Asn Thr Val Pro Ile Ser Met Cys Ser
            485                 490                 495

Lys Ser Cys Gln Pro Gly Gln Met Lys Lys Pro Ile Gly Leu His Pro
        500                 505                 510

Cys Cys Phe Glu Cys Val Asp Cys Pro Pro Gly Thr Tyr Leu Asn Arg
        515                 520                 525

Ser Val Asp Glu Phe Asn Cys Leu Ser Cys Pro Gly Ser Met Trp Ser
    530                 535                 540

Tyr Lys Asn Asn Ile Ala Cys Phe Lys Arg Arg Leu Ala Phe Leu Glu
545                 550                 555                 560

Trp His Glu Val Pro Thr Ile Val Val Thr Ile Leu Ala Ala Leu Gly
                565                 570                 575

Phe Ile Ser Thr Leu Ala Ile Leu Leu Ile Phe Trp Arg His Phe Gln
                580                 585                 590

Thr Pro Met Val Arg Ser Ala Gly Gly Pro Met Cys Phe Leu Met Leu
            595                 600                 605

Val Pro Leu Leu Leu Ala Phe Gly Met Val Pro Val Tyr Val Gly Pro
610                 615                 620

Pro Thr Val Phe Ser Cys Phe Cys Arg Gln Ala Phe Phe Thr Val Cys
625                 630                 635                 640

Phe Ser Val Cys Leu Ser Cys Ile Thr Val Arg Ser Phe Gln Ile Val
                645                 650                 655

Cys Val Phe Lys Met Ala Arg Arg Leu Pro Ser Ala Tyr Gly Phe Trp
            660                 665                 670

Met Arg Tyr His Gly Pro Tyr Val Phe Val Ala Phe Ile Thr Ala Val
            675                 680                 685

Lys Val Ala Leu Val Ala Gly Asn Met Leu Ala Thr Thr Ile Asn Pro
        690                 695                 700

Ile Gly Arg Thr Asp Pro Asp Pro Asn Ile Ile Leu Ser Cys
705                 710                 715                 720

His Pro Asn Tyr Arg Asn Gly Leu Leu Phe Asn Thr Ser Met Asp Leu
                725                 730                 735

Leu Leu Ser Val Leu Gly Phe Ser Phe Ala Tyr Val Gly Lys Glu Leu
            740                 745                 750

Pro Thr Asn Tyr Asn Glu Ala Lys Phe Ile Thr Leu Ser Met Thr Phe
            755                 760                 765

Ser Phe Thr Ser Ser Ile Ser Leu Cys Thr Phe Met Ser Val His Asp
    770                 775                 780

Gly Val Leu Val Thr Ile Met Asp Leu Leu Val Thr Val Leu Asn Phe
785                 790                 795                 800

Leu Ala Ile Gly Leu Gly Tyr Phe Gly Pro Lys Cys Tyr Met Ile Leu
                805                 810                 815

Phe Tyr Pro Glu Arg Asn Thr Ser Ala Tyr Phe Asn Ser Met Ile Gln
            820                 825                 830

Gly Tyr Thr Met Arg Lys Ser
            835

<210> SEQ ID NO 19
<211> LENGTH: 34
<212> TYPE: DNA
<213> ORGANISM: Artificial Sequence
<220> FEATURE:
<223> OTHER INFORMATION: primer
```

<400> SEQUENCE: 19
aggacacgtc ttggatgttc ttcagctgtc gctg                                    34

<210> SEQ ID NO 20
<211> LENGTH: 32
<212> TYPE: DNA
<213> ORGANISM: Artificial Sequence
<220> FEATURE:
<223> OTHER INFORMATION: primer

<400> SEQUENCE: 20
tccaagacgt gtcctggtac accccaaca ac                                       32

<210> SEQ ID NO 21
<211> LENGTH: 2520
<212> TYPE: DNA
<213> ORGANISM: Artificial Sequence
<220> FEATURE:
<223> OTHER INFORMATION: chimeric gene
<220> FEATURE:
<221> NAME/KEY: CDS
<222> LOCATION: (1)..(2520)

<400> SEQUENCE: 21

| atg | ggg | ccc | agg | gca | aag | acc | atc | tcc | tcc | ctg | ttc | ttc | ctc | cta | tgg | 48 |
| Met | Gly | Pro | Arg | Ala | Lys | Thr | Ile | Ser | Ser | Leu | Phe | Phe | Leu | Leu | Trp | |
| 1   |     |     |     | 5   |     |     |     |     | 10  |     |     |     |     | 15  |     |     |

| gtc | ctg | gct | gag | ccg | gct | gag | aac | tcg | gac | ttc | tac | ctg | cct | ggg | gat | 96 |
| Val | Leu | Ala | Glu | Pro | Ala | Glu | Asn | Ser | Asp | Phe | Tyr | Leu | Pro | Gly | Asp | |
|     |     |     | 20  |     |     |     |     | 25  |     |     |     |     | 30  |     |     |     |

| tac | ctc | ctg | ggt | ggc | ctc | ttc | tcc | ctc | cat | gcc | aac | atg | aag | ggc | att | 144 |
| Tyr | Leu | Leu | Gly | Gly | Leu | Phe | Ser | Leu | His | Ala | Asn | Met | Lys | Gly | Ile | |
|     |     | 35  |     |     |     |     | 40  |     |     |     |     | 45  |     |     |     |     |

| gtt | cac | ctt | aac | ttc | ctg | cag | gtg | ccc | atg | tgc | aag | gag | tat | gaa | gtg | 192 |
| Val | His | Leu | Asn | Phe | Leu | Gln | Val | Pro | Met | Cys | Lys | Glu | Tyr | Glu | Val | |
|     | 50  |     |     |     |     | 55  |     |     |     |     | 60  |     |     |     |     |     |

| aag | gtg | ata | ggc | tac | aac | ctc | atg | cag | gcc | atg | cgc | ttt | gcg | gtg | gag | 240 |
| Lys | Val | Ile | Gly | Tyr | Asn | Leu | Met | Gln | Ala | Met | Arg | Phe | Ala | Val | Glu | |
| 65  |     |     |     |     | 70  |     |     |     |     | 75  |     |     |     |     | 80  |     |

| gag | atc | aac | aat | gac | agc | agc | ctg | ctg | cct | ggt | gtg | ctg | ctg | ggc | tat | 288 |
| Glu | Ile | Asn | Asn | Asp | Ser | Ser | Leu | Leu | Pro | Gly | Val | Leu | Leu | Gly | Tyr | |
|     |     |     |     | 85  |     |     |     |     | 90  |     |     |     |     | 95  |     |     |

| gag | atc | gtg | gat | gtg | tgc | tac | atc | tcc | aac | aat | gtc | cag | ccg | gtg | ctc | 336 |
| Glu | Ile | Val | Asp | Val | Cys | Tyr | Ile | Ser | Asn | Asn | Val | Gln | Pro | Val | Leu | |
|     |     |     | 100 |     |     |     |     | 105 |     |     |     |     | 110 |     |     |     |

| tac | ttc | ctg | gca | cac | gag | gac | aac | ctc | ctt | ccc | atc | caa | gag | gac | tac | 384 |
| Tyr | Phe | Leu | Ala | His | Glu | Asp | Asn | Leu | Leu | Pro | Ile | Gln | Glu | Asp | Tyr | |
|     |     | 115 |     |     |     |     | 120 |     |     |     |     | 125 |     |     |     |     |

| agt | aac | tac | att | tcc | cgt | gtg | gtg | gct | gtc | att | ggc | cct | gac | aac | tcc | 432 |
| Ser | Asn | Tyr | Ile | Ser | Arg | Val | Val | Ala | Val | Ile | Gly | Pro | Asp | Asn | Ser | |
|     | 130 |     |     |     |     | 135 |     |     |     |     | 140 |     |     |     |     |     |

| gag | tct | gtc | atg | act | gtg | gcc | aac | ttc | ctc | tcc | cta | ttt | ctc | ctt | cca | 480 |
| Glu | Ser | Val | Met | Thr | Val | Ala | Asn | Phe | Leu | Ser | Leu | Phe | Leu | Leu | Pro | |
| 145 |     |     |     |     | 150 |     |     |     |     | 155 |     |     |     |     | 160 |     |

| cag | atc | acc | tac | agc | gcc | atc | agc | gat | gag | ctg | cga | gac | aag | gtg | cgc | 528 |
| Gln | Ile | Thr | Tyr | Ser | Ala | Ile | Ser | Asp | Glu | Leu | Arg | Asp | Lys | Val | Arg | |
|     |     |     |     | 165 |     |     |     |     | 170 |     |     |     |     | 175 |     |     |

| ttc | ccg | gct | ttg | ctg | cgt | acc | aca | ccc | agc | gcc | gac | cac | cac | atc | gag | 576 |
| Phe | Pro | Ala | Leu | Leu | Arg | Thr | Thr | Pro | Ser | Ala | Asp | His | His | Ile | Glu | |
|     |     |     | 180 |     |     |     |     | 185 |     |     |     |     | 190 |     |     |     |

| gcc | atg | gtg | cag | ctg | atg | ctg | cac | ttc | cgc | tgg | aac | tgg | atc | att | gtg | 624 |

```
            Ala Met Val Gln Leu Met Leu His Phe Arg Trp Asn Trp Ile Ile Val
                    195                 200                 205 ctg gtg agc agc gac acc tat ggc cgc gac aat ggc cag ctg ctt ggc        672
Leu Val Ser Ser Asp Thr Tyr Gly Arg Asp Asn Gly Gln Leu Leu Gly
210                 215                 220 gag cgc gtg gcc cgg cgc gac atc tgc atc gcc ttc cag gag acg ctg        720
Glu Arg Val Ala Arg Arg Asp Ile Cys Ile Ala Phe Gln Glu Thr Leu
225                 230                 235                 240 ccc aca ctg cag ccc aac cag aac atg acg tca gag gag cgc cag cgc        768
Pro Thr Leu Gln Pro Asn Gln Asn Met Thr Ser Glu Glu Arg Gln Arg
                    245                 250                 255 ctg gtg acc att gtg gac aag ctg cag cag agc aca gcg cgc gtc gtg        816
Leu Val Thr Ile Val Asp Lys Leu Gln Gln Ser Thr Ala Arg Val Val
                260                 265                 270 gtc gtg ttc tcg ccc gac ctg acc ctg tac cac ttc ttc aat gag gtg        864
Val Val Phe Ser Pro Asp Leu Thr Leu Tyr His Phe Phe Asn Glu Val
            275                 280                 285 ctg cgc cag aac ttc act ggc gcc gtg tgg atc gcc tcc gag tcc tgg        912
Leu Arg Gln Asn Phe Thr Gly Ala Val Trp Ile Ala Ser Glu Ser Trp
        290                 295                 300 gcc atc gac ccg gtc ctg cac aac ctc acg gag ctg cgc cac ttg ggc        960
Ala Ile Asp Pro Val Leu His Asn Leu Thr Glu Leu Arg His Leu Gly
305                 310                 315                 320 acc ttc ctg ggc atc acc atc cag agc gtg ccc atc ccg ggc ttc agt       1008
Thr Phe Leu Gly Ile Thr Ile Gln Ser Val Pro Ile Pro Gly Phe Ser
                    325                 330                 335 gag ttc cgc gag tgg ggc cca cag gct ggg ccg cca ccc ctc agc agg       1056
Glu Phe Arg Glu Trp Gly Pro Gln Ala Gly Pro Pro Pro Leu Ser Arg
                340                 345                 350 acc agc cag agc tat acc tgc aac cag gag tgc gac aac tgc ctg aac       1104
Thr Ser Gln Ser Tyr Thr Cys Asn Gln Glu Cys Asp Asn Cys Leu Asn
            355                 360                 365 gcc acc ttg tcc ttc aac acc att ctc agg ctc tct ggg gag cgt gtc       1152
Ala Thr Leu Ser Phe Asn Thr Ile Leu Arg Leu Ser Gly Glu Arg Val
        370                 375                 380 gtc tac agc gtg tac tct gcg gtc tat gct gtg gcc cat gcc ctg cac       1200
Val Tyr Ser Val Tyr Ser Ala Val Tyr Ala Val Ala His Ala Leu His
385                 390                 395                 400 agc ctc ctc ggc tgt gac aaa agc acc tgc acc aag agg gtg gtc tac       1248
Ser Leu Leu Gly Cys Asp Lys Ser Thr Cys Thr Lys Arg Val Val Tyr
                    405                 410                 415 ccc tgg cag ctg ctt gag gag atc tgg aag gtc aac ttc act ctc ctg       1296
Pro Trp Gln Leu Leu Glu Glu Ile Trp Lys Val Asn Phe Thr Leu Leu
                420                 425                 430 gac cac caa atc ttc ttc gac ccg caa ggg gac gtg gct ctg cac ttg       1344
Asp His Gln Ile Phe Phe Asp Pro Gln Gly Asp Val Ala Leu His Leu
            435                 440                 445 gag att gtc cag tgg caa tgg gac cgg agc cag aat ccc ttc cag agc       1392
Glu Ile Val Gln Trp Gln Trp Asp Arg Ser Gln Asn Pro Phe Gln Ser
        450                 455                 460 gtc gcc tcc tac tac ccc ctg cag cga cag ctg aag aac atc caa gac       1440
Val Ala Ser Tyr Tyr Pro Leu Gln Arg Gln Leu Lys Asn Ile Gln Asp
465                 470                 475                 480 gtg tcc tgg tac acc ccc aac aac acg gtc ccc ata tcc atg tgt tct       1488
Val Ser Trp Tyr Thr Pro Asn Asn Thr Val Pro Ile Ser Met Cys Ser
                    485                 490                 495 aag agt tgc cag cct ggg caa atg aaa aaa ccc ata ggc ctc cac ccg       1536
Lys Ser Cys Gln Pro Gly Gln Met Lys Lys Pro Ile Gly Leu His Pro
                500                 505                 510
```

-continued

| | |
|---|---|
| tgc tgc ttc gag tgt gtg gac tgt ccg ccg ggc acc tac ctc aac cga<br>Cys Cys Phe Glu Cys Val Asp Cys Pro Pro Gly Thr Tyr Leu Asn Arg<br>     515                    520                    525 | 1584 |
| tca gta gat gag ttt aac tgt ctg tcc tgc ccg ggt tcc atg tgg tct<br>Ser Val Asp Glu Phe Asn Cys Leu Ser Cys Pro Gly Ser Met Trp Ser<br>530                    535                    540 | 1632 |
| tac aag aac aac atc gct tgc ttc aag cgg cgg ctg gcc ttc ctg gag<br>Tyr Lys Asn Asn Ile Ala Cys Phe Lys Arg Arg Leu Ala Phe Leu Glu<br>545                    550                    555                    560 | 1680 |
| tgg cac gaa gtg ccc act atc gtg gtg acc atc ctg gcc gcc ctg ggc<br>Trp His Glu Val Pro Thr Ile Val Val Thr Ile Leu Ala Ala Leu Gly<br>                    565                    570                    575 | 1728 |
| ttc atc agt acg ctg gcc att ctg ctc atc ttc tgg aga cat ttc cag<br>Phe Ile Ser Thr Leu Ala Ile Leu Leu Ile Phe Trp Arg His Phe Gln<br>              580                    585                    590 | 1776 |
| acg ccc atg gtg cgc tcg gcg ggc ggc ccc atg tgc ttc ctg atg ctg<br>Thr Pro Met Val Arg Ser Ala Gly Gly Pro Met Cys Phe Leu Met Leu<br>         595                    600                    605 | 1824 |
| gtg ccc ctg ctg ctg gcg ttc ggg atg gtc ccc gtg tat gtg ggc ccc<br>Val Pro Leu Leu Leu Ala Phe Gly Met Val Pro Val Tyr Val Gly Pro<br>610                    615                    620 | 1872 |
| ccc acg gtc ttc tcc tgt ttc tgc cgc cag gct ttc ttc acc gtt tgc<br>Pro Thr Val Phe Ser Cys Phe Cys Arg Gln Ala Phe Phe Thr Val Cys<br>625                    630                    635                    640 | 1920 |
| ttc tcc gtc tgc ctc tcc tgc atc acg gtg cgc tcc ttc cag att gtg<br>Phe Ser Val Cys Leu Ser Cys Ile Thr Val Arg Ser Phe Gln Ile Val<br>                    645                    650                    655 | 1968 |
| tgc gtc ttc aag atg gcc aga cgc ctg cca agc gcc tac ggt ttc tgg<br>Cys Val Phe Lys Met Ala Arg Arg Leu Pro Ser Ala Tyr Gly Phe Trp<br>              660                    665                    670 | 2016 |
| atg cgt tac cac ggg ccc tac gtc ttt gtg gcc ttc atc acg gcc gtc<br>Met Arg Tyr His Gly Pro Tyr Val Phe Val Ala Phe Ile Thr Ala Val<br>         675                    680                    685 | 2064 |
| aag gtg gcc ctg gtg gca ggc aac atg ctg gcc acc acc atc aac ccc<br>Lys Val Ala Leu Val Ala Gly Asn Met Leu Ala Thr Thr Ile Asn Pro<br>690                    695                    700 | 2112 |
| att ggc cgg acc gac ccc gat gac ccc aat atc ata atc ctc tcc tgc<br>Ile Gly Arg Thr Asp Pro Asp Asp Pro Asn Ile Ile Ile Leu Ser Cys<br>705                    710                    715                    720 | 2160 |
| cac cct aac tac cgc aac ggg cta ctc ttc aac acc agc atg gac ttg<br>His Pro Asn Tyr Arg Asn Gly Leu Leu Phe Asn Thr Ser Met Asp Leu<br>                    725                    730                    735 | 2208 |
| ctg ctg tcc gtg ctg ggt ttc agc ttc gcg tac gtg ggc aag gaa ctg<br>Leu Leu Ser Val Leu Gly Phe Ser Phe Ala Tyr Val Gly Lys Glu Leu<br>              740                    745                    750 | 2256 |
| ccc acc aac tac aac gaa gcc aag ttc atc acc ctc agc atg acc ttc<br>Pro Thr Asn Tyr Asn Glu Ala Lys Phe Ile Thr Leu Ser Met Thr Phe<br>         755                    760                    765 | 2304 |
| tcc ttc acc tcc tcc atc tcc ctc tgc acg ttc atg tct gtc cac gat<br>Ser Phe Thr Ser Ser Ile Ser Leu Cys Thr Phe Met Ser Val His Asp<br>770                    775                    780 | 2352 |
| ggc gtg ctg gtc acc atc atg gat ctc ctg gtc act gtg ctc aac ttt<br>Gly Val Leu Val Thr Ile Met Asp Leu Leu Val Thr Val Leu Asn Phe<br>785                    790                    795                    800 | 2400 |
| ctg gcc atc ggc ttg ggg tac ttt ggc ccc aag tgt tac atg atc ctt<br>Leu Ala Ile Gly Leu Gly Tyr Phe Gly Pro Lys Cys Tyr Met Ile Leu<br>                    805                    810                    815 | 2448 |
| ttc tac ccg gag cgc aac act tca gct tat ttc aat agc atg att cag<br>Phe Tyr Pro Glu Arg Asn Thr Ser Ala Tyr Phe Asn Ser Met Ile Gln<br>820                    825                    830 | 2496 |

```
ggc tac acg atg agg aag agc tag                                    2520
Gly Tyr Thr Met Arg Lys Ser
        835

<210> SEQ ID NO 22
<211> LENGTH: 839
<212> TYPE: PRT
<213> ORGANISM: Artificial Sequence
<220> FEATURE:
<223> OTHER INFORMATION: chimeric protein

<400> SEQUENCE: 22

Met Gly Pro Arg Ala Lys Thr Ile Ser Ser Leu Phe Phe Leu Leu Trp
1               5                   10                  15

Val Leu Ala Glu Pro Ala Glu Asn Ser Asp Phe Tyr Leu Pro Gly Asp
            20                  25                  30

Tyr Leu Gly Gly Leu Phe Ser Leu His Ala Asn Met Lys Gly Ile
        35                  40                  45

Val His Leu Asn Phe Leu Gln Val Pro Met Cys Lys Glu Tyr Glu Val
    50                  55                  60

Lys Val Ile Gly Tyr Asn Leu Met Gln Ala Met Arg Phe Ala Val Glu
65                  70                  75                  80

Glu Ile Asn Asn Asp Ser Ser Leu Leu Pro Gly Val Leu Leu Gly Tyr
                85                  90                  95

Glu Ile Val Asp Val Cys Tyr Ile Ser Asn Asn Val Gln Pro Val Leu
            100                 105                 110

Tyr Phe Leu Ala His Glu Asp Asn Leu Leu Pro Ile Gln Glu Asp Tyr
        115                 120                 125

Ser Asn Tyr Ile Ser Arg Val Val Ala Val Ile Gly Pro Asp Asn Ser
    130                 135                 140

Glu Ser Val Met Thr Val Ala Asn Phe Leu Ser Leu Phe Leu Leu Pro
145                 150                 155                 160

Gln Ile Thr Tyr Ser Ala Ile Ser Asp Glu Leu Arg Asp Lys Val Arg
                165                 170                 175

Phe Pro Ala Leu Leu Arg Thr Thr Pro Ser Ala Asp His His Ile Glu
            180                 185                 190

Ala Met Val Gln Leu Met Leu His Phe Arg Trp Asn Trp Ile Ile Val
        195                 200                 205

Leu Val Ser Ser Asp Thr Tyr Gly Arg Asp Asn Gly Gln Leu Leu Gly
    210                 215                 220

Glu Arg Val Ala Arg Arg Asp Ile Cys Ile Ala Phe Gln Glu Thr Leu
225                 230                 235                 240

Pro Thr Leu Gln Pro Asn Gln Asn Met Thr Ser Glu Glu Arg Gln Arg
                245                 250                 255

Leu Val Thr Ile Val Asp Lys Leu Gln Gln Ser Thr Ala Arg Val Val
            260                 265                 270

Val Val Phe Ser Pro Asp Leu Thr Leu Tyr His Phe Asn Glu Val
        275                 280                 285

Leu Arg Gln Asn Phe Thr Gly Ala Val Trp Ile Ala Ser Glu Ser Trp
    290                 295                 300

Ala Ile Asp Pro Val Leu His Asn Leu Thr Glu Leu Arg His Leu Gly
305                 310                 315                 320

Thr Phe Leu Gly Ile Thr Ile Gln Ser Val Pro Ile Pro Gly Phe Ser
                325                 330                 335

Glu Phe Arg Glu Trp Gly Pro Gln Ala Gly Pro Pro Leu Ser Arg
```

```
            340                 345                 350
Thr Ser Gln Ser Tyr Thr Cys Asn Gln Glu Cys Asp Asn Cys Leu Asn
            355                 360                 365

Ala Thr Leu Ser Phe Asn Thr Ile Leu Arg Leu Ser Gly Glu Arg Val
    370                 375                 380

Val Tyr Ser Val Tyr Ser Ala Val Tyr Ala Val Ala His Ala Leu His
385                 390                 395                 400

Ser Leu Leu Gly Cys Asp Lys Ser Thr Cys Thr Lys Arg Val Val Tyr
                    405                 410                 415

Pro Trp Gln Leu Leu Glu Glu Ile Trp Lys Val Asn Phe Thr Leu Leu
                420                 425                 430

Asp His Gln Ile Phe Phe Asp Pro Gln Gly Asp Val Ala Leu His Leu
            435                 440                 445

Glu Ile Val Gln Trp Gln Trp Asp Arg Ser Gln Asn Pro Phe Gln Ser
        450                 455                 460

Val Ala Ser Tyr Tyr Pro Leu Gln Arg Gln Leu Lys Asn Ile Gln Asp
465                 470                 475                 480

Val Ser Trp Tyr Thr Pro Asn Asn Thr Val Pro Ile Ser Met Cys Ser
                    485                 490                 495

Lys Ser Cys Gln Pro Gly Gln Met Lys Lys Pro Ile Gly Leu His Pro
                500                 505                 510

Cys Cys Phe Glu Cys Val Asp Cys Pro Pro Gly Thr Tyr Leu Asn Arg
            515                 520                 525

Ser Val Asp Glu Phe Asn Cys Leu Ser Cys Pro Gly Ser Met Trp Ser
        530                 535                 540

Tyr Lys Asn Asn Ile Ala Cys Phe Lys Arg Arg Leu Ala Phe Leu Glu
545                 550                 555                 560

Trp His Glu Val Pro Thr Ile Val Val Thr Ile Leu Ala Ala Leu Gly
                    565                 570                 575

Phe Ile Ser Thr Leu Ala Ile Leu Leu Ile Phe Trp Arg His Phe Gln
                580                 585                 590

Thr Pro Met Val Arg Ser Ala Gly Gly Pro Met Cys Phe Leu Met Leu
            595                 600                 605

Val Pro Leu Leu Leu Ala Phe Gly Met Val Pro Val Tyr Val Gly Pro
        610                 615                 620

Pro Thr Val Phe Ser Cys Phe Cys Arg Gln Ala Phe Phe Thr Val Cys
625                 630                 635                 640

Phe Ser Val Cys Leu Ser Cys Ile Thr Val Arg Ser Phe Gln Ile Val
                    645                 650                 655

Cys Val Phe Lys Met Ala Arg Arg Leu Pro Ser Ala Tyr Gly Phe Trp
                660                 665                 670

Met Arg Tyr His Gly Pro Tyr Val Phe Val Ala Phe Ile Thr Ala Val
            675                 680                 685

Lys Val Ala Leu Val Ala Gly Asn Met Leu Ala Thr Thr Ile Asn Pro
        690                 695                 700

Ile Gly Arg Thr Asp Pro Asp Pro Asn Ile Ile Leu Ser Cys
705                 710                 715                 720

His Pro Asn Tyr Arg Asn Gly Leu Leu Phe Asn Thr Ser Met Asp Leu
                    725                 730                 735

Leu Leu Ser Val Leu Gly Phe Ser Phe Ala Tyr Val Gly Lys Glu Leu
                740                 745                 750

Pro Thr Asn Tyr Asn Glu Ala Lys Phe Ile Thr Leu Ser Met Thr Phe
            755                 760                 765
```

```
Ser Phe Thr Ser Ser Ile Ser Leu Cys Thr Phe Met Ser Val His Asp
    770                 775                 780

Gly Val Leu Val Thr Ile Met Asp Leu Leu Val Thr Val Leu Asn Phe
785                 790                 795                 800

Leu Ala Ile Gly Leu Gly Tyr Phe Gly Pro Lys Cys Tyr Met Ile Leu
                805                 810                 815

Phe Tyr Pro Glu Arg Asn Thr Ser Ala Tyr Phe Asn Ser Met Ile Gln
            820                 825                 830

Gly Tyr Thr Met Arg Lys Ser
        835
```

```
<210> SEQ ID NO 23
<211> LENGTH: 44
<212> TYPE: DNA
<213> ORGANISM: Artificial Sequence
<220> FEATURE:
<223> OTHER INFORMATION: primer

<400> SEQUENCE: 23
tagcgtttaa acttaagctt gccaccatgc tgggccctgc tgtc            44

<210> SEQ ID NO 24
<211> LENGTH: 27
<212> TYPE: DNA
<213> ORGANISM: Artificial Sequence
<220> FEATURE:
<223> OTHER INFORMATION: primer

<400> SEQUENCE: 24
gggtgagaac ctggtgcaca cagggct                               27

<210> SEQ ID NO 25
<211> LENGTH: 38
<212> TYPE: DNA
<213> ORGANISM: Artificial Sequence
<220> FEATURE:
<223> OTHER INFORMATION: primer

<400> SEQUENCE: 25
agcatccaga cgacatcgcc tgcacctttt gtggccag                   38

<210> SEQ ID NO 26
<211> LENGTH: 44
<212> TYPE: DNA
<213> ORGANISM: Artificial Sequence
<220> FEATURE:
<223> OTHER INFORMATION: primer

<400> SEQUENCE: 26
gtttaaacgg gccctctaga tcactcatgt tcccctgat ttcc             44

<210> SEQ ID NO 27
<211> LENGTH: 28
<212> TYPE: DNA
<213> ORGANISM: Artificial Sequence
<220> FEATURE:
<223> OTHER INFORMATION: primer

<400> SEQUENCE: 27
gtgcaccagg ttctcacccc ttggtttg                              28

<210> SEQ ID NO 28
<211> LENGTH: 39
```

```
<212> TYPE: DNA
<213> ORGANISM: Artificial Sequence
<220> FEATURE:
<223> OTHER INFORMATION: primer

<400> SEQUENCE: 28
tgtcgtctgg atgcttccgg tagctgcccg ccttgcagt                              39

<210> SEQ ID NO 29
<211> LENGTH: 2574
<212> TYPE: DNA
<213> ORGANISM: Artificial Sequence
<220> FEATURE:
<223> OTHER INFORMATION: chimeric gene
<220> FEATURE:
<221> NAME/KEY: CDS
<222> LOCATION: (1)..(2574)

<400> SEQUENCE: 29
```

| | | | | | | | | | | | | | | | | |
|---|---|---|---|---|---|---|---|---|---|---|---|---|---|---|---|---|
| atg | ctg | ggc | cct | gct | gtc | ctg | ggc | ctc | agc | ctc | tgg | gct | ctc | ctg | cac | 48 |
| Met | Leu | Gly | Pro | Ala | Val | Leu | Gly | Leu | Ser | Leu | Trp | Ala | Leu | Leu | His | |
| 1 | | | | 5 | | | | | 10 | | | | | 15 | | |
| cct | ggg | acg | ggg | gcc | cca | ttg | tgc | ctg | tca | cag | caa | ctt | agg | atg | aag | 96 |
| Pro | Gly | Thr | Gly | Ala | Pro | Leu | Cys | Leu | Ser | Gln | Gln | Leu | Arg | Met | Lys | |
| | | 20 | | | | | 25 | | | | | 30 | | | | |
| ggg | gac | tac | gtg | ctg | ggg | ggg | ctg | ttc | ccc | ctg | ggc | gag | gcc | gag | gag | 144 |
| Gly | Asp | Tyr | Val | Leu | Gly | Gly | Leu | Phe | Pro | Leu | Gly | Glu | Ala | Glu | Glu | |
| | 35 | | | | | 40 | | | | | 45 | | | | | |
| gct | ggc | ctc | cgc | agc | cgg | aca | cgg | ccc | agc | agc | cct | gtg | tgc | acc | agg | 192 |
| Ala | Gly | Leu | Arg | Ser | Arg | Thr | Arg | Pro | Ser | Ser | Pro | Val | Cys | Thr | Arg | |
| 50 | | | | | 55 | | | | | 60 | | | | | | |
| ttc | tca | ccc | ctt | ggt | ttg | ttc | ctg | gcc | atg | gct | atg | aag | atg | gct | gtg | 240 |
| Phe | Ser | Pro | Leu | Gly | Leu | Phe | Leu | Ala | Met | Ala | Met | Lys | Met | Ala | Val | |
| 65 | | | | 70 | | | | | 75 | | | | | 80 | | |
| gag | gag | atc | aac | aat | gga | tct | gcc | ttg | ctc | cct | ggg | ctg | cgg | ctg | ggc | 288 |
| Glu | Glu | Ile | Asn | Asn | Gly | Ser | Ala | Leu | Leu | Pro | Gly | Leu | Arg | Leu | Gly | |
| | | | | 85 | | | | | 90 | | | | | 95 | | |
| tat | gac | cta | ttt | gac | aca | tgc | tcc | gag | cca | gtg | gtc | acc | atg | aaa | tcc | 336 |
| Tyr | Asp | Leu | Phe | Asp | Thr | Cys | Ser | Glu | Pro | Val | Val | Thr | Met | Lys | Ser | |
| | | | 100 | | | | | 105 | | | | | 110 | | | |
| agt | ctc | atg | ttc | ctg | gcc | aag | gtg | ggc | agt | caa | agc | att | gct | gcc | tac | 384 |
| Ser | Leu | Met | Phe | Leu | Ala | Lys | Val | Gly | Ser | Gln | Ser | Ile | Ala | Ala | Tyr | |
| | | 115 | | | | | 120 | | | | | 125 | | | | |
| tgc | aac | tac | aca | cag | tac | caa | ccc | cgt | gtg | ctg | gct | gtc | atc | ggc | ccc | 432 |
| Cys | Asn | Tyr | Thr | Gln | Tyr | Gln | Pro | Arg | Val | Leu | Ala | Val | Ile | Gly | Pro | |
| | 130 | | | | | 135 | | | | | 140 | | | | | |
| cac | tca | tca | gag | ctt | gcc | ctc | att | aca | ggc | aag | ttc | ttc | agc | ttc | ttc | 480 |
| His | Ser | Ser | Glu | Leu | Ala | Leu | Ile | Thr | Gly | Lys | Phe | Phe | Ser | Phe | Phe | |
| 145 | | | | | 150 | | | | | 155 | | | | | 160 | |
| ctc | atg | cca | cag | gtc | agc | tat | agt | gcc | agc | atg | gat | cgg | cta | agt | gac | 528 |
| Leu | Met | Pro | Gln | Val | Ser | Tyr | Ser | Ala | Ser | Met | Asp | Arg | Leu | Ser | Asp | |
| | | | | 165 | | | | | 170 | | | | | 175 | | |
| cgg | gaa | acg | ttt | cca | tcc | ttc | ttc | cgc | aca | gtg | ccc | agt | gac | cgg | gtg | 576 |
| Arg | Glu | Thr | Phe | Pro | Ser | Phe | Phe | Arg | Thr | Val | Pro | Ser | Asp | Arg | Val | |
| | | | 180 | | | | | 185 | | | | | 190 | | | |
| cag | ctg | cag | gca | gtt | gtg | act | ctg | ttg | cag | aac | ttc | agc | tgg | aac | tgg | 624 |
| Gln | Leu | Gln | Ala | Val | Val | Thr | Leu | Leu | Gln | Asn | Phe | Ser | Trp | Asn | Trp | |
| | | 195 | | | | | 200 | | | | | 205 | | | | |
| gtg | gcc | gcc | tta | ggg | agt | gat | gat | gac | tat | ggc | cgg | gaa | ggt | ctg | agc | 672 |
| Val | Ala | Ala | Leu | Gly | Ser | Asp | Asp | Asp | Tyr | Gly | Arg | Glu | Gly | Leu | Ser | |
| | 210 | | | | | 215 | | | | | 220 | | | | | |
| atc | ttt | tct | agt | ctg | gcc | aat | gca | cga | ggt | atc | tgc | atc | gca | cat | gag | 720 |

|  |  |  |  |  |  |  |  |  |  |  |  |  |  |  |
|---|---|---|---|---|---|---|---|---|---|---|---|---|---|---|
| Ile | Phe | Ser | Ser | Leu | Ala | Asn | Ala | Arg | Gly | Ile | Cys | Ile | Ala | His | Glu |
| 225 |  |  |  |  | 230 |  |  |  |  | 235 |  |  |  |  | 240 |

```
ggc ctg gtg cca caa cat gac act agt ggc caa cag ttg ggc aag gtg       768
Gly Leu Val Pro Gln His Asp Thr Ser Gly Gln Gln Leu Gly Lys Val
                    245                 250                 255 ctg gat gta cta cgc caa gtg aac caa agt aaa gta caa gtg gtg gtg       816
Leu Asp Val Leu Arg Gln Val Asn Gln Ser Lys Val Gln Val Val Val
                260                 265                 270 ctg ttt gcc tct gcc cgt gct gtc tac tcc ctt ttt agt tac agc atc       864
Leu Phe Ala Ser Ala Arg Ala Val Tyr Ser Leu Phe Ser Tyr Ser Ile
            275                 280                 285 cat cat ggc ctc tca ccc aag gta tgg gtg gcc agt gag tct tgg ctg       912
His His Gly Leu Ser Pro Lys Val Trp Val Ala Ser Glu Ser Trp Leu
        290                 295                 300 aca tct gac ctg gtc atg aca ctt ccc aat att gcc cgt gtg ggc act       960
Thr Ser Asp Leu Val Met Thr Leu Pro Asn Ile Ala Arg Val Gly Thr
305                 310                 315                 320 gtg ctt ggg ttt ttg cag cgg ggt gcc cta ctg cct gaa ttt tcc cat      1008
Val Leu Gly Phe Leu Gln Arg Gly Ala Leu Leu Pro Glu Phe Ser His
                325                 330                 335 tat gtg gag act cac ctt gcc ctg gcc gct gac cca gca ttc tgt gcc      1056
Tyr Val Glu Thr His Leu Ala Leu Ala Ala Asp Pro Ala Phe Cys Ala
                340                 345                 350 tca ctg aat gcg gag ttg gat ctg gag gaa cat gtg atg ggg caa cgc      1104
Ser Leu Asn Ala Glu Leu Asp Leu Glu Glu His Val Met Gly Gln Arg
            355                 360                 365 tgt cca cgg tgt gac gac atc atg ctg cag aac cta tca tct ggg ctg      1152
Cys Pro Arg Cys Asp Asp Ile Met Leu Gln Asn Leu Ser Ser Gly Leu
        370                 375                 380 ttg cag aac cta tca gct ggg caa ttg cac cac caa ata ttt gca acc      1200
Leu Gln Asn Leu Ser Ala Gly Gln Leu His His Gln Ile Phe Ala Thr
385                 390                 395                 400 tat gca gct gtg tac agt gtg gct caa gcc ctt cac aac acc cta cag      1248
Tyr Ala Ala Val Tyr Ser Val Ala Gln Ala Leu His Asn Thr Leu Gln
                405                 410                 415 tgc aat gtc tca cat tgc cac gta tca gaa cat gtt cta ccc tgg cag      1296
Cys Asn Val Ser His Cys His Val Ser Glu His Val Leu Pro Trp Gln
                420                 425                 430 ctc ctg gag aac atg tac aat atg agt ttc cat gct cga gac ttg aca      1344
Leu Leu Glu Asn Met Tyr Asn Met Ser Phe His Ala Arg Asp Leu Thr
            435                 440                 445 cta cag ttt gat gct gaa ggg aat gta gac atg gaa tat gac ctg aag      1392
Leu Gln Phe Asp Ala Glu Gly Asn Val Asp Met Glu Tyr Asp Leu Lys
        450                 455                 460 atg tgg gtg tgg cag agc cct aca cct gta tta cat act gtg ggc acc      1440
Met Trp Val Trp Gln Ser Pro Thr Pro Val Leu His Thr Val Gly Thr
465                 470                 475                 480 ttc aac ggc acc ctt cag ctg cag cag tct aaa atg tac tgg cca ggc      1488
Phe Asn Gly Thr Leu Gln Leu Gln Gln Ser Lys Met Tyr Trp Pro Gly
                485                 490                 495 aac cag gtg cca gtc tcc cag tgt tcc cgc cag tgc aaa gat ggc cag      1536
Asn Gln Val Pro Val Ser Gln Cys Ser Arg Gln Cys Lys Asp Gly Gln
                500                 505                 510 gtt cgc cga gta aag ggc ttt cat tcc tgc tgt tat gac tgc gtg gac      1584
Val Arg Arg Val Lys Gly Phe His Ser Cys Cys Tyr Asp Cys Val Asp
            515                 520                 525 tgc aag gcg ggc agc tac cgg aag cat cca gac gac atc gcc tgc acc      1632
Cys Lys Ala Gly Ser Tyr Arg Lys His Pro Asp Asp Ile Ala Cys Thr
        530                 535                 540
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| ttt | tgt | ggc | cag | gat | gag | tgg | tcc | ccg | gag | cga | agc | aca | cgc | tgc | ttc | 1680 |
| Phe | Cys | Gly | Gln | Asp | Glu | Trp | Ser | Pro | Glu | Arg | Ser | Thr | Arg | Cys | Phe |      |
| 545 |     |     |     | 550 |     |     |     |     | 555 |     |     |     |     | 560 |     |      |

|     |     |     |     |     |     |     |     |     |     |     |     |     |     |     |      |
| --- | --- | --- | --- | --- | --- | --- | --- | --- | --- | --- | --- | --- | --- | --- | ---- |
| cgc | cgc | agg | tct | cgg | ttc | ctg | gca | tgg | ggc | gag | ccg | gct | gtg | ctg | 1728 |
| Arg | Arg | Arg | Ser | Arg | Phe | Leu | Ala | Trp | Gly | Glu | Pro | Ala | Val | Leu |      |
|     |     |     |     | 565 |     |     |     |     | 570 |     |     |     |     | 575 |      |

|     |     |     |     |     |     |     |     |     |     |     |     |     |     |     |      |
| --- | --- | --- | --- | --- | --- | --- | --- | --- | --- | --- | --- | --- | --- | --- | ---- |
| ctg | ctc | ctg | ctg | ctg | agc | ctg | gcg | ctg | ggc | ctt | gtg | ctg | gct | gct | ttg | 1776 |
| Leu | Leu | Leu | Leu | Leu | Ser | Leu | Ala | Leu | Gly | Leu | Val | Leu | Ala | Ala | Leu |      |
|     |     |     |     | 580 |     |     |     |     | 585 |     |     |     |     | 590 |     |      |

|     |     |     |     |     |     |     |     |     |     |     |     |     |     |     |      |
| --- | --- | --- | --- | --- | --- | --- | --- | --- | --- | --- | --- | --- | --- | --- | ---- |
| ggg | ctg | ttc | gtt | cac | cat | cgg | gac | agc | cca | ctg | gtt | cag | gcc | tcg | ggg | 1824 |
| Gly | Leu | Phe | Val | His | His | Arg | Asp | Ser | Pro | Leu | Val | Gln | Ala | Ser | Gly |      |
|     |     |     | 595 |     |     |     |     | 600 |     |     |     |     | 605 |     |     |      |

|     |     |     |     |     |     |     |     |     |     |     |     |     |     |     |      |
| --- | --- | --- | --- | --- | --- | --- | --- | --- | --- | --- | --- | --- | --- | --- | ---- |
| ggg | ccc | ctg | gcc | tgc | ttt | ggc | ctg | gtg | tgc | ctg | ggc | ctg | gtc | tgc | ctc | 1872 |
| Gly | Pro | Leu | Ala | Cys | Phe | Gly | Leu | Val | Cys | Leu | Gly | Leu | Val | Cys | Leu |      |
|     |     | 610 |     |     |     |     | 615 |     |     |     |     | 620 |     |     |     |      |

|     |     |     |     |     |     |     |     |     |     |     |     |     |     |     |      |
| --- | --- | --- | --- | --- | --- | --- | --- | --- | --- | --- | --- | --- | --- | --- | ---- |
| agc | gtc | ctc | ctg | ttc | cct | ggc | cag | ccc | agc | cct | gcc | cga | tgc | ctg | gcc | 1920 |
| Ser | Val | Leu | Leu | Phe | Pro | Gly | Gln | Pro | Ser | Pro | Ala | Arg | Cys | Leu | Ala |      |
| 625 |     |     |     |     | 630 |     |     |     |     | 635 |     |     |     |     | 640 |      |

|     |     |     |     |     |     |     |     |     |     |     |     |     |     |     |      |
| --- | --- | --- | --- | --- | --- | --- | --- | --- | --- | --- | --- | --- | --- | --- | ---- |
| cag | cag | ccc | ttg | tcc | cac | ctc | ccg | ctc | acg | ggc | tgc | ctg | agc | aca | ctc | 1968 |
| Gln | Gln | Pro | Leu | Ser | His | Leu | Pro | Leu | Thr | Gly | Cys | Leu | Ser | Thr | Leu |      |
|     |     |     |     |     | 645 |     |     |     |     | 650 |     |     |     |     | 655 |      |

|     |     |     |     |     |     |     |     |     |     |     |     |     |     |     |      |
| --- | --- | --- | --- | --- | --- | --- | --- | --- | --- | --- | --- | --- | --- | --- | ---- |
| ttc | ctg | cag | gcg | gcc | gag | atc | ttc | gtg | gag | tca | gaa | ctg | cct | ctg | agc | 2016 |
| Phe | Leu | Gln | Ala | Ala | Glu | Ile | Phe | Val | Glu | Ser | Glu | Leu | Pro | Leu | Ser |      |
|     |     |     |     | 660 |     |     |     |     | 665 |     |     |     |     | 670 |     |      |

|     |     |     |     |     |     |     |     |     |     |     |     |     |     |     |      |
| --- | --- | --- | --- | --- | --- | --- | --- | --- | --- | --- | --- | --- | --- | --- | ---- |
| tgg | gca | gac | cgg | ctg | agt | ggc | tgc | ctg | cgg | ggg | ccc | tgg | gcc | tgg | ctg | 2064 |
| Trp | Ala | Asp | Arg | Leu | Ser | Gly | Cys | Leu | Arg | Gly | Pro | Trp | Ala | Trp | Leu |      |
|     |     |     | 675 |     |     |     |     | 680 |     |     |     |     | 685 |     |     |      |

|     |     |     |     |     |     |     |     |     |     |     |     |     |     |     |      |
| --- | --- | --- | --- | --- | --- | --- | --- | --- | --- | --- | --- | --- | --- | --- | ---- |
| gtg | gtg | ctg | ctg | gcc | atg | ctg | gtg | gag | gtc | gca | ctg | tgc | acc | tgg | tac | 2112 |
| Val | Val | Leu | Leu | Ala | Met | Leu | Val | Glu | Val | Ala | Leu | Cys | Thr | Trp | Tyr |      |
|     | 690 |     |     |     |     | 695 |     |     |     |     | 700 |     |     |     |     |      |

|     |     |     |     |     |     |     |     |     |     |     |     |     |     |     |      |
| --- | --- | --- | --- | --- | --- | --- | --- | --- | --- | --- | --- | --- | --- | --- | ---- |
| ctg | gtg | gcc | ttc | ccg | ccg | gag | gtg | gtg | acg | gac | tgg | cac | atg | ctg | ccc | 2160 |
| Leu | Val | Ala | Phe | Pro | Pro | Glu | Val | Val | Thr | Asp | Trp | His | Met | Leu | Pro |      |
| 705 |     |     |     |     | 710 |     |     |     |     | 715 |     |     |     |     | 720 |      |

|     |     |     |     |     |     |     |     |     |     |     |     |     |     |     |      |
| --- | --- | --- | --- | --- | --- | --- | --- | --- | --- | --- | --- | --- | --- | --- | ---- |
| acg | gag | gcg | ctg | gtg | cac | tgc | cgc | aca | cgc | tcc | tgg | gtc | agc | ttc | ggc | 2208 |
| Thr | Glu | Ala | Leu | Val | His | Cys | Arg | Thr | Arg | Ser | Trp | Val | Ser | Phe | Gly |      |
|     |     |     |     |     | 725 |     |     |     |     | 730 |     |     |     |     | 735 |      |

|     |     |     |     |     |     |     |     |     |     |     |     |     |     |     |      |
| --- | --- | --- | --- | --- | --- | --- | --- | --- | --- | --- | --- | --- | --- | --- | ---- |
| cta | gcg | cac | gcc | acc | aat | gcc | acg | ctg | gcc | ttt | ctc | tgc | ttc | ctg | ggc | 2256 |
| Leu | Ala | His | Ala | Thr | Asn | Ala | Thr | Leu | Ala | Phe | Leu | Cys | Phe | Leu | Gly |      |
|     |     |     |     | 740 |     |     |     |     | 745 |     |     |     |     | 750 |     |      |

|     |     |     |     |     |     |     |     |     |     |     |     |     |     |     |      |
| --- | --- | --- | --- | --- | --- | --- | --- | --- | --- | --- | --- | --- | --- | --- | ---- |
| act | ttc | ctg | gtg | cgg | agc | cag | ccg | ggc | cgc | tac | aac | cgt | gcc | cgt | ggc | 2304 |
| Thr | Phe | Leu | Val | Arg | Ser | Gln | Pro | Gly | Arg | Tyr | Asn | Arg | Ala | Arg | Gly |      |
|     |     | 755 |     |     |     |     | 760 |     |     |     |     | 765 |     |     |     |      |

|     |     |     |     |     |     |     |     |     |     |     |     |     |     |     |      |
| --- | --- | --- | --- | --- | --- | --- | --- | --- | --- | --- | --- | --- | --- | --- | ---- |
| ctc | acc | ttt | gcc | atg | ctg | gcc | tac | ttc | atc | acc | tgg | gtc | tcc | ttt | gtg | 2352 |
| Leu | Thr | Phe | Ala | Met | Leu | Ala | Tyr | Phe | Ile | Thr | Trp | Val | Ser | Phe | Val |      |
|     |     | 770 |     |     |     |     | 775 |     |     |     |     | 780 |     |     |     |      |

|     |     |     |     |     |     |     |     |     |     |     |     |     |     |     |      |
| --- | --- | --- | --- | --- | --- | --- | --- | --- | --- | --- | --- | --- | --- | --- | ---- |
| ccc | ctc | ctg | gcc | aat | gtg | cag | gtg | gtc | ctc | agg | ccc | gcc | gtg | cag | atg | 2400 |
| Pro | Leu | Leu | Ala | Asn | Val | Gln | Val | Val | Leu | Arg | Pro | Ala | Val | Gln | Met |      |
| 785 |     |     |     |     | 790 |     |     |     |     | 795 |     |     |     |     | 800 |      |

|     |     |     |     |     |     |     |     |     |     |     |     |     |     |     |      |
| --- | --- | --- | --- | --- | --- | --- | --- | --- | --- | --- | --- | --- | --- | --- | ---- |
| ggc | gcc | ctc | ctg | ctc | tgt | gtc | ctg | ggc | atc | ctg | gct | gcc | ttc | cac | ctg | 2448 |
| Gly | Ala | Leu | Leu | Leu | Cys | Val | Leu | Gly | Ile | Leu | Ala | Ala | Phe | His | Leu |      |
|     |     |     |     | 805 |     |     |     |     | 810 |     |     |     |     | 815 |     |      |

|     |     |     |     |     |     |     |     |     |     |     |     |     |     |     |      |
| --- | --- | --- | --- | --- | --- | --- | --- | --- | --- | --- | --- | --- | --- | --- | ---- |
| ccc | agg | tgt | tac | ctg | ctc | atg | cgg | cag | cca | ggg | ctc | aac | acc | ccc | gag | 2496 |
| Pro | Arg | Cys | Tyr | Leu | Leu | Met | Arg | Gln | Pro | Gly | Leu | Asn | Thr | Pro | Glu |      |
|     |     |     | 820 |     |     |     |     | 825 |     |     |     |     | 830 |     |     |      |

|     |     |     |     |     |     |     |     |     |     |     |     |     |     |     |      |
| --- | --- | --- | --- | --- | --- | --- | --- | --- | --- | --- | --- | --- | --- | --- | ---- |
| ttc | ttc | ctg | gga | ggg | ggc | cct | ggg | gat | gcc | caa | ggc | cag | aat | gac | ggg | 2544 |
| Phe | Phe | Leu | Gly | Gly | Gly | Pro | Gly | Asp | Ala | Gln | Gly | Gln | Asn | Asp | Gly |      |
|     |     | 835 |     |     |     |     | 840 |     |     |     |     | 845 |     |     |     |      |

|     |     |     |     |     |     |     |     |      |
| --- | --- | --- | --- | --- | --- | --- | --- | ---- |
| aac | aca | gga | aat | cag | ggg | aaa | cat | gag tga | 2574 |
| Asn | Thr | Gly | Asn | Gln | Gly | Lys | His | Glu |      |
| 850 |     |     |     |     | 855 |     |     |     |      |

<210> SEQ ID NO 30
<211> LENGTH: 857
<212> TYPE: PRT
<213> ORGANISM: Artificial Sequence
<220> FEATURE:
<223> OTHER INFORMATION: chimeric protein

<400> SEQUENCE: 30

```
Met Leu Gly Pro Ala Val Leu Gly Leu Ser Leu Trp Ala Leu Leu His
  1               5                  10                  15
Pro Gly Thr Gly Ala Pro Leu Cys Leu Ser Gln Gln Leu Arg Met Lys
             20                  25                  30
Gly Asp Tyr Val Leu Gly Gly Leu Phe Pro Leu Gly Glu Ala Glu Glu
         35                  40                  45
Ala Gly Leu Arg Ser Arg Thr Arg Pro Ser Ser Pro Val Cys Thr Arg
     50                  55                  60
Phe Ser Pro Leu Gly Leu Phe Leu Ala Met Ala Met Lys Met Ala Val
 65                  70                  75                  80
Glu Glu Ile Asn Asn Gly Ser Ala Leu Leu Pro Gly Leu Arg Leu Gly
                 85                  90                  95
Tyr Asp Leu Phe Asp Thr Cys Ser Glu Pro Val Val Thr Met Lys Ser
            100                 105                 110
Ser Leu Met Phe Leu Ala Lys Val Gly Ser Gln Ser Ile Ala Ala Tyr
        115                 120                 125
Cys Asn Tyr Thr Gln Tyr Gln Pro Arg Val Leu Ala Val Ile Gly Pro
    130                 135                 140
His Ser Ser Glu Leu Ala Leu Ile Thr Gly Lys Phe Phe Ser Phe Phe
145                 150                 155                 160
Leu Met Pro Gln Val Ser Tyr Ser Ala Ser Met Asp Arg Leu Ser Asp
                165                 170                 175
Arg Glu Thr Phe Pro Ser Phe Phe Arg Thr Val Pro Ser Asp Arg Val
            180                 185                 190
Gln Leu Gln Ala Val Val Thr Leu Leu Gln Asn Phe Ser Trp Asn Trp
        195                 200                 205
Val Ala Ala Leu Gly Ser Asp Asp Asp Tyr Gly Arg Glu Gly Leu Ser
    210                 215                 220
Ile Phe Ser Ser Leu Ala Asn Ala Arg Gly Ile Cys Ile Ala His Glu
225                 230                 235                 240
Gly Leu Val Pro Gln His Asp Thr Ser Gly Gln Gln Leu Gly Lys Val
                245                 250                 255
Leu Asp Val Leu Arg Gln Val Asn Gln Ser Lys Val Gln Val Val Val
            260                 265                 270
Leu Phe Ala Ser Ala Arg Ala Val Tyr Ser Leu Phe Ser Tyr Ser Ile
        275                 280                 285
His His Gly Leu Ser Pro Lys Val Trp Val Ala Ser Glu Ser Trp Leu
    290                 295                 300
Thr Ser Asp Leu Val Met Thr Leu Pro Asn Ile Ala Arg Val Gly Thr
305                 310                 315                 320
Val Leu Gly Phe Leu Gln Arg Gly Ala Leu Leu Pro Glu Phe Ser His
                325                 330                 335
Tyr Val Glu Thr His Leu Ala Leu Ala Ala Asp Pro Ala Phe Cys Ala
            340                 345                 350
Ser Leu Asn Ala Glu Leu Asp Leu Glu Glu His Val Met Gly Gln Arg
        355                 360                 365
```

-continued

Cys Pro Arg Cys Asp Asp Ile Met Leu Gln Asn Leu Ser Ser Gly Leu
    370                 375                 380

Leu Gln Asn Leu Ser Ala Gly Gln Leu His His Gln Ile Phe Ala Thr
385                 390                 395                 400

Tyr Ala Ala Val Tyr Ser Val Ala Gln Ala Leu His Asn Thr Leu Gln
                405                 410                 415

Cys Asn Val Ser His Cys His Val Ser Glu His Val Leu Pro Trp Gln
                420                 425                 430

Leu Leu Glu Asn Met Tyr Asn Met Ser Phe His Ala Arg Asp Leu Thr
            435                 440                 445

Leu Gln Phe Asp Ala Glu Gly Asn Val Asp Met Glu Tyr Asp Leu Lys
    450                 455                 460

Met Trp Val Trp Gln Ser Pro Thr Pro Val Leu His Thr Val Gly Thr
465                 470                 475                 480

Phe Asn Gly Thr Leu Gln Leu Gln Gln Ser Lys Met Tyr Trp Pro Gly
                485                 490                 495

Asn Gln Val Pro Val Ser Gln Cys Ser Arg Gln Cys Lys Asp Gly Gln
                500                 505                 510

Val Arg Arg Val Lys Gly Phe His Ser Cys Cys Tyr Asp Cys Val Asp
    515                 520                 525

Cys Lys Ala Gly Ser Tyr Arg Lys His Pro Asp Asp Ile Ala Cys Thr
    530                 535                 540

Phe Cys Gly Gln Asp Glu Trp Ser Pro Glu Arg Ser Thr Arg Cys Phe
545                 550                 555                 560

Arg Arg Arg Ser Arg Phe Leu Ala Trp Gly Glu Pro Ala Val Leu Leu
                565                 570                 575

Leu Leu Leu Leu Leu Ser Leu Ala Leu Gly Leu Val Leu Ala Ala Leu
            580                 585                 590

Gly Leu Phe Val His His Arg Asp Ser Pro Leu Val Gln Ala Ser Gly
    595                 600                 605

Gly Pro Leu Ala Cys Phe Gly Leu Val Cys Leu Gly Leu Val Cys Leu
610                 615                 620

Ser Val Leu Leu Phe Pro Gly Gln Pro Ser Pro Ala Arg Cys Leu Ala
625                 630                 635                 640

Gln Gln Pro Leu Ser His Leu Pro Leu Thr Gly Cys Leu Ser Thr Leu
                645                 650                 655

Phe Leu Gln Ala Ala Glu Ile Phe Val Glu Ser Glu Leu Pro Leu Ser
            660                 665                 670

Trp Ala Asp Arg Leu Ser Gly Cys Leu Arg Gly Pro Trp Ala Trp Leu
    675                 680                 685

Val Val Leu Leu Ala Met Leu Val Glu Val Ala Leu Cys Thr Trp Tyr
690                 695                 700

Leu Val Ala Phe Pro Pro Glu Val Val Thr Asp Trp His Met Leu Pro
705                 710                 715                 720

Thr Glu Ala Leu Val His Cys Arg Thr Arg Ser Trp Val Ser Phe Gly
                725                 730                 735

Leu Ala His Ala Thr Asn Ala Thr Leu Ala Phe Leu Cys Phe Leu Gly
            740                 745                 750

Thr Phe Leu Val Arg Ser Gln Pro Gly Arg Tyr Asn Arg Ala Arg Gly
    755                 760                 765

Leu Thr Phe Ala Met Leu Ala Tyr Phe Ile Thr Trp Val Ser Phe Val
    770                 775                 780

```
Pro Leu Leu Ala Asn Val Gln Val Val Leu Arg Pro Ala Val Gln Met
785                 790                 795                 800

Gly Ala Leu Leu Leu Cys Val Leu Gly Ile Leu Ala Ala Phe His Leu
            805                 810                 815

Pro Arg Cys Tyr Leu Leu Met Arg Gln Pro Gly Leu Asn Thr Pro Glu
        820                 825                 830

Phe Phe Leu Gly Gly Gly Pro Gly Asp Ala Gln Gly Gln Asn Asp Gly
            835                 840                 845

Asn Thr Gly Asn Gln Gly Lys His Glu
    850                 855
```

<210> SEQ ID NO 31
<211> LENGTH: 44
<212> TYPE: DNA
<213> ORGANISM: Artificial Sequence
<220> FEATURE:
<223> OTHER INFORMATION: primer

<400> SEQUENCE: 31
tagcgtttaa acttaagctt ccaccatgcc agctttggct atca          44

<210> SEQ ID NO 32
<211> LENGTH: 23
<212> TYPE: DNA
<213> ORGANISM: Artificial Sequence
<220> FEATURE:
<223> OTHER INFORMATION: primer

<400> SEQUENCE: 32
ggagaacctg ttgcacggga tgc                                 23

<210> SEQ ID NO 33
<211> LENGTH: 27
<212> TYPE: DNA
<213> ORGANISM: Artificial Sequence
<220> FEATURE:
<223> OTHER INFORMATION: primer

<400> SEQUENCE: 33
tgcaacaggt tctcctcaaa cggcctg                             27

<210> SEQ ID NO 34
<211> LENGTH: 27
<212> TYPE: DNA
<213> ORGANISM: Artificial Sequence
<220> FEATURE:
<223> OTHER INFORMATION: primer

<400> SEQUENCE: 34
gcatgaggaa gaagctgaag aacttgc                             27

<210> SEQ ID NO 35
<211> LENGTH: 27
<212> TYPE: DNA
<213> ORGANISM: Artificial Sequence
<220> FEATURE:
<223> OTHER INFORMATION: primer

<400> SEQUENCE: 35
gcaagttctt cagcttcttc ctcatgc                             27

<210> SEQ ID NO 36
<211> LENGTH: 2574
<212> TYPE: DNA

```
<213> ORGANISM: Artificial Sequence
<220> FEATURE:
<223> OTHER INFORMATION: chimeric gene
<220> FEATURE:
<221> NAME/KEY: CDS
<222> LOCATION: (1)..(2574)

<400> SEQUENCE: 36 atg cca gct ttg gct atc atg ggt ctc agc ctg gct gct ttc ctg gag      48
Met Pro Ala Leu Ala Ile Met Gly Leu Ser Leu Ala Ala Phe Leu Glu
1               5                   10                  15 ctt ggg atg ggg gcc tct ttg tgt ctg tca cag caa ttc aag gca caa      96
Leu Gly Met Gly Ala Ser Leu Cys Leu Ser Gln Gln Phe Lys Ala Gln
            20                  25                  30 ggg gac tac ata ctg ggc ggg cta ttt ccc ctg gca tca acc gag gag     144
Gly Asp Tyr Ile Leu Gly Gly Leu Phe Pro Leu Gly Ser Thr Glu Glu
        35                  40                  45 gcc act ctc aac cag aga aca caa ccc aac agc atc ccg tgc aac agg     192
Ala Thr Leu Asn Gln Arg Thr Gln Pro Asn Ser Ile Pro Cys Asn Arg
    50                  55                  60 ttc tcc tca aac ggc ctg ctc tgg gca ctg gcc atg aaa atg gcc gtg     240
Phe Ser Ser Asn Gly Leu Leu Trp Ala Leu Ala Met Lys Met Ala Val
65                  70                  75                  80 gag gag atc aac aac aag tcg gat ctg ctc ccc ggg ctg cgc ctg ggc     288
Glu Glu Ile Asn Asn Lys Ser Asp Leu Leu Pro Gly Leu Arg Leu Gly
                85                  90                  95 tac gac ctc ttt gat acg tgc tcg gag cct gtg gtg gcc atg aag ccc     336
Tyr Asp Leu Phe Asp Thr Cys Ser Glu Pro Val Val Ala Met Lys Pro
            100                 105                 110 agc ctc atg ttc ctg gcc aag gca ggc agc cgc gac atc gcc gcc tac     384
Ser Leu Met Phe Leu Ala Lys Ala Gly Ser Arg Asp Ile Ala Ala Tyr
        115                 120                 125 tgc aac tac acg cag tac cag ccc cgt gtg ctg gct gtc atc ggg ccc     432
Cys Asn Tyr Thr Gln Tyr Gln Pro Arg Val Leu Ala Val Ile Gly Pro
    130                 135                 140 cac tcg tca gag ctc gcc atg gtc acc ggc aag ttc ttc agc ttc ttc     480
His Ser Ser Glu Leu Ala Met Val Thr Gly Lys Phe Phe Ser Phe Phe
145                 150                 155                 160 ctc atg cca cag gtc agc tat agt gcc agc atg gat cgg cta agt gac     528
Leu Met Pro Gln Val Ser Tyr Ser Ala Ser Met Asp Arg Leu Ser Asp
                165                 170                 175 cgg gaa acg ttt cca tcc ttc ttc cgc aca gtg ccc agt gac cgg gtg     576
Arg Glu Thr Phe Pro Ser Phe Phe Arg Thr Val Pro Ser Asp Arg Val
            180                 185                 190 cag ctg cag gca gtt gtg act ctg ttg cag aac ttc agc tgg aac tgg     624
Gln Leu Gln Ala Val Val Thr Leu Leu Gln Asn Phe Ser Trp Asn Trp
        195                 200                 205 gtg gcc gcc tta ggg agt gat gat gac tat ggc cgg gaa ggt ctg agc     672
Val Ala Ala Leu Gly Ser Asp Asp Asp Tyr Gly Arg Glu Gly Leu Ser
    210                 215                 220 atc ttt tct agt ctg gcc aat gca cga ggt atc tgc atc gca cat gag     720
Ile Phe Ser Ser Leu Ala Asn Ala Arg Gly Ile Cys Ile Ala His Glu
225                 230                 235                 240 ggc ctg gtg cca caa cat gac act agt ggc caa cag ttg ggc aag gtg     768
Gly Leu Val Pro Gln His Asp Thr Ser Gly Gln Gln Leu Gly Lys Val
                245                 250                 255 ctg gat gta cta cgc caa gtg aac caa agt aaa gta caa gtg gtg gtg     816
Leu Asp Val Leu Arg Gln Val Asn Gln Ser Lys Val Gln Val Val Val
            260                 265                 270 ctg ttt gcc tct gcc cgt gct gtc tac tcc ctt ttt agt tac agc atc     864
Leu Phe Ala Ser Ala Arg Ala Val Tyr Ser Leu Phe Ser Tyr Ser Ile
```

-continued

|  | 275 |  |  | 280 |  |  | 285 |  |  |  |
|---|---|---|---|---|---|---|---|---|---|---|
| cat | cat | ggc | ctc | tca | ccc | aag | gta | tgg | gtg | gcc | agt | gag | tct | tgg | ctg | 912 |
| His | His | Gly | Leu | Ser | Pro | Lys | Val | Trp | Val | Ala | Ser | Glu | Ser | Trp | Leu |  |
|  | 290 |  |  | 295 |  |  | 300 |  |  |  |

```
cat cat ggc ctc tca ccc aag gta tgg gtg gcc agt gag tct tgg ctg      912
His His Gly Leu Ser Pro Lys Val Trp Val Ala Ser Glu Ser Trp Leu
    290              295              300 aca tct gac ctg gtc atg aca ctt ccc aat att gcc cgt gtg ggc act      960
Thr Ser Asp Leu Val Met Thr Leu Pro Asn Ile Ala Arg Val Gly Thr
305              310              315              320 gtg ctt ggg ttt ttg cag cgg ggt gcc cta ctg cct gaa ttt tcc cat     1008
Val Leu Gly Phe Leu Gln Arg Gly Ala Leu Leu Pro Glu Phe Ser His
                325              330              335 tat gtg gag act cac ctt gcc ctg gcc gct gac cca gca ttc tgt gcc     1056
Tyr Val Glu Thr His Leu Ala Leu Ala Ala Asp Pro Ala Phe Cys Ala
        340              345              350 tca ctg aat gcg gag ttg gat ctg gag gaa cat gtg atg ggg caa cgc     1104
Ser Leu Asn Ala Glu Leu Asp Leu Glu Glu His Val Met Gly Gln Arg
355              360              365 tgt cca cgg tgt gac gac atc atg ctg cag aac cta tca tct ggg ctg     1152
Cys Pro Arg Cys Asp Asp Ile Met Leu Gln Asn Leu Ser Ser Gly Leu
    370              375              380 ttg cag aac cta tca gct ggg caa ttg cac cac caa ata ttt gca acc     1200
Leu Gln Asn Leu Ser Ala Gly Gln Leu His His Gln Ile Phe Ala Thr
385              390              395              400 tat gca gct gtg tac agt gtg gct caa gcc ctt cac aac acc cta cag     1248
Tyr Ala Ala Val Tyr Ser Val Ala Gln Ala Leu His Asn Thr Leu Gln
                405              410              415 tgc aat gtc tca cat tgc cac gta tca gaa cat gtt cta ccc tgg cag     1296
Cys Asn Val Ser His Cys His Val Ser Glu His Val Leu Pro Trp Gln
        420              425              430 ctc ctg gag aac atg tac aat atg agt ttc cat gct cga gac ttg aca     1344
Leu Leu Glu Asn Met Tyr Asn Met Ser Phe His Ala Arg Asp Leu Thr
435              440              445 cta cag ttt gat gct gaa ggg aat gta gac atg gaa tat gac ctg aag     1392
Leu Gln Phe Asp Ala Glu Gly Asn Val Asp Met Glu Tyr Asp Leu Lys
450              455              460 atg tgg gtg tgg cag agc cct aca cct gta tta cat act gtg ggc acc     1440
Met Trp Val Trp Gln Ser Pro Thr Pro Val Leu His Thr Val Gly Thr
465              470              475              480 ttc aac ggc acc ctt cag ctg cag cag tct aaa atg tac tgg cca ggc     1488
Phe Asn Gly Thr Leu Gln Leu Gln Gln Ser Lys Met Tyr Trp Pro Gly
                485              490              495 aac cag gtg cca gtc tcc cag tgt tcc cgc cag tgc aaa gat ggc cag     1536
Asn Gln Val Pro Val Ser Gln Cys Ser Arg Gln Cys Lys Asp Gly Gln
        500              505              510 gtt cgc cga gta aag ggc ttt cat tcc tgc tgc tat gac tgc gtg gac     1584
Val Arg Arg Val Lys Gly Phe His Ser Cys Cys Tyr Asp Cys Val Asp
                515              520              525 tgc aag gcg ggc agc tac cgg aag cat cca gac gac atc gcc tgc acc     1632
Cys Lys Ala Gly Ser Tyr Arg Lys His Pro Asp Asp Ile Ala Cys Thr
530              535              540 ttt tgt ggc cag gat gag tgg tcc ccg gag cga agc aca cgc tgc ttc     1680
Phe Cys Gly Gln Asp Glu Trp Ser Pro Glu Arg Ser Thr Arg Cys Phe
545              550              555              560 cgc cgc agg tct cgg ttc ctg gca tgg ggc gag ccg gct gtg ctg ctg     1728
Arg Arg Arg Ser Arg Phe Leu Ala Trp Gly Glu Pro Ala Val Leu Leu
                565              570              575 ctg ctc ctg ctg ctg agc ctg gcg ctg ggc ctt gtg ctg gct gct ttg     1776
Leu Leu Leu Leu Leu Ser Leu Ala Leu Gly Leu Val Leu Ala Ala Leu
        580              585              590 ggg ctg ttc gtt cac cat cgg gac agc cca ctg gtt cag gcc tcg ggg     1824
```

```
Gly Leu Phe Val His His Arg Asp Ser Pro Leu Val Gln Ala Ser Gly
            595                 600                 605 ggg ccc ctg gcc tgc ttt ggc ctg gtg tgc ctg ggc ctg gtc tgc ctc    1872
Gly Pro Leu Ala Cys Phe Gly Leu Val Cys Leu Gly Leu Val Cys Leu
610                 615                 620 agc gtc ctc ctg ttc cct ggc cag ccc agc cct gcc cga tgc ctg gcc    1920
Ser Val Leu Leu Phe Pro Gly Gln Pro Ser Pro Ala Arg Cys Leu Ala
    625                 630                 635                 640 cag cag ccc ttg tcc cac ctc ccg ctc acg ggc tgc ctg agc aca ctc    1968
Gln Gln Pro Leu Ser His Leu Pro Leu Thr Gly Cys Leu Ser Thr Leu
                645                 650                 655 ttc ctg cag gcg gcc gag atc ttc gtg gag tca gaa ctg cct ctg agc    2016
Phe Leu Gln Ala Ala Glu Ile Phe Val Glu Ser Glu Leu Pro Leu Ser
            660                 665                 670 tgg gca gac cgg ctg agt ggc tgc ctg cgg ggg ccc tgg gcc tgg ctg    2064
Trp Ala Asp Arg Leu Ser Gly Cys Leu Arg Gly Pro Trp Ala Trp Leu
        675                 680                 685 gtg gtg ctg ctg gcc atg ctg gtg gag gtc gca ctg tgc acc tgg tac    2112
Val Val Leu Leu Ala Met Leu Val Glu Val Ala Leu Cys Thr Trp Tyr
690                 695                 700 ctg gtg gcc ttc ccg ccg gag gtg gtg acg gac tgg cac atg ctg ccc    2160
Leu Val Ala Phe Pro Pro Glu Val Val Thr Asp Trp His Met Leu Pro
705                 710                 715                 720 acg gag gcg ctg gtg cac tgc cgc aca cgc tcc tgg gtc agc ttc ggc    2208
Thr Glu Ala Leu Val His Cys Arg Thr Arg Ser Trp Val Ser Phe Gly
                725                 730                 735 cta gcg cac gcc acc aat gcc acg ctg gcc ttt ctc tgc ttc ctg ggc    2256
Leu Ala His Ala Thr Asn Ala Thr Leu Ala Phe Leu Cys Phe Leu Gly
            740                 745                 750 act ttc ctg gtg cgg agc cag ccg ggc cgc tac aac cgt gcc cgt ggc    2304
Thr Phe Leu Val Arg Ser Gln Pro Gly Arg Tyr Asn Arg Ala Arg Gly
        755                 760                 765 ctc acc ttt gcc atg ctg gcc tac ttc atc acc tgg gtc tcc ttt gtg    2352
Leu Thr Phe Ala Met Leu Ala Tyr Phe Ile Thr Trp Val Ser Phe Val
770                 775                 780 ccc ctc ctg gcc aat gtg cag gtg gtc ctc agg ccc gcc gtg cag atg    2400
Pro Leu Leu Ala Asn Val Gln Val Val Leu Arg Pro Ala Val Gln Met
785                 790                 795                 800 ggc gcc ctc ctc tgt gtc ctg ggc atc ctg gct gcc ttc cac ctg        2448
Gly Ala Leu Leu Cys Val Leu Gly Ile Leu Ala Ala Phe His Leu
                805                 810                 815 ccc agg tgt tac ctg ctc atg cgg cag cca ggg ctc aac acc ccc gag    2496
Pro Arg Cys Tyr Leu Leu Met Arg Gln Pro Gly Leu Asn Thr Pro Glu
            820                 825                 830 ttc ttc ctg gga ggg ggc cct ggg gat gcc caa ggc cag aat gac ggg    2544
Phe Phe Leu Gly Gly Gly Pro Gly Asp Ala Gln Gly Gln Asn Asp Gly
        835                 840                 845 aac aca gga aat cag ggg aaa cat gag tga                            2574
Asn Thr Gly Asn Gln Gly Lys His Glu
    850                 855

<210> SEQ ID NO 37
<211> LENGTH: 857
<212> TYPE: PRT
<213> ORGANISM: Artificial Sequence
<220> FEATURE:
<223> OTHER INFORMATION: chimeric protein

<400> SEQUENCE: 37

Met Pro Ala Leu Ala Ile Met Gly Leu Ser Leu Ala Ala Phe Leu Glu
1               5                   10                  15
```

-continued

Leu Gly Met Gly Ala Ser Leu Cys Leu Ser Gln Gln Phe Lys Ala Gln
            20                  25                  30

Gly Asp Tyr Ile Leu Gly Gly Leu Phe Pro Leu Gly Ser Thr Glu Glu
            35                  40                  45

Ala Thr Leu Asn Gln Arg Thr Gln Pro Asn Ser Ile Pro Cys Asn Arg
 50                  55                  60

Phe Ser Ser Asn Gly Leu Leu Trp Ala Leu Ala Met Lys Met Ala Val
 65                  70                  75                  80

Glu Glu Ile Asn Asn Lys Ser Asp Leu Leu Pro Gly Leu Arg Leu Gly
                85                  90                  95

Tyr Asp Leu Phe Asp Thr Cys Ser Glu Pro Val Val Ala Met Lys Pro
            100                 105                 110

Ser Leu Met Phe Leu Ala Lys Ala Gly Ser Arg Asp Ile Ala Ala Tyr
            115                 120                 125

Cys Asn Tyr Thr Gln Tyr Gln Pro Arg Val Leu Ala Val Ile Gly Pro
 130                 135                 140

His Ser Ser Glu Leu Ala Met Val Thr Gly Lys Phe Phe Ser Phe Phe
145                 150                 155                 160

Leu Met Pro Gln Val Ser Tyr Ser Ala Ser Met Asp Arg Leu Ser Asp
                165                 170                 175

Arg Glu Thr Phe Pro Ser Phe Phe Arg Thr Val Pro Ser Asp Arg Val
            180                 185                 190

Gln Leu Gln Ala Val Val Thr Leu Leu Gln Asn Phe Ser Trp Asn Trp
            195                 200                 205

Val Ala Leu Gly Ser Asp Asp Tyr Gly Arg Glu Gly Leu Ser
 210                 215                 220

Ile Phe Ser Ser Leu Ala Asn Ala Arg Gly Ile Cys Ile Ala His Glu
225                 230                 235                 240

Gly Leu Val Pro Gln His Asp Thr Ser Gly Gln Gln Leu Gly Lys Val
                245                 250                 255

Leu Asp Val Leu Arg Gln Val Asn Gln Ser Lys Val Gln Val Val Val
            260                 265                 270

Leu Phe Ala Ser Ala Arg Ala Val Tyr Ser Leu Phe Ser Tyr Ser Ile
            275                 280                 285

His His Gly Leu Ser Pro Lys Val Trp Val Ala Ser Glu Ser Trp Leu
 290                 295                 300

Thr Ser Asp Leu Val Met Thr Leu Pro Asn Ile Ala Arg Val Gly Thr
305                 310                 315                 320

Val Leu Gly Phe Leu Gln Arg Gly Ala Leu Leu Pro Glu Phe Ser His
                325                 330                 335

Tyr Val Glu Thr His Leu Ala Leu Ala Ala Asp Pro Ala Phe Cys Ala
            340                 345                 350

Ser Leu Asn Ala Glu Leu Asp Leu Glu Glu His Val Met Gly Gln Arg
            355                 360                 365

Cys Pro Arg Cys Asp Asp Ile Met Leu Gln Asn Leu Ser Ser Gly Leu
 370                 375                 380

Leu Gln Asn Leu Ser Ala Gly Gln Leu His His Gln Ile Phe Ala Thr
385                 390                 395                 400

Tyr Ala Ala Val Tyr Ser Val Ala Gln Ala Leu His Asn Thr Leu Gln
                405                 410                 415

Cys Asn Val Ser His Cys His Val Ser Glu His Val Leu Pro Trp Gln
            420                 425                 430

```
Leu Leu Glu Asn Met Tyr Asn Met Ser Phe His Ala Arg Asp Leu Thr
            435                 440                 445

Leu Gln Phe Asp Ala Glu Gly Asn Val Asp Met Glu Tyr Asp Leu Lys
    450                 455                 460

Met Trp Val Trp Gln Ser Pro Thr Pro Val Leu His Thr Val Gly Thr
465                 470                 475                 480

Phe Asn Gly Thr Leu Gln Leu Gln Gln Ser Lys Met Tyr Trp Pro Gly
                485                 490                 495

Asn Gln Val Pro Val Ser Gln Cys Ser Arg Gln Cys Lys Asp Gly Gln
                500                 505                 510

Val Arg Arg Val Lys Gly Phe His Ser Cys Cys Tyr Asp Cys Val Asp
        515                 520                 525

Cys Lys Ala Gly Ser Tyr Arg Lys His Pro Asp Asp Ile Ala Cys Thr
    530                 535                 540

Phe Cys Gly Gln Asp Glu Trp Ser Pro Glu Arg Ser Thr Arg Cys Phe
545                 550                 555                 560

Arg Arg Arg Ser Arg Phe Leu Ala Trp Gly Glu Pro Ala Val Leu Leu
                565                 570                 575

Leu Leu Leu Leu Leu Ser Leu Ala Leu Gly Leu Val Leu Ala Ala Leu
                580                 585                 590

Gly Leu Phe Val His His Arg Asp Ser Pro Leu Val Gln Ala Ser Gly
        595                 600                 605

Gly Pro Leu Ala Cys Phe Gly Leu Val Cys Leu Gly Leu Val Cys Leu
    610                 615                 620

Ser Val Leu Leu Phe Pro Gly Gln Pro Ser Pro Ala Arg Cys Leu Ala
625                 630                 635                 640

Gln Gln Pro Leu Ser His Leu Pro Leu Thr Gly Cys Leu Ser Thr Leu
                645                 650                 655

Phe Leu Gln Ala Ala Glu Ile Phe Val Glu Ser Glu Leu Pro Leu Ser
                660                 665                 670

Trp Ala Asp Arg Leu Ser Gly Cys Leu Arg Gly Pro Trp Ala Trp Leu
        675                 680                 685

Val Val Leu Leu Ala Met Leu Val Glu Val Ala Leu Cys Thr Trp Tyr
    690                 695                 700

Leu Val Ala Phe Pro Pro Glu Val Val Thr Asp Trp His Met Leu Pro
705                 710                 715                 720

Thr Glu Ala Leu Val His Cys Arg Thr Arg Ser Trp Val Ser Phe Gly
                725                 730                 735

Leu Ala His Ala Thr Asn Ala Thr Leu Ala Phe Leu Cys Phe Leu Gly
                740                 745                 750

Thr Phe Leu Val Arg Ser Gln Pro Gly Arg Tyr Asn Arg Ala Arg Gly
        755                 760                 765

Leu Thr Phe Ala Met Leu Ala Tyr Phe Ile Thr Trp Val Ser Phe Val
    770                 775                 780

Pro Leu Leu Ala Asn Val Gln Val Val Leu Arg Pro Ala Val Gln Met
785                 790                 795                 800

Gly Ala Leu Leu Leu Cys Val Leu Gly Ile Leu Ala Ala Phe His Leu
                805                 810                 815

Pro Arg Cys Tyr Leu Leu Met Arg Gln Pro Gly Leu Asn Thr Pro Glu
                820                 825                 830

Phe Phe Leu Gly Gly Gly Pro Gly Asp Ala Gln Gly Gln Asn Asp Gly
        835                 840                 845

Asn Thr Gly Asn Gln Gly Lys His Glu
```

<210> SEQ ID NO 38
<211> LENGTH: 20
<212> TYPE: DNA
<213> ORGANISM: Artificial Sequence
<220> FEATURE:
<223> OTHER INFORMATION: primer

<400> SEQUENCE: 38
ggcaccaggc cctcgtgcgc                                           20

<210> SEQ ID NO 39
<211> LENGTH: 27
<212> TYPE: DNA
<213> ORGANISM: Artificial Sequence
<220> FEATURE:
<223> OTHER INFORMATION: primer

<400> SEQUENCE: 39
gcgcacgagg gcctggtgcc acaacat                                   27

<210> SEQ ID NO 40
<211> LENGTH: 2574
<212> TYPE: DNA
<213> ORGANISM: Artificial Sequence
<220> FEATURE:
<223> OTHER INFORMATION: chimeric gene
<220> FEATURE:
<221> NAME/KEY: CDS
<222> LOCATION: (1)..(2574)

<400> SEQUENCE: 40

| atg | cca | gct | ttg | gct | atc | atg | ggt | ctc | agc | ctg | gct | gct | ttc | ctg | gag | 48 |
| Met | Pro | Ala | Leu | Ala | Ile | Met | Gly | Leu | Ser | Leu | Ala | Ala | Phe | Leu | Glu | |
| 1 | | | | 5 | | | | | 10 | | | | | 15 | | |

| ctt | ggg | atg | ggg | gcc | tct | ttg | tgt | ctg | tca | cag | caa | ttc | aag | gca | caa | 96 |
| Leu | Gly | Met | Gly | Ala | Ser | Leu | Cys | Leu | Ser | Gln | Gln | Phe | Lys | Ala | Gln | |
| | | | 20 | | | | | 25 | | | | | 30 | | | |

| ggg | gac | tac | ata | ctg | ggc | ggg | cta | ttt | ccc | ctg | ggc | tca | acc | gag | gag | 144 |
| Gly | Asp | Tyr | Ile | Leu | Gly | Gly | Leu | Phe | Pro | Leu | Gly | Ser | Thr | Glu | Glu | |
| | | 35 | | | | | 40 | | | | | 45 | | | | |

| gcc | act | ctc | aac | cag | aga | aca | caa | ccc | aac | agc | atc | ccg | tgc | aac | agg | 192 |
| Ala | Thr | Leu | Asn | Gln | Arg | Thr | Gln | Pro | Asn | Ser | Ile | Pro | Cys | Asn | Arg | |
| | 50 | | | | | 55 | | | | | 60 | | | | | |

| ttc | tca | ccc | ctt | ggt | ttg | ttc | ctg | gcc | atg | gct | atg | aag | atg | gct | gtg | 240 |
| Phe | Ser | Pro | Leu | Gly | Leu | Phe | Leu | Ala | Met | Ala | Met | Lys | Met | Ala | Val | |
| 65 | | | | | 70 | | | | | 75 | | | | | 80 | |

| gag | gag | atc | aac | aat | gga | tct | gcc | ttg | ctc | cct | ggg | ctg | cgg | ctg | ggc | 288 |
| Glu | Glu | Ile | Asn | Asn | Gly | Ser | Ala | Leu | Leu | Pro | Gly | Leu | Arg | Leu | Gly | |
| | | | | 85 | | | | | 90 | | | | | 95 | | |

| tat | gac | cta | ttt | gac | aca | tgc | tcc | gag | cca | gtg | gtc | acc | atg | aaa | tcc | 336 |
| Tyr | Asp | Leu | Phe | Asp | Thr | Cys | Ser | Glu | Pro | Val | Val | Thr | Met | Lys | Ser | |
| | | | 100 | | | | | 105 | | | | | 110 | | | |

| agt | ctc | atg | ttc | ctg | gcc | aag | gtg | ggc | agt | caa | agc | att | gct | gcc | tac | 384 |
| Ser | Leu | Met | Phe | Leu | Ala | Lys | Val | Gly | Ser | Gln | Ser | Ile | Ala | Ala | Tyr | |
| | | 115 | | | | | 120 | | | | | 125 | | | | |

| tgc | aac | tac | aca | cag | tac | caa | ccc | cgt | gtg | ctg | gct | gtc | atc | ggc | ccc | 432 |
| Cys | Asn | Tyr | Thr | Gln | Tyr | Gln | Pro | Arg | Val | Leu | Ala | Val | Ile | Gly | Pro | |
| | 130 | | | | | 135 | | | | | 140 | | | | | |

| cac | tca | tca | gag | ctt | gcc | ctc | att | aca | ggc | aag | ttc | ttc | agc | ttc | ttc | 480 |
| His | Ser | Ser | Glu | Leu | Ala | Leu | Ile | Thr | Gly | Lys | Phe | Phe | Ser | Phe | Phe | |
| 145 | | | | | 150 | | | | | 155 | | | | | 160 | |

-continued

| | | |
|---|---|---|
| ctc atg ccc cag gtc agc tac ggt gct agc atg gag ctg ctg agc gcc<br>Leu Met Pro Gln Val Ser Tyr Gly Ala Ser Met Glu Leu Leu Ser Ala<br>165 170 175 | 528 | |
| cgg gag acc ttc ccc tcc ttc ttc cgc acc gtg ccc agc gac cgt gtg<br>Arg Glu Thr Phe Pro Ser Phe Phe Arg Thr Val Pro Ser Asp Arg Val<br>180 185 190 | 576 | |
| cag ctg acg gcc gcc gcg gag ctg ctg cag gag ttc ggc tgg aac tgg<br>Gln Leu Thr Ala Ala Ala Glu Leu Leu Gln Glu Phe Gly Trp Asn Trp<br>195 200 205 | 624 | |
| gtg gcc gcc ctg ggc agc gac gac gag tac ggc cgg cag ggc ctg agc<br>Val Ala Ala Leu Gly Ser Asp Asp Glu Tyr Gly Arg Gln Gly Leu Ser<br>210 215 220 | 672 | |
| atc ttc tcg gcc ctg gcc gcg gca cgc ggc atc tgc atc gcg cac gag<br>Ile Phe Ser Ala Leu Ala Ala Arg Gly Ile Cys Ile Ala His Glu<br>225 230 235 240 | 720 | |
| ggc ctg gtg cca caa cat gac act agt ggc caa cag ttg ggc aag gtg<br>Gly Leu Val Pro Gln His Asp Thr Ser Gly Gln Gln Leu Gly Lys Val<br>245 250 255 | 768 | |
| ctg gat gta cta cgc caa gtg aac caa agt aaa gta caa gtg gtg gtg<br>Leu Asp Val Leu Arg Gln Val Asn Gln Ser Lys Val Gln Val Val Val<br>260 265 270 | 816 | |
| ctg ttt gcc tct gcc cgt gct gtc tac tcc ctt ttt agt tac agc atc<br>Leu Phe Ala Ser Ala Arg Ala Val Tyr Ser Leu Phe Ser Tyr Ser Ile<br>275 280 285 | 864 | |
| cat cat ggc ctc tca ccc aag gta tgg gtg gcc agt gag tct tgg ctg<br>His His Gly Leu Ser Pro Lys Val Trp Val Ala Ser Glu Ser Trp Leu<br>290 295 300 | 912 | |
| aca tct gac ctg gtc atg aca ctt ccc aat att gcc cgt gtg ggc act<br>Thr Ser Asp Leu Val Met Thr Leu Pro Asn Ile Ala Arg Val Gly Thr<br>305 310 315 320 | 960 | |
| gtg ctt ggg ttt ttg cag cgg ggt gcc cta ctg cct gaa ttt tcc cat<br>Val Leu Gly Phe Leu Gln Arg Gly Ala Leu Leu Pro Glu Phe Ser His<br>325 330 335 | 1008 | |
| tat gtg gag act cac ctt gcc ctg gcc gct gac cca gca ttc tgt gcc<br>Tyr Val Glu Thr His Leu Ala Leu Ala Ala Asp Pro Ala Phe Cys Ala<br>340 345 350 | 1056 | |
| tca ctg aat gcg gag ttg gat ctg gag gaa cat gtg atg ggg caa cgc<br>Ser Leu Asn Ala Glu Leu Asp Leu Glu Glu His Val Met Gly Gln Arg<br>355 360 365 | 1104 | |
| tgt cca cgg tgt gac gac atc atg ctg cag aac cta tca tct ggg ctg<br>Cys Pro Arg Cys Asp Asp Ile Met Leu Gln Asn Leu Ser Ser Gly Leu<br>370 375 380 | 1152 | |
| ttg cag aac cta tca gct ggg caa ttg cac cac caa ata ttt gca acc<br>Leu Gln Asn Leu Ser Ala Gly Gln Leu His His Gln Ile Phe Ala Thr<br>385 390 395 400 | 1200 | |
| tat gca gct gtg tac agt gtg gct caa gcc ctt cac aac acc cta cag<br>Tyr Ala Ala Val Tyr Ser Val Ala Gln Ala Leu His Asn Thr Leu Gln<br>405 410 415 | 1248 | |
| tgc aat gtc tca cat tgc cac gta tca gaa cat gtt cta ccc tgg cag<br>Cys Asn Val Ser His Cys His Val Ser Glu His Val Leu Pro Trp Gln<br>420 425 430 | 1296 | |
| ctc ctg gag aac atg tac aat atg agt ttc cat gct cga gac ttg aca<br>Leu Leu Glu Asn Met Tyr Asn Met Ser Phe His Ala Arg Asp Leu Thr<br>435 440 445 | 1344 | |
| cta cag ttt gat gct gaa ggg aat gta gac atg gaa tat gac ctg aag<br>Leu Gln Phe Asp Ala Glu Gly Asn Val Asp Met Glu Tyr Asp Leu Lys<br>450 455 460 | 1392 | |
| atg tgg gtg tgg cag agc cct aca cct gta tta cat act gtg ggc acc<br>Met Trp Val Trp Gln Ser Pro Thr Pro Val Leu His Thr Val Gly Thr<br>465 470 475 480 | 1440 | |

-continued

| | | |
|---|---|---|
| ttc aac ggc acc ctt cag ctg cag cag tct aaa atg tac tgg cca ggc<br>Phe Asn Gly Thr Leu Gln Leu Gln Gln Ser Lys Met Tyr Trp Pro Gly<br>485                        490                    495 | | 1488 |
| aac cag gtg cca gtc tcc cag tgt tcc cgc cag tgc aaa gat ggc cag<br>Asn Gln Val Pro Val Ser Gln Cys Ser Arg Gln Cys Lys Asp Gly Gln<br>500                        505                    510 | | 1536 |
| gtt cgc cga gta aag ggc ttt cat tcc tgc tgc tat gac tgc gtg gac<br>Val Arg Arg Val Lys Gly Phe His Ser Cys Cys Tyr Asp Cys Val Asp<br>515                        520                    525 | | 1584 |
| tgc aag gcg ggc agc tac cgg aag cat cca gac gac atc gcc tgc acc<br>Cys Lys Ala Gly Ser Tyr Arg Lys His Pro Asp Asp Ile Ala Cys Thr<br>530                        535                    540 | | 1632 |
| ttt tgt ggc cag gat gag tgg tcc ccg gag cga agc aca cgc tgc ttc<br>Phe Cys Gly Gln Asp Glu Trp Ser Pro Glu Arg Ser Thr Arg Cys Phe<br>545                        550                    555                    560 | | 1680 |
| cgc cgc agg tct cgg ttc ctg gca tgg ggc gag ccg gct gtg ctg ctg<br>Arg Arg Arg Ser Arg Phe Leu Ala Trp Gly Glu Pro Ala Val Leu Leu<br>565                        570                    575 | | 1728 |
| ctg ctc ctg ctg ctg agc ctg gcg ctg ggc ctt gtg ctg gct gct ttg<br>Leu Leu Leu Leu Leu Ser Leu Ala Leu Gly Leu Val Leu Ala Ala Leu<br>580                        585                    590 | | 1776 |
| ggg ctg ttc gtt cac cat cgg gac agc cca ctg gtt cag gcc tcg ggg<br>Gly Leu Phe Val His His Arg Asp Ser Pro Leu Val Gln Ala Ser Gly<br>595                        600                    605 | | 1824 |
| ggg ccc ctg gcc tgc ttt ggc ctg gtg tgc ctg ggc ctg gtc tgc ctc<br>Gly Pro Leu Ala Cys Phe Gly Leu Val Cys Leu Gly Leu Val Cys Leu<br>610                        615                    620 | | 1872 |
| agc gtc ctc ctg ttc cct ggc cag ccc agc cct gcc cga tgc ctg gcc<br>Ser Val Leu Leu Phe Pro Gly Gln Pro Ser Pro Ala Arg Cys Leu Ala<br>625                        630                    635                    640 | | 1920 |
| cag cag ccc ttg tcc cac ctc ccg ctc acg ggc tgc ctg agc aca ctc<br>Gln Gln Pro Leu Ser His Leu Pro Leu Thr Gly Cys Leu Ser Thr Leu<br>645                        650                    655 | | 1968 |
| ttc ctg cag gcg gcc gag atc ttc gtg gag tca gaa ctg cct ctg agc<br>Phe Leu Gln Ala Ala Glu Ile Phe Val Glu Ser Glu Leu Pro Leu Ser<br>660                        665                    670 | | 2016 |
| tgg gca gac cgg ctg agt ggc tgc ctg cgg ggg ccc tgg gcc tgg ctg<br>Trp Ala Asp Arg Leu Ser Gly Cys Leu Arg Gly Pro Trp Ala Trp Leu<br>675                        680                    685 | | 2064 |
| gtg gtg ctg ctg gcc atg ctg gtg gag gtc gca ctg tgc acc tgg tac<br>Val Val Leu Leu Ala Met Leu Val Glu Val Ala Leu Cys Thr Trp Tyr<br>690                        695                    700 | | 2112 |
| ctg gtg gcc ttc ccg ccg gag gtg gtg acg gac tgg cac atg ctg ccc<br>Leu Val Ala Phe Pro Pro Glu Val Val Thr Asp Trp His Met Leu Pro<br>705                        710                    715                    720 | | 2160 |
| acg gag gcg ctg gtg cac tgc cgc aca cgc tcc tgg gtc agc ttc ggc<br>Thr Glu Ala Leu Val His Cys Arg Thr Arg Ser Trp Val Ser Phe Gly<br>725                        730                    735 | | 2208 |
| cta gcg cac gcc acc aat gcc acg ctg gcc ttt ctc tgc ttc ctg ggc<br>Leu Ala His Ala Thr Asn Ala Thr Leu Ala Phe Leu Cys Phe Leu Gly<br>740                        745                    750 | | 2256 |
| act ttc ctg gtg cgg agc cag ccg ggc cgc tac aac cgt gcc cgt ggc<br>Thr Phe Leu Val Arg Ser Gln Pro Gly Arg Tyr Asn Arg Ala Arg Gly<br>755                        760                    765 | | 2304 |
| ctc acc ttt gcc atg ctg gcc tac ttc atc acc tgg gtc tcc ttt gtg<br>Leu Thr Phe Ala Met Leu Ala Tyr Phe Ile Thr Trp Val Ser Phe Val<br>770                        775                    780 | | 2352 |
| ccc ctc ctg gcc aat gtg cag gtg gtc ctc agg ccc gcc gtg cag atg<br>Pro Leu Leu Ala Asn Val Gln Val Val Leu Arg Pro Ala Val Gln Met | | 2400 |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| 785 |     |     |     |     | 790 |     |     |     |     | 795 |     |     |     |     | 800 |      |
| ggc | gcc | ctc | ctg | ctc | tgt | gtc | ctg | ggc | atc | ctg | gct | gcc | ttc | cac | ctg | 2448 |
| Gly | Ala | Leu | Leu | Leu | Cys | Val | Leu | Gly | Ile | Leu | Ala | Ala | Phe | His | Leu |      |
|     |     |     |     | 805 |     |     |     |     | 810 |     |     |     |     | 815 |     |      |
| ccc | agg | tgt | tac | ctg | ctc | atg | cgg | cag | cca | ggg | ctc | aac | acc | ccc | gag | 2496 |
| Pro | Arg | Cys | Tyr | Leu | Leu | Met | Arg | Gln | Pro | Gly | Leu | Asn | Thr | Pro | Glu |      |
|     |     | 820 |     |     |     |     | 825 |     |     |     |     | 830 |     |     |     |      |
| ttc | ttc | ctg | gga | ggg | ggc | cct | ggg | gat | gcc | caa | ggc | cag | aat | gac | ggg | 2544 |
| Phe | Phe | Leu | Gly | Gly | Gly | Pro | Gly | Asp | Ala | Gln | Gly | Gln | Asn | Asp | Gly |      |
|     |     | 835 |     |     |     |     | 840 |     |     |     |     | 845 |     |     |     |      |
| aac | aca | gga | aat | cag | ggg | aaa | cat | gag | tga |     |     |     |     |     |     | 2574 |
| Asn | Thr | Gly | Asn | Gln | Gly | Lys | His | Glu |     |     |     |     |     |     |     |      |
|     | 850 |     |     |     |     | 855 |     |     |     |     |     |     |     |     |     |      |

<210> SEQ ID NO 41
<211> LENGTH: 857
<212> TYPE: PRT
<213> ORGANISM: Artificial Sequence
<220> FEATURE:
<223> OTHER INFORMATION: chimeric protein

<400> SEQUENCE: 41

Met Pro Ala Leu Ala Ile Met Gly Leu Ser Leu Ala Ala Phe Leu Glu
1               5                   10                  15

Leu Gly Met Gly Ala Ser Leu Cys Leu Ser Gln Gln Phe Lys Ala Gln
            20                  25                  30

Gly Asp Tyr Ile Leu Gly Gly Leu Phe Pro Leu Gly Ser Thr Glu Glu
        35                  40                  45

Ala Thr Leu Asn Gln Arg Thr Gln Pro Asn Ser Ile Pro Cys Asn Arg
    50                  55                  60

Phe Ser Pro Leu Gly Leu Phe Leu Ala Met Ala Met Lys Met Ala Val
65                  70                  75                  80

Glu Glu Ile Asn Asn Gly Ser Ala Leu Leu Pro Gly Leu Arg Leu Gly
                85                  90                  95

Tyr Asp Leu Phe Asp Thr Cys Ser Glu Pro Val Val Thr Met Lys Ser
            100                 105                 110

Ser Leu Met Phe Leu Ala Lys Val Gly Ser Gln Ser Ile Ala Ala Tyr
        115                 120                 125

Cys Asn Tyr Thr Gln Tyr Gln Pro Arg Val Leu Ala Val Ile Gly Pro
    130                 135                 140

His Ser Ser Glu Leu Ala Leu Ile Thr Gly Lys Phe Phe Ser Phe Phe
145                 150                 155                 160

Leu Met Pro Gln Val Ser Tyr Gly Ala Ser Met Glu Leu Leu Ser Ala
                165                 170                 175

Arg Glu Thr Phe Pro Ser Phe Phe Arg Thr Val Pro Ser Asp Arg Val
            180                 185                 190

Gln Leu Thr Ala Ala Ala Glu Leu Leu Gln Glu Phe Gly Trp Asn Trp
        195                 200                 205

Val Ala Ala Leu Gly Ser Asp Asp Glu Tyr Gly Arg Gln Gly Leu Ser
    210                 215                 220

Ile Phe Ser Ala Leu Ala Ala Arg Gly Ile Cys Ile Ala His Glu
225                 230                 235                 240

Gly Leu Val Pro Gln His Asp Thr Ser Gly Gln Gln Leu Gly Lys Val
                245                 250                 255

Leu Asp Val Leu Arg Gln Val Asn Gln Ser Lys Val Gln Val Val Val
            260                 265                 270

```
Leu Phe Ala Ser Ala Arg Ala Val Tyr Ser Leu Phe Ser Tyr Ser Ile
            275                 280                 285

His His Gly Leu Ser Pro Lys Val Trp Val Ala Ser Glu Ser Trp Leu
        290                 295                 300

Thr Ser Asp Leu Val Met Thr Leu Pro Asn Ile Ala Arg Val Gly Thr
305                 310                 315                 320

Val Leu Gly Phe Leu Gln Arg Gly Ala Leu Leu Pro Glu Phe Ser His
                325                 330                 335

Tyr Val Glu Thr His Leu Ala Leu Ala Ala Asp Pro Ala Phe Cys Ala
            340                 345                 350

Ser Leu Asn Ala Glu Leu Asp Leu Glu Glu His Val Met Gly Gln Arg
        355                 360                 365

Cys Pro Arg Cys Asp Asp Ile Met Leu Gln Asn Leu Ser Ser Gly Leu
370                 375                 380

Leu Gln Asn Leu Ser Ala Gly Gln Leu His His Gln Ile Phe Ala Thr
385                 390                 395                 400

Tyr Ala Ala Val Tyr Ser Val Ala Gln Ala Leu His Asn Thr Leu Gln
                405                 410                 415

Cys Asn Val Ser His Cys His Val Ser Glu His Val Leu Pro Trp Gln
            420                 425                 430

Leu Leu Glu Asn Met Tyr Asn Met Ser Phe His Ala Arg Asp Leu Thr
        435                 440                 445

Leu Gln Phe Asp Ala Glu Gly Asn Val Asp Met Glu Tyr Asp Leu Lys
450                 455                 460

Met Trp Val Trp Gln Ser Pro Thr Pro Val Leu His Thr Val Gly Thr
465                 470                 475                 480

Phe Asn Gly Thr Leu Gln Leu Gln Gln Ser Lys Met Tyr Trp Pro Gly
                485                 490                 495

Asn Gln Val Pro Val Ser Gln Cys Ser Arg Gln Cys Lys Asp Gly Gln
            500                 505                 510

Val Arg Arg Val Lys Gly Phe His Ser Cys Cys Tyr Asp Cys Val Asp
        515                 520                 525

Cys Lys Ala Gly Ser Tyr Arg Lys His Pro Asp Asp Ile Ala Cys Thr
530                 535                 540

Phe Cys Gly Gln Asp Glu Trp Ser Pro Glu Arg Ser Thr Arg Cys Phe
545                 550                 555                 560

Arg Arg Arg Ser Arg Phe Leu Ala Trp Gly Glu Pro Ala Val Leu Leu
                565                 570                 575

Leu Leu Leu Leu Leu Ser Leu Ala Leu Gly Leu Val Leu Ala Ala Leu
            580                 585                 590

Gly Leu Phe Val His His Arg Asp Ser Pro Leu Val Gln Ala Ser Gly
        595                 600                 605

Gly Pro Leu Ala Cys Phe Gly Leu Val Cys Leu Gly Leu Val Cys Leu
610                 615                 620

Ser Val Leu Leu Phe Pro Gly Gln Pro Ser Pro Ala Arg Cys Leu Ala
625                 630                 635                 640

Gln Gln Pro Leu Ser His Leu Pro Leu Thr Gly Cys Leu Ser Thr Leu
                645                 650                 655

Phe Leu Gln Ala Ala Glu Ile Phe Val Glu Ser Glu Leu Pro Leu Ser
            660                 665                 670

Trp Ala Asp Arg Leu Ser Gly Cys Leu Arg Gly Pro Trp Ala Trp Leu
        675                 680                 685

Val Val Leu Leu Ala Met Leu Val Glu Val Ala Leu Cys Thr Trp Tyr
```

```
                    690             695             700
Leu Val Ala Phe Pro Pro Glu Val Val Thr Asp Trp His Met Leu Pro
705                 710                 715                 720

Thr Glu Ala Leu Val His Cys Arg Thr Arg Ser Trp Val Ser Phe Gly
            725                 730                 735

Leu Ala His Ala Thr Asn Ala Thr Leu Ala Phe Leu Cys Phe Leu Gly
            740                 745                 750

Thr Phe Leu Val Arg Ser Gln Pro Gly Arg Tyr Asn Arg Ala Arg Gly
            755                 760                 765

Leu Thr Phe Ala Met Leu Ala Tyr Phe Ile Thr Trp Val Ser Phe Val
            770                 775                 780

Pro Leu Leu Ala Asn Val Gln Val Val Leu Arg Pro Ala Val Gln Met
785                 790                 795                 800

Gly Ala Leu Leu Leu Cys Val Leu Gly Ile Leu Ala Ala Phe His Leu
                805                 810                 815

Pro Arg Cys Tyr Leu Leu Met Arg Gln Pro Gly Leu Asn Thr Pro Glu
                820                 825                 830

Phe Phe Leu Gly Gly Gly Pro Gly Asp Ala Gln Gly Gln Asn Asp Gly
                835                 840                 845

Asn Thr Gly Asn Gln Gly Lys His Glu
    850                 855

<210> SEQ ID NO 42
<211> LENGTH: 33
<212> TYPE: DNA
<213> ORGANISM: Artificial Sequence
<220> FEATURE:
<223> OTHER INFORMATION: primer

<400> SEQUENCE: 42
tagcgtttaa acttaccacc atggcccggt ccc                           33

<210> SEQ ID NO 43
<211> LENGTH: 40
<212> TYPE: DNA
<213> ORGANISM: Artificial Sequence
<220> FEATURE:
<223> OTHER INFORMATION: primer

<400> SEQUENCE: 43
gtttaaacgg gccctgtcac aacaggttga tctcgtccag                    40

<210> SEQ ID NO 44
<211> LENGTH: 42
<212> TYPE: DNA
<213> ORGANISM: Artificial Sequence
<220> FEATURE:
<223> OTHER INFORMATION: primer

<400> SEQUENCE: 44
tagcgtttaa acttaccgcc atggggagtg gcatcagtgc tg                 42

<210> SEQ ID NO 45
<211> LENGTH: 40
<212> TYPE: DNA
<213> ORGANISM: Artificial Sequence
<220> FEATURE:
<223> OTHER INFORMATION: primer

<400> SEQUENCE: 45
gtttaaacgg gccctcggag gaaccgagca ttaaaagagc                    40
```

<210> SEQ ID NO 46
<211> LENGTH: 35
<212> TYPE: DNA
<213> ORGANISM: Artificial Sequence
<220> FEATURE:
<223> OTHER INFORMATION: primer

<400> SEQUENCE: 46
caagttgagg tcaaggaagg gctctgcaca gctcg                              35

<210> SEQ ID NO 47
<211> LENGTH: 35
<212> TYPE: DNA
<213> ORGANISM: Artificial Sequence
<220> FEATURE:
<223> OTHER INFORMATION: primer

<400> SEQUENCE: 47
cttgacctca acttgaggaa agatgacaaa gagat                              35

<210> SEQ ID NO 48
<211> LENGTH: 40
<212> TYPE: DNA
<213> ORGANISM: Artificial Sequence
<220> FEATURE:
<223> OTHER INFORMATION: primer

<400> SEQUENCE: 48
gctggatatc tgcagcggag gaaccgagca ttaaaagagc                         40

<210> SEQ ID NO 49
<211> LENGTH: 1125
<212> TYPE: DNA
<213> ORGANISM: Artificial Sequence
<220> FEATURE:
<223> OTHER INFORMATION: chimeric gene
<220> FEATURE:
<221> NAME/KEY: CDS
<222> LOCATION: (1)..(1125)

<400> SEQUENCE: 49

| atg | gcc | cgg | tcc | ctg | act | tgg | ggc | tgc | tgt | ccc | tgg | tgc | ctg | acg | gaa | 48 |
| Met | Ala | Arg | Ser | Leu | Thr | Trp | Gly | Cys | Cys | Pro | Trp | Cys | Leu | Thr | Glu | |
| 1 | | | | 5 | | | | | 10 | | | | | 15 | | |

| gag | gag | aag | act | gcc | gcc | aga | atc | gac | cag | gag | atc | aac | aag | att | ttg | 96 |
| Glu | Glu | Lys | Thr | Ala | Ala | Arg | Ile | Asp | Gln | Glu | Ile | Asn | Lys | Ile | Leu | |
| | | | 20 | | | | | 25 | | | | | 30 | | | |

| ttg | gaa | cag | aag | aaa | caa | gag | cgc | ggg | gaa | ttg | aaa | ctc | ctg | ctg | ttg | 144 |
| Leu | Glu | Gln | Lys | Lys | Gln | Glu | Arg | Gly | Glu | Leu | Lys | Leu | Leu | Leu | Leu | |
| | | 35 | | | | | 40 | | | | | 45 | | | | |

| ggg | ccc | ggt | gag | agc | ggg | aaa | agc | acg | ttc | atc | aag | caa | atg | cgc | atc | 192 |
| Gly | Pro | Gly | Glu | Ser | Gly | Lys | Ser | Thr | Phe | Ile | Lys | Gln | Met | Arg | Ile | |
| | 50 | | | | | 55 | | | | | 60 | | | | | |

| att | cac | ggc | gcc | ggc | tac | tct | gag | gag | gac | cgc | aga | gcc | ttc | cgg | ctg | 240 |
| Ile | His | Gly | Ala | Gly | Tyr | Ser | Glu | Glu | Asp | Arg | Arg | Ala | Phe | Arg | Leu | |
| 65 | | | | | 70 | | | | | 75 | | | | | 80 | |

| ctc | gtc | tac | cag | aac | atc | ttc | gtc | tcc | atg | cag | gcc | atg | att | gaa | gca | 288 |
| Leu | Val | Tyr | Gln | Asn | Ile | Phe | Val | Ser | Met | Gln | Ala | Met | Ile | Glu | Ala | |
| | | | | 85 | | | | | 90 | | | | | 95 | | |

| atg | gac | agg | ctg | cag | atc | ccc | ttc | agc | agg | ccg | gac | agc | aaa | cag | cac | 336 |
| Met | Asp | Arg | Leu | Gln | Ile | Pro | Phe | Ser | Arg | Pro | Asp | Ser | Lys | Gln | His | |
| | | | 100 | | | | | 105 | | | | | 110 | | | |

| gcc | agc | ctg | gtg | atg | acc | cag | gac | ccc | tat | aaa | gtg | agc | tcg | ttc | gag | 384 |

```
Ala Ser Leu Val Met Thr Gln Asp Pro Tyr Lys Val Ser Ser Phe Glu
            115                 120                 125 aag cca tat gca gtg gcc atg cag tac ctg tgg cgg gac gcg ggc atc       432
Lys Pro Tyr Ala Val Ala Met Gln Tyr Leu Trp Arg Asp Ala Gly Ile
    130                 135                 140 cgc gca tgc tac gag cgg agg cgt gaa ttc cac ctg ctg gac tcc gcg       480
Arg Ala Cys Tyr Glu Arg Arg Arg Glu Phe His Leu Leu Asp Ser Ala
145                 150                 155                 160 gtg tac tac ctg tca cac ctg gag cgc atc gcc gag gac gac tac atc       528
Val Tyr Tyr Leu Ser His Leu Glu Arg Ile Ala Glu Asp Asp Tyr Ile
                    165                 170                 175 ccc act gcg cag gac gtg ctg cgc agt cgc atg ccc acc act ggc atc       576
Pro Thr Ala Gln Asp Val Leu Arg Ser Arg Met Pro Thr Thr Gly Ile
                180                 185                 190 aat gag tac tgc ttt tcc gtg cag aaa acc aaa ctg cgc atc gtg gat       624
Asn Glu Tyr Cys Phe Ser Val Gln Lys Thr Lys Leu Arg Ile Val Asp
            195                 200                 205 gct ggc ggc cag aag tca gaa cgt aag aaa tgg atc cac tgt ttc gag       672
Ala Gly Gly Gln Lys Ser Glu Arg Lys Lys Trp Ile His Cys Phe Glu
210                 215                 220 aac gtg att gcc ctc atc tac ctg gcg tct ctg agc gag tat gac cag       720
Asn Val Ile Ala Leu Ile Tyr Leu Ala Ser Leu Ser Glu Tyr Asp Gln
225                 230                 235                 240 tgt ctg gag gag aac agt cag gag aac cgt atg aag gag agt ctc gct       768
Cys Leu Glu Glu Asn Ser Gln Glu Asn Arg Met Lys Glu Ser Leu Ala
                    245                 250                 255 ctg ttt agc acg atc cta gag ctg ccc tgg ttc aag agc acc tcg gtc       816
Leu Phe Ser Thr Ile Leu Glu Leu Pro Trp Phe Lys Ser Thr Ser Val
                260                 265                 270 atc ctc ttc ctc aac aag aca gac atc ctg gag gat aaa atc cac acc       864
Ile Leu Phe Leu Asn Lys Thr Asp Ile Leu Glu Asp Lys Ile His Thr
            275                 280                 285 tcc cac cta gcc tca tac ttc ccc agc ttc cag gga ccc cgg agg gac       912
Ser His Leu Ala Ser Tyr Phe Pro Ser Phe Gln Gly Pro Arg Arg Asp
        290                 295                 300 gca gag gcc gcc aag cgc ttc atc ttg gac atg tac gcg cgc gtg tac       960
Ala Glu Ala Ala Lys Arg Phe Ile Leu Asp Met Tyr Ala Arg Val Tyr
305                 310                 315                 320 gcg agc tgt gca gag ccc ttc ctt gac ctc aac ttg agg aaa gat gac      1008
Ala Ser Cys Ala Glu Pro Phe Leu Asp Leu Asn Leu Arg Lys Asp Asp
                    325                 330                 335 aaa gag atc tac agc cac atg act tgt gct acg gac aca cag aac gtc      1056
Lys Glu Ile Tyr Ser His Met Thr Cys Ala Thr Asp Thr Gln Asn Val
                340                 345                 350 aaa ttt gtg ttt gat gca gtc aca gac att atc atc aag gaa aac ctc      1104
Lys Phe Val Phe Asp Ala Val Thr Asp Ile Ile Ile Lys Glu Asn Leu
            355                 360                 365 aag gac tgt ggg ctc ttt taa                                          1125
Lys Asp Cys Gly Leu Phe
        370

<210> SEQ ID NO 50
<211> LENGTH: 374
<212> TYPE: PRT
<213> ORGANISM: Artificial Sequence
<220> FEATURE:
<223> OTHER INFORMATION: chimeric protein

<400> SEQUENCE: 50

Met Ala Arg Ser Leu Thr Trp Gly Cys Cys Pro Trp Cys Leu Thr Glu
1               5                   10                  15
```

Glu Glu Lys Thr Ala Ala Arg Ile Asp Gln Glu Ile Asn Lys Ile Leu
            20                  25                  30

Leu Glu Gln Lys Lys Gln Arg Gly Glu Leu Lys Leu Leu Leu
        35                  40                  45

Gly Pro Gly Glu Ser Gly Lys Ser Thr Phe Ile Lys Gln Met Arg Ile
 50                  55                  60

Ile His Gly Ala Gly Tyr Ser Glu Glu Asp Arg Arg Ala Phe Arg Leu
 65                  70                  75                  80

Leu Val Tyr Gln Asn Ile Phe Val Ser Met Gln Ala Met Ile Glu Ala
                85                  90                  95

Met Asp Arg Leu Gln Ile Pro Phe Ser Arg Pro Asp Ser Lys Gln His
            100                 105                 110

Ala Ser Leu Val Met Thr Gln Asp Pro Tyr Lys Val Ser Ser Phe Glu
        115                 120                 125

Lys Pro Tyr Ala Val Ala Met Gln Tyr Leu Trp Arg Asp Ala Gly Ile
130                 135                 140

Arg Ala Cys Tyr Glu Arg Arg Glu Phe His Leu Leu Asp Ser Ala
145                 150                 155                 160

Val Tyr Tyr Leu Ser His Leu Glu Arg Ile Ala Glu Asp Tyr Ile
                165                 170                 175

Pro Thr Ala Gln Asp Val Leu Arg Ser Arg Met Pro Thr Thr Gly Ile
            180                 185                 190

Asn Glu Tyr Cys Phe Ser Val Gln Lys Thr Lys Leu Arg Ile Val Asp
        195                 200                 205

Ala Gly Gly Gln Lys Ser Glu Arg Lys Lys Trp Ile His Cys Phe Glu
210                 215                 220

Asn Val Ile Ala Leu Ile Tyr Leu Ala Ser Leu Ser Glu Tyr Asp Gln
225                 230                 235                 240

Cys Leu Glu Glu Asn Ser Gln Glu Asn Arg Met Lys Glu Ser Leu Ala
                245                 250                 255

Leu Phe Ser Thr Ile Leu Glu Leu Pro Trp Phe Lys Ser Thr Ser Val
            260                 265                 270

Ile Leu Phe Leu Asn Lys Thr Asp Ile Leu Glu Asp Lys Ile His Thr
        275                 280                 285

Ser His Leu Ala Ser Tyr Phe Pro Ser Phe Gln Gly Pro Arg Arg Asp
290                 295                 300

Ala Glu Ala Ala Lys Arg Phe Ile Leu Asp Met Tyr Ala Arg Val Tyr
305                 310                 315                 320

Ala Ser Cys Ala Glu Pro Phe Leu Asp Leu Asn Leu Arg Lys Asp Asp
                325                 330                 335

Lys Glu Ile Tyr Ser His Met Thr Cys Ala Thr Asp Thr Gln Asn Val
            340                 345                 350

Lys Phe Val Phe Asp Ala Val Thr Asp Ile Ile Ile Lys Glu Asn Leu
        355                 360                 365

Lys Asp Cys Gly Leu Phe
    370

<210> SEQ ID NO 51
<211> LENGTH: 2520
<212> TYPE: DNA
<213> ORGANISM: Homo sapiens
<220> FEATURE:
<221> NAME/KEY: CDS
<222> LOCATION: (1)..(2520)

<400> SEQUENCE: 51

| | | |
|---|---|---|
| atg ggg ccc agg gca aag acc atc tcc tcc ctg ttc ttc ctc cta tgg<br>Met Gly Pro Arg Ala Lys Thr Ile Ser Ser Leu Phe Phe Leu Leu Trp<br>1               5                   10                  15 | 48 |
| gtc ctg gct gag ccg gct gag aac tcg gac ttc tac ctg cct ggg gat<br>Val Leu Ala Glu Pro Ala Glu Asn Ser Asp Phe Tyr Leu Pro Gly Asp<br>            20                  25                  30 | 96 |
| tac ctc ctg ggt ggc ctc ttc tcc ctc cat gcc aac atg aag ggc att<br>Tyr Leu Leu Gly Gly Leu Phe Ser Leu His Ala Asn Met Lys Gly Ile<br>        35                  40                  45 | 144 |
| gtt cac ctt aac ttc ctg cag gtg ccc atg tgc aag gag tat gaa gtg<br>Val His Leu Asn Phe Leu Gln Val Pro Met Cys Lys Glu Tyr Glu Val<br>    50                  55                  60 | 192 |
| aag gtg ata ggc tac aac ctc atg cag gcc atg cgc ttt gcg gtg gag<br>Lys Val Ile Gly Tyr Asn Leu Met Gln Ala Met Arg Phe Ala Val Glu<br>65                  70                  75                  80 | 240 |
| gag atc aac aat gac agc agc ctg ctg cct ggt gtg ctg ctg ggc tat<br>Glu Ile Asn Asn Asp Ser Ser Leu Leu Pro Gly Val Leu Leu Gly Tyr<br>                85                  90                  95 | 288 |
| gag atc gtg gat gtg tgc tac atc tcc aac aat gtc cag ccg gtg ctc<br>Glu Ile Val Asp Val Cys Tyr Ile Ser Asn Asn Val Gln Pro Val Leu<br>            100                 105                 110 | 336 |
| tac ttc ctg gca cac gag gac aac ctc ctt ccc atc caa gag gac tac<br>Tyr Phe Leu Ala His Glu Asp Asn Leu Leu Pro Ile Gln Glu Asp Tyr<br>        115                 120                 125 | 384 |
| agt aac tac att tcc cgt gtg gtg gct gtc att ggc cct gac aac tcc<br>Ser Asn Tyr Ile Ser Arg Val Val Ala Val Ile Gly Pro Asp Asn Ser<br>    130                 135                 140 | 432 |
| gag tct gtc atg act gtg gcc aac ttc ctc tcc cta ttt ctc ctt cca<br>Glu Ser Val Met Thr Val Ala Asn Phe Leu Ser Leu Phe Leu Leu Pro<br>145                 150                 155                 160 | 480 |
| cag atc acc tac agc gcc atc agc gat gag ctg cga gac aag gtg cgc<br>Gln Ile Thr Tyr Ser Ala Ile Ser Asp Glu Leu Arg Asp Lys Val Arg<br>                165                 170                 175 | 528 |
| ttc ccg gct ttg ctg cgt acc aca ccc agc gcc gac cac cac atc gag<br>Phe Pro Ala Leu Leu Arg Thr Thr Pro Ser Ala Asp His His Ile Glu<br>            180                 185                 190 | 576 |
| gcc atg gtg cag ctg atg ctg cac ttc cgc tgg aac tgg atc att gtg<br>Ala Met Val Gln Leu Met Leu His Phe Arg Trp Asn Trp Ile Ile Val<br>        195                 200                 205 | 624 |
| ctg gtg agc agc gac acc tat ggc cgc gac aat ggc cag ctg ctt ggc<br>Leu Val Ser Ser Asp Thr Tyr Gly Arg Asp Asn Gly Gln Leu Leu Gly<br>    210                 215                 220 | 672 |
| gag cgc gtg gcc cgg cgc gac atc tgc atc gcc ttc cag gag acg ctg<br>Glu Arg Val Ala Arg Arg Asp Ile Cys Ile Ala Phe Gln Glu Thr Leu<br>225                 230                 235                 240 | 720 |
| ccc aca ctg cag ccc aac cag aac atg acg tca gag gag cgc cag cgc<br>Pro Thr Leu Gln Pro Asn Gln Asn Met Thr Ser Glu Glu Arg Gln Arg<br>                245                 250                 255 | 768 |
| ctg gtg acc att gtg gac aag ctg cag cag agc aca gcg cgc gtc gtg<br>Leu Val Thr Ile Val Asp Lys Leu Gln Gln Ser Thr Ala Arg Val Val<br>            260                 265                 270 | 816 |
| gtc gtg ttc tcg ccc gac ctg acc ctg tac cac ttc ttc aat gag gtg<br>Val Val Phe Ser Pro Asp Leu Thr Leu Tyr His Phe Phe Asn Glu Val<br>        275                 280                 285 | 864 |
| ctg cgc cag aac ttc act ggc gcc gtg tgg atc gcc tcc gag tcc tgg<br>Leu Arg Gln Asn Phe Thr Gly Ala Val Trp Ile Ala Ser Glu Ser Trp<br>    290                 295                 300 | 912 |
| gcc atc gac ccg gtc ctg cac aac ctc acg gag ctg cgc cac ttg ggc<br>Ala Ile Asp Pro Val Leu His Asn Leu Thr Glu Leu Arg His Leu Gly | 960 |

```
                    Ala Ile Asp Pro Val Leu His Asn Leu Thr Glu Leu Arg His Leu Gly
                    305                 310                 315                 320 acc ttc ctg ggc atc acc atc cag agc gtg ccc atc ccg ggc ttc agt                    1008
Thr Phe Leu Gly Ile Thr Ile Gln Ser Val Pro Ile Pro Gly Phe Ser
                325                 330                 335 gag ttc cgc gag tgg ggc cca cag gct ggg ccg cca ccc ctc agc agg                    1056
Glu Phe Arg Glu Trp Gly Pro Gln Ala Gly Pro Pro Pro Leu Ser Arg
            340                 345                 350 acc agc cag agc tat acc tgc aac cag gag tgc gac aac tgc ctg aac                    1104
Thr Ser Gln Ser Tyr Thr Cys Asn Gln Glu Cys Asp Asn Cys Leu Asn
        355                 360                 365 gcc acc ttg tcc ttc aac acc att ctc agg ctc tct ggg gag cgt gtc                    1152
Ala Thr Leu Ser Phe Asn Thr Ile Leu Arg Leu Ser Gly Glu Arg Val
    370                 375                 380 gtc tac agc gtg tac tct gcg gtc tat gct gtg gcc cat gcc ctg cac                    1200
Val Tyr Ser Val Tyr Ser Ala Val Tyr Ala Val Ala His Ala Leu His
385                 390                 395                 400 agc ctc ctc ggc tgt gac aaa agc acc tgc acc aag agg gtg gtc tac                    1248
Ser Leu Leu Gly Cys Asp Lys Ser Thr Cys Thr Lys Arg Val Val Tyr
                405                 410                 415 ccc tgg cag ctg ctt gag gag atc tgg aag gtc aac ttc act ctc ctg                    1296
Pro Trp Gln Leu Leu Glu Glu Ile Trp Lys Val Asn Phe Thr Leu Leu
            420                 425                 430 gac cac caa atc ttc ttc gac ccg caa ggg gac gtg gct ctg cac ttg                    1344
Asp His Gln Ile Phe Phe Asp Pro Gln Gly Asp Val Ala Leu His Leu
        435                 440                 445 gag att gtc cag tgg caa tgg gac cgg agc cag aat ccc ttc cag agc                    1392
Glu Ile Val Gln Trp Gln Trp Asp Arg Ser Gln Asn Pro Phe Gln Ser
    450                 455                 460 gtc gcc tcc tac tac ccc ctg cag cga cag ctg aag aac atc caa gac                    1440
Val Ala Ser Tyr Tyr Pro Leu Gln Arg Gln Leu Lys Asn Ile Gln Asp
465                 470                 475                 480 atc tcc tgg cac acc atc aac aac acg atc cct atg tcc atg tgt tcc                    1488
Ile Ser Trp His Thr Ile Asn Asn Thr Ile Pro Met Ser Met Cys Ser
                485                 490                 495 aag agg tgc cag tca ggg caa aag aag aag cct gtg ggc atc cac gtc                    1536
Lys Arg Cys Gln Ser Gly Gln Lys Lys Lys Pro Val Gly Ile His Val
            500                 505                 510 tgc tgc ttc gag tgc atc gac tgc ctt ccc ggc acc ttc ctc aac cac                    1584
Cys Cys Phe Glu Cys Ile Asp Cys Leu Pro Gly Thr Phe Leu Asn His
        515                 520                 525 act gaa gat gaa tat gaa tgc cag gcc tgc ccg aat aac gag tgg tcc                    1632
Thr Glu Asp Glu Tyr Glu Cys Gln Ala Cys Pro Asn Asn Glu Trp Ser
    530                 535                 540 tac cag agt gag acc tcc tgc ttc aag cgg cag ctg gtc ttc ctg gaa                    1680
Tyr Gln Ser Glu Thr Ser Cys Phe Lys Arg Gln Leu Val Phe Leu Glu
545                 550                 555                 560 tgg cat gag gca ccc acc atc gct gtg gcc ctg ctg gcc gcc ctg ggc                    1728
Trp His Glu Ala Pro Thr Ile Ala Val Ala Leu Leu Ala Ala Leu Gly
                565                 570                 575 ttc ctc agc acc ctg gcc atc ctg gtg ata ttc tgg agg cac ttc cag                    1776
Phe Leu Ser Thr Leu Ala Ile Leu Val Ile Phe Trp Arg His Phe Gln
            580                 585                 590 aca ccc ata gtt cgc tcg gct ggg ggc ccc atg tgc ttc ctg atg ctg                    1824
Thr Pro Ile Val Arg Ser Ala Gly Gly Pro Met Cys Phe Leu Met Leu
        595                 600                 605 aca ctg ctg ctg gtg gca tac atg gtg gtc ccg gtg tac gtg ggg ccg                    1872
Thr Leu Leu Leu Val Ala Tyr Met Val Val Pro Val Tyr Val Gly Pro
    610                 615                 620
```

-continued

| | | |
|---|---|---|
| ccc aag gtc tcc acc tgc ctc tgc cgc cag gcc ctc ttt ccc ctc tgc<br>Pro Lys Val Ser Thr Cys Leu Cys Arg Gln Ala Leu Phe Pro Leu Cys<br>625                       630                       635                       640 | | 1920 |
| ttc aca atc tgc atc tcc tgt atc gcc gtg cgt tct ttc cag atc gtc<br>Phe Thr Ile Cys Ile Ser Cys Ile Ala Val Arg Ser Phe Gln Ile Val<br>                       645                       650                       655 | | 1968 |
| tgc gcc ttc aag atg gcc agc cgc ttc cca cgc gcc tac agc tac tgg<br>Cys Ala Phe Lys Met Ala Ser Arg Phe Pro Arg Ala Tyr Ser Tyr Trp<br>                660                       665                       670 | | 2016 |
| gtc cgc tac cag ggg ccc tac gtc tct atg gca ttt atc acg gta ctc<br>Val Arg Tyr Gln Gly Pro Tyr Val Ser Met Ala Phe Ile Thr Val Leu<br>675                       680                       685 | | 2064 |
| aaa atg gtc att gtg gta att ggc atg ctg gcc acg ggc ctc agt ccc<br>Lys Met Val Ile Val Val Ile Gly Met Leu Ala Thr Gly Leu Ser Pro<br>    690                       695                       700 | | 2112 |
| acc acc cgt act gac ccc gat gac ccc aag atc aca att gtc tcc tgt<br>Thr Thr Arg Thr Asp Pro Asp Asp Pro Lys Ile Thr Ile Val Ser Cys<br>705                       710                       715                       720 | | 2160 |
| aac ccc aac tac cgc aac agc ctg ctg ttc aac acc agc ctg gac ctg<br>Asn Pro Asn Tyr Arg Asn Ser Leu Leu Phe Asn Thr Ser Leu Asp Leu<br>                       725                       730                       735 | | 2208 |
| ctg ctc tca gtg gtg ggt ttc agc ttc gcc tac atg ggc aaa gag ctg<br>Leu Leu Ser Val Val Gly Phe Ser Phe Ala Tyr Met Gly Lys Glu Leu<br>    740                       745                       750 | | 2256 |
| ccc acc aac tac aac gag gcc aag ttc atc acc ctc agc atg acc ttc<br>Pro Thr Asn Tyr Asn Glu Ala Lys Phe Ile Thr Leu Ser Met Thr Phe<br>755                       760                       765 | | 2304 |
| tat ttc acc tca tcc gtc tcc ctc tgc acc ttc atg tct gcc tac agc<br>Tyr Phe Thr Ser Ser Val Ser Leu Cys Thr Phe Met Ser Ala Tyr Ser<br>    770                       775                       780 | | 2352 |
| ggg gtg ctg gtc acc atc gtg gac ctc ttg gtc act gtg ctc aac ctc<br>Gly Val Leu Val Thr Ile Val Asp Leu Leu Val Thr Val Leu Asn Leu<br>785                       790                       795                       800 | | 2400 |
| ctg gcc atc agc ctg ggc tac ttc ggc ccc aag tgc tac atg atc ctc<br>Leu Ala Ile Ser Leu Gly Tyr Phe Gly Pro Lys Cys Tyr Met Ile Leu<br>                       805                       810                       815 | | 2448 |
| ttc tac ccg gag cgc aac acg ccc gcc tac ttc aac agc atg atc cag<br>Phe Tyr Pro Glu Arg Asn Thr Pro Ala Tyr Phe Asn Ser Met Ile Gln<br>                       820                       825                       830 | | 2496 |
| ggc tac acc atg agg agg gac tag<br>Gly Tyr Thr Met Arg Arg Asp<br>        835 | | 2520 |

<210> SEQ ID NO 52
<211> LENGTH: 839
<212> TYPE: PRT
<213> ORGANISM: Homo sapiens

<400> SEQUENCE: 52

Met Gly Pro Arg Ala Lys Thr Ile Ser Ser Leu Phe Phe Leu Leu Trp
1               5                   10                  15

Val Leu Ala Glu Pro Ala Glu Asn Ser Asp Phe Tyr Leu Pro Gly Asp
            20                  25                  30

Tyr Leu Leu Gly Gly Leu Phe Ser Leu His Ala Asn Met Lys Gly Ile
        35                  40                  45

Val His Leu Asn Phe Leu Gln Val Pro Met Cys Lys Glu Tyr Glu Val
    50                  55                  60

Lys Val Ile Gly Tyr Asn Leu Met Gln Ala Met Arg Phe Ala Val Glu
65                  70                  75                  80

```
Glu Ile Asn Asn Asp Ser Ser Leu Leu Pro Gly Val Leu Leu Gly Tyr
                 85                  90                  95

Glu Ile Val Asp Val Cys Tyr Ile Ser Asn Asn Val Gln Pro Val Leu
            100                 105                 110

Tyr Phe Leu Ala His Glu Asp Asn Leu Leu Pro Ile Gln Glu Asp Tyr
        115                 120                 125

Ser Asn Tyr Ile Ser Arg Val Ala Val Ile Gly Pro Asp Asn Ser
    130                 135                 140

Glu Ser Val Met Thr Val Ala Asn Phe Leu Ser Leu Phe Leu Leu Pro
145                 150                 155                 160

Gln Ile Thr Tyr Ser Ala Ile Ser Asp Glu Leu Arg Asp Lys Val Arg
                165                 170                 175

Phe Pro Ala Leu Leu Arg Thr Thr Pro Ser Ala Asp His His Ile Glu
            180                 185                 190

Ala Met Val Gln Leu Met Leu His Phe Arg Trp Asn Trp Ile Ile Val
        195                 200                 205

Leu Val Ser Ser Asp Thr Tyr Gly Arg Asp Asn Gly Gln Leu Leu Gly
    210                 215                 220

Glu Arg Val Ala Arg Arg Asp Ile Cys Ile Ala Phe Gln Glu Thr Leu
225                 230                 235                 240

Pro Thr Leu Gln Pro Asn Gln Asn Met Thr Ser Glu Glu Arg Gln Arg
                245                 250                 255

Leu Val Thr Ile Val Asp Lys Leu Gln Gln Ser Thr Ala Arg Val Val
            260                 265                 270

Val Val Phe Ser Pro Asp Leu Thr Leu Tyr His Phe Phe Asn Glu Val
        275                 280                 285

Leu Arg Gln Asn Phe Thr Gly Ala Val Trp Ile Ala Ser Glu Ser Trp
    290                 295                 300

Ala Ile Asp Pro Val Leu His Asn Leu Thr Glu Leu Arg His Leu Gly
305                 310                 315                 320

Thr Phe Leu Gly Ile Thr Ile Gln Ser Val Pro Ile Pro Gly Phe Ser
                325                 330                 335

Glu Phe Arg Glu Trp Gly Pro Gln Ala Gly Pro Pro Leu Ser Arg
            340                 345                 350

Thr Ser Gln Ser Tyr Thr Cys Asn Gln Glu Cys Asp Asn Cys Leu Asn
        355                 360                 365

Ala Thr Leu Ser Phe Asn Thr Ile Leu Arg Leu Ser Gly Glu Arg Val
    370                 375                 380

Val Tyr Ser Val Tyr Ser Ala Val Tyr Ala Val Ala His Ala Leu His
385                 390                 395                 400

Ser Leu Leu Gly Cys Asp Lys Ser Thr Cys Thr Lys Arg Val Val Tyr
                405                 410                 415

Pro Trp Gln Leu Leu Glu Glu Ile Trp Lys Val Asn Phe Thr Leu Leu
            420                 425                 430

Asp His Gln Ile Phe Phe Asp Pro Gln Gly Asp Val Ala Leu His Leu
        435                 440                 445

Glu Ile Val Gln Trp Gln Trp Asp Arg Ser Gln Asn Pro Phe Gln Ser
    450                 455                 460

Val Ala Ser Tyr Tyr Pro Leu Gln Arg Gln Leu Lys Asn Ile Gln Asp
465                 470                 475                 480

Ile Ser Trp His Thr Ile Asn Asn Thr Ile Pro Met Ser Met Cys Ser
                485                 490                 495

Lys Arg Cys Gln Ser Gly Gln Lys Lys Lys Pro Val Gly Ile His Val
```

```
                500                 505                 510
    Cys Cys Phe Glu Cys Ile Asp Cys Leu Pro Gly Thr Phe Leu Asn His
            515                 520                 525

Thr Glu Asp Glu Tyr Glu Cys Gln Ala Cys Pro Asn Asn Glu Trp Ser
        530                 535                 540

Tyr Gln Ser Glu Thr Ser Cys Phe Lys Arg Gln Leu Val Phe Leu Glu
    545                 550                 555                 560

Trp His Glu Ala Pro Thr Ile Ala Val Ala Leu Leu Ala Ala Leu Gly
                    565                 570                 575

Phe Leu Ser Thr Leu Ala Ile Leu Val Ile Phe Trp Arg His Phe Gln
                580                 585                 590

Thr Pro Ile Val Arg Ser Ala Gly Gly Pro Met Cys Phe Leu Met Leu
            595                 600                 605

Thr Leu Leu Leu Val Ala Tyr Met Val Val Pro Val Tyr Val Gly Pro
            610                 615                 620

Pro Lys Val Ser Thr Cys Leu Cys Arg Gln Ala Leu Phe Pro Leu Cys
    625                 630                 635                 640

Phe Thr Ile Cys Ile Ser Cys Ile Ala Val Arg Ser Phe Gln Ile Val
                        645                 650                 655

Cys Ala Phe Lys Met Ala Ser Arg Phe Pro Arg Ala Tyr Ser Tyr Trp
                660                 665                 670

Val Arg Tyr Gln Gly Pro Tyr Val Ser Met Ala Phe Ile Thr Val Leu
                675                 680                 685

Lys Met Val Ile Val Ile Gly Met Leu Ala Thr Gly Leu Ser Pro
    690                 695                 700

Thr Thr Arg Thr Asp Pro Asp Pro Lys Ile Thr Ile Val Ser Cys
    705                 710                 715                 720

Asn Pro Asn Tyr Arg Asn Ser Leu Leu Phe Asn Thr Ser Leu Asp Leu
                        725                 730                 735

Leu Leu Ser Val Val Gly Phe Ser Phe Ala Tyr Met Gly Lys Glu Leu
                    740                 745                 750

Pro Thr Asn Tyr Asn Glu Ala Lys Phe Ile Thr Leu Ser Met Thr Phe
            755                 760                 765

Tyr Phe Thr Ser Ser Val Ser Leu Cys Thr Phe Met Ser Ala Tyr Ser
            770                 775                 780

Gly Val Leu Val Thr Ile Val Asp Leu Leu Val Thr Val Leu Asn Leu
    785                 790                 795                 800

Leu Ala Ile Ser Leu Gly Tyr Phe Gly Pro Lys Cys Tyr Met Ile Leu
                    805                 810                 815

Phe Tyr Pro Glu Arg Asn Thr Pro Ala Tyr Phe Asn Ser Met Ile Gln
                820                 825                 830

Gly Tyr Thr Met Arg Arg Asp
            835

<210> SEQ ID NO 53
<211> LENGTH: 2532
<212> TYPE: DNA
<213> ORGANISM: Mus musculus
<220> FEATURE:
<221> NAME/KEY: CDS
<222> LOCATION: (1)..(2532)

<400> SEQUENCE: 53 atg gga ccc cag gcg agg aca ctc cat ttg ctg ttt ctc ctg ctg cat    48
Met Gly Pro Gln Ala Arg Thr Leu His Leu Leu Phe Leu Leu Leu His
1               5                  10                  15
```

```
gct ctg cct aag cca gtc atg ctg gta ggg aac tcc gac ttt cac ctg      96
Ala Leu Pro Lys Pro Val Met Leu Val Gly Asn Ser Asp Phe His Leu
         20                  25                  30 gct ggg gac tac ctc ctg ggt ggc ctc ttt acc ctc cat gcc aac gtg     144
Ala Gly Asp Tyr Leu Leu Gly Gly Leu Phe Thr Leu His Ala Asn Val
     35                  40                  45 aag agc gtc tct cac ctc agc tac ctg cag gtg ccc aag tgc aat gag     192
Lys Ser Val Ser His Leu Ser Tyr Leu Gln Val Pro Lys Cys Asn Glu
 50                  55                  60 tac aac atg aag gtc ttg ggc tac aac ctc atg cag gcc atg cga ttc     240
Tyr Asn Met Lys Val Leu Gly Tyr Asn Leu Met Gln Ala Met Arg Phe
 65                  70                  75                  80 gcc gtg gag gaa atc aac aac tgt agc tct ctg ctc ccc ggc gtg ctg     288
Ala Val Glu Glu Ile Asn Asn Cys Ser Ser Leu Leu Pro Gly Val Leu
                 85                  90                  95 ctc ggc tac gag atg gtg gat gtc tgc tac ctc tcc aac aat atc cag     336
Leu Gly Tyr Glu Met Val Asp Val Cys Tyr Leu Ser Asn Asn Ile Gln
                 100                 105                 110 cct ggg ctc tac ttc ctg tca cag ata gat gac ttc ctg ccc atc ctc     384
Pro Gly Leu Tyr Phe Leu Ser Gln Ile Asp Asp Phe Leu Pro Ile Leu
             115                 120                 125 aaa gac tac agc cag tac agg ccc caa gtg gtg gcc gtc att ggc cca     432
Lys Asp Tyr Ser Gln Tyr Arg Pro Gln Val Val Ala Val Ile Gly Pro
 130                 135                 140 gac aac tct gag tcc gcc atc acc gtg tcc aac att ctc tcc tac ttc     480
Asp Asn Ser Glu Ser Ala Ile Thr Val Ser Asn Ile Leu Ser Tyr Phe
 145                 150                 155                 160 ctc gtg cca cag gtc aca tat agc gcc atc acc gac aag ctg cga gac     528
Leu Val Pro Gln Val Thr Tyr Ser Ala Ile Thr Asp Lys Leu Arg Asp
                 165                 170                 175 aag cgg cgc ttc cct gcc atg ctg cgc act gtg ccc agc gcc acc cac     576
Lys Arg Arg Phe Pro Ala Met Leu Arg Thr Val Pro Ser Ala Thr His
                 180                 185                 190 cac atc gag gcc atg gtg caa ctg atg gtt cac ttc cag tgg aac tgg     624
His Ile Glu Ala Met Val Gln Leu Met Val His Phe Gln Trp Asn Trp
             195                 200                 205 atc gtg gtg ctg gtg agc gat gac gat tat ggc cga gag aac agc cac     672
Ile Val Val Leu Val Ser Asp Asp Asp Tyr Gly Arg Glu Asn Ser His
 210                 215                 220 ctg ctg agc cag cgt ctg acc aac act ggc gat atc tgc att gcc ttc     720
Leu Leu Ser Gln Arg Leu Thr Asn Thr Gly Asp Ile Cys Ile Ala Phe
 225                 230                 235                 240 cag gag gtt ctg cct gta cca gaa ccc aac cag gcc gtg agg cct gag     768
Gln Glu Val Leu Pro Val Pro Glu Pro Asn Gln Ala Val Arg Pro Glu
                 245                 250                 255 gag cag gac caa ctg gac aac atc ctg gac aag ctg cgg cgg acc tcg     816
Glu Gln Asp Gln Leu Asp Asn Ile Leu Asp Lys Leu Arg Arg Thr Ser
                 260                 265                 270 gcg cgt gtg gtg gtg ata ttc tcg cca gag ctg agc ctg cac aac ttc     864
Ala Arg Val Val Val Ile Phe Ser Pro Glu Leu Ser Leu His Asn Phe
             275                 280                 285 ttc cgc gag gtg ctg cgc tgg aac ttc aca ggc ttt gtg tgg att gcc     912
Phe Arg Glu Val Leu Arg Trp Asn Phe Thr Gly Phe Val Trp Ile Ala
 290                 295                 300 tct gag tcc tgg gcc atc gac cct gtt cta cac aac ctc aca gag ctg     960
Ser Glu Ser Trp Ala Ile Asp Pro Val Leu His Asn Leu Thr Glu Leu
 305                 310                 315                 320 cgc cac acg ggc act ttc ctg ggc gtc acc atc cag agg gtg tcc atc    1008
Arg His Thr Gly Thr Phe Leu Gly Val Thr Ile Gln Arg Val Ser Ile
```

-continued

```
                325                 330                 335
cct ggc ttc agc cag ttc cga gtg cgc cac gac aag cca gag tat ccc      1056
Pro Gly Phe Ser Gln Phe Arg Val Arg His Asp Lys Pro Glu Tyr Pro
            340                 345                 350 atg cct aac gag acc agc ctg agg act acc tgt aac cag gac tgt gac      1104
Met Pro Asn Glu Thr Ser Leu Arg Thr Thr Cys Asn Gln Asp Cys Asp
    355                 360                 365 gcc tgc atg aac atc acc gag tcc ttt aac aac gtt ctc atg ctt tcg      1152
Ala Cys Met Asn Ile Thr Glu Ser Phe Asn Asn Val Leu Met Leu Ser
370                 375                 380 ggg gag cgt gtg gtc tac agt gtg tac tcg gcc gtc tac gcg gta gcc      1200
Gly Glu Arg Val Val Tyr Ser Val Tyr Ser Ala Val Tyr Ala Val Ala
385                 390                 395                 400 cac acc ctc cac aga ctc ctc cac tgc aac cag gtc cgc tgc acc aag      1248
His Thr Leu His Arg Leu Leu His Cys Asn Gln Val Arg Cys Thr Lys
                405                 410                 415 caa atc gtc tat cca tgg cag cta ctc agg gag atc tgg cat gtc aac      1296
Gln Ile Val Tyr Pro Trp Gln Leu Leu Arg Glu Ile Trp His Val Asn
            420                 425                 430 ttc acg ctc ctg ggc aac cag ctc ttc ttc gac gaa caa ggg gac atg      1344
Phe Thr Leu Leu Gly Asn Gln Leu Phe Phe Asp Glu Gln Gly Asp Met
        435                 440                 445 ccg atg ctc ctg gac atc atc cag tgg caa tgg ggc ctg agc cag aac      1392
Pro Met Leu Leu Asp Ile Ile Gln Trp Gln Trp Gly Leu Ser Gln Asn
    450                 455                 460 ccc ttc caa agc atc gcc tcc tac tcc ccc acc gag acg agg ctg acc      1440
Pro Phe Gln Ser Ile Ala Ser Tyr Ser Pro Thr Glu Thr Arg Leu Thr
465                 470                 475                 480 tac att agc aat gtg tcc tgg tac acc ccc aac aac acg gtc ccc ata      1488
Tyr Ile Ser Asn Val Ser Trp Tyr Thr Pro Asn Asn Thr Val Pro Ile
                485                 490                 495 tcc atg tgt tct aag agt tgc cag cct ggg caa atg aaa aaa ccc ata      1536
Ser Met Cys Ser Lys Ser Cys Gln Pro Gly Gln Met Lys Lys Pro Ile
            500                 505                 510 ggc ctc cac ccg tgc tgc ttc gag tgt gtg gac tgt ccg ccg ggc acc      1584
Gly Leu His Pro Cys Cys Phe Glu Cys Val Asp Cys Pro Pro Gly Thr
        515                 520                 525 tac ctc aac cga tca gta gat gag ttt aac tgt ctg tcc tgc ccg ggt      1632
Tyr Leu Asn Arg Ser Val Asp Glu Phe Asn Cys Leu Ser Cys Pro Gly
    530                 535                 540 tcc atg tgg tct tac aag aac aac atc gct tgc ttc aag cgg cgg ctg      1680
Ser Met Trp Ser Tyr Lys Asn Asn Ile Ala Cys Phe Lys Arg Arg Leu
545                 550                 555                 560 gcc ttc ctg gag tgg cac gaa gtg ccc act atc gtg gtg acc atc ctg      1728
Ala Phe Leu Glu Trp His Glu Val Pro Thr Ile Val Val Thr Ile Leu
                565                 570                 575 gcc gcc ctg ggc ttc atc agt acg ctg gcc att ctg ctc atc ttc tgg      1776
Ala Ala Leu Gly Phe Ile Ser Thr Leu Ala Ile Leu Leu Ile Phe Trp
            580                 585                 590 aga cat ttc cag acg ccc atg gtg cgc tcg gcg ggc ggc ccc atg tgc      1824
Arg His Phe Gln Thr Pro Met Val Arg Ser Ala Gly Gly Pro Met Cys
        595                 600                 605 ttc ctg atg ctg gtg ccc ctg ctg ctg gcg ttc ggg atg gtc ccc gtg      1872
Phe Leu Met Leu Val Pro Leu Leu Leu Ala Phe Gly Met Val Pro Val
    610                 615                 620 tat gtg ggc ccc ccc acg gtc ttc tcc tgt ttc tgc cgc cag gct ttc      1920
Tyr Val Gly Pro Pro Thr Val Phe Ser Cys Phe Cys Arg Gln Ala Phe
625                 630                 635                 640 ttc acc gtt tgc ttc tcc gtc tgc ctc tcc tgc atc acg gtg cgc tcc      1968
```

-continued

```
                Phe Thr Val Cys Phe Ser Val Cys Leu Ser Cys Ile Thr Val Arg Ser
                                645                 650                 655 ttc cag att gtg tgc gtc ttc aag atg gcc aga cgc ctg cca agc gcc          2016
Phe Gln Ile Val Cys Val Phe Lys Met Ala Arg Arg Leu Pro Ser Ala
        660                 665                 670 tac ggt ttc tgg atg cgt tac cac ggg ccc tac gtc ttt gtg gcc ttc          2064
Tyr Gly Phe Trp Met Arg Tyr His Gly Pro Tyr Val Phe Val Ala Phe
    675                 680                 685 atc acg gcc gtc aag gtg gcc ctg gtg gca ggc aac atg ctg gcc acc          2112
Ile Thr Ala Val Lys Val Ala Leu Val Ala Gly Asn Met Leu Ala Thr
690                 695                 700 acc atc aac ccc att ggc cgg acc gac ccc gat gac ccc aat atc ata          2160
Thr Ile Asn Pro Ile Gly Arg Thr Asp Pro Asp Asp Pro Asn Ile Ile
705                 710                 715                 720 atc ctc tcc tgc cac cct aac tac cgc aac ggg cta ctc ttc aac acc          2208
Ile Leu Ser Cys His Pro Asn Tyr Arg Asn Gly Leu Leu Phe Asn Thr
                725                 730                 735 agc atg gac ttg ctg ctg tcc gtg ctg ggt ttc agc ttc gcg tac gtg          2256
Ser Met Asp Leu Leu Leu Ser Val Leu Gly Phe Ser Phe Ala Tyr Val
            740                 745                 750 ggc aag gaa ctg ccc acc aac tac aac gaa gcc aag ttc atc acc ctc          2304
Gly Lys Glu Leu Pro Thr Asn Tyr Asn Glu Ala Lys Phe Ile Thr Leu
        755                 760                 765 agc atg acc ttc tcc ttc acc tcc tcc atc tcc ctc tgc acg ttc atg          2352
Ser Met Thr Phe Ser Phe Thr Ser Ser Ile Ser Leu Cys Thr Phe Met
    770                 775                 780 tct gtc cac gat ggc gtg ctg gtc acc atc atg gat ctc ctg gtc act          2400
Ser Val His Asp Gly Val Leu Val Thr Ile Met Asp Leu Leu Val Thr
785                 790                 795                 800 gtg ctc aac ttt ctg gcc atc ggc ttg ggg tac ttt ggc ccc aag tgt          2448
Val Leu Asn Phe Leu Ala Ile Gly Leu Gly Tyr Phe Gly Pro Lys Cys
                805                 810                 815 tac atg atc ctt ttc tac ccg gag cgc aac act tca gct tat ttc aat          2496
Tyr Met Ile Leu Phe Tyr Pro Glu Arg Asn Thr Ser Ala Tyr Phe Asn
            820                 825                 830 agc atg att cag ggc tac acg atg agg aag agc tag                          2532
Ser Met Ile Gln Gly Tyr Thr Met Arg Lys Ser
        835                 840
```

<210> SEQ ID NO 54
<211> LENGTH: 843
<212> TYPE: PRT
<213> ORGANISM: Mus musculus

<400> SEQUENCE: 54

```
Met Gly Pro Gln Ala Arg Thr Leu His Leu Leu Phe Leu Leu Leu His
1               5                   10                  15

Ala Leu Pro Lys Pro Val Met Leu Val Gly Asn Ser Asp Phe His Leu
            20                  25                  30

Ala Gly Asp Tyr Leu Leu Gly Gly Leu Phe Thr Leu His Ala Asn Val
        35                  40                  45

Lys Ser Val Ser His Leu Ser Tyr Leu Gln Val Pro Lys Cys Asn Glu
    50                  55                  60

Tyr Asn Met Lys Val Leu Gly Tyr Asn Leu Met Gln Ala Met Arg Phe
65                  70                  75                  80

Ala Val Glu Glu Ile Asn Asn Cys Ser Ser Leu Leu Pro Gly Val Leu
                85                  90                  95

Leu Gly Tyr Glu Met Val Asp Val Cys Tyr Leu Ser Asn Asn Ile Gln
            100                 105                 110
```

-continued

```
Pro Gly Leu Tyr Phe Leu Ser Gln Ile Asp Asp Phe Leu Pro Ile Leu
        115                 120                 125

Lys Asp Tyr Ser Gln Tyr Arg Pro Gln Val Val Ala Val Ile Gly Pro
    130                 135                 140

Asp Asn Ser Glu Ser Ala Ile Thr Val Ser Asn Ile Leu Ser Tyr Phe
145                 150                 155                 160

Leu Val Pro Gln Val Thr Tyr Ser Ala Ile Thr Asp Lys Leu Arg Asp
                165                 170                 175

Lys Arg Arg Phe Pro Ala Met Leu Arg Thr Val Pro Ser Ala Thr His
                180                 185                 190

His Ile Glu Ala Met Val Gln Leu Met Val His Phe Gln Trp Asn Trp
            195                 200                 205

Ile Val Val Leu Val Ser Asp Asp Tyr Gly Arg Glu Asn Ser His
        210                 215                 220

Leu Leu Ser Gln Arg Leu Thr Asn Thr Gly Asp Ile Cys Ile Ala Phe
225                 230                 235                 240

Gln Glu Val Leu Pro Val Pro Glu Pro Asn Gln Ala Val Arg Pro Glu
                245                 250                 255

Glu Gln Asp Gln Leu Asp Asn Ile Leu Asp Lys Leu Arg Thr Ser
            260                 265                 270

Ala Arg Val Val Ile Phe Ser Pro Glu Leu Ser Leu His Asn Phe
    275                 280                 285

Phe Arg Glu Val Leu Arg Trp Asn Phe Thr Gly Phe Val Trp Ile Ala
    290                 295                 300

Ser Glu Ser Trp Ala Ile Asp Pro Val Leu His Asn Leu Thr Glu Leu
305                 310                 315                 320

Arg His Thr Gly Thr Phe Leu Gly Val Thr Ile Gln Arg Val Ser Ile
                325                 330                 335

Pro Gly Phe Ser Gln Phe Arg Val Arg His Asp Lys Pro Glu Tyr Pro
                340                 345                 350

Met Pro Asn Glu Thr Ser Leu Arg Thr Thr Cys Asn Gln Asp Cys Asp
            355                 360                 365

Ala Cys Met Asn Ile Thr Glu Ser Phe Asn Asn Val Leu Met Leu Ser
    370                 375                 380

Gly Glu Arg Val Val Tyr Ser Val Tyr Ser Ala Val Tyr Ala Val Ala
385                 390                 395                 400

His Thr Leu His Arg Leu Leu His Cys Asn Gln Val Arg Cys Thr Lys
                405                 410                 415

Gln Ile Val Tyr Pro Trp Gln Leu Leu Arg Glu Ile Trp His Val Asn
                420                 425                 430

Phe Thr Leu Leu Gly Asn Gln Leu Phe Phe Asp Glu Gln Gly Asp Met
            435                 440                 445

Pro Met Leu Leu Asp Ile Ile Gln Trp Gln Trp Gly Leu Ser Gln Asn
450                 455                 460

Pro Phe Gln Ser Ile Ala Ser Tyr Ser Pro Thr Glu Thr Arg Leu Thr
465                 470                 475                 480

Tyr Ile Ser Asn Val Ser Trp Tyr Thr Pro Asn Asn Thr Val Pro Ile
                485                 490                 495

Ser Met Cys Ser Lys Ser Cys Gln Pro Gly Gln Met Lys Lys Pro Ile
                500                 505                 510

Gly Leu His Pro Cys Cys Phe Glu Cys Val Asp Cys Pro Pro Gly Thr
            515                 520                 525
```

```
Tyr Leu Asn Arg Ser Val Asp Glu Phe Asn Cys Leu Ser Cys Pro Gly
    530                 535                 540
Ser Met Trp Ser Tyr Lys Asn Asn Ile Ala Cys Phe Lys Arg Arg Leu
545                 550                 555                 560
Ala Phe Leu Glu Trp His Glu Val Pro Thr Ile Val Val Thr Ile Leu
                565                 570                 575
Ala Ala Leu Gly Phe Ile Ser Thr Leu Ala Ile Leu Leu Ile Phe Trp
            580                 585                 590
Arg His Phe Gln Thr Pro Met Val Arg Ser Ala Gly Gly Pro Met Cys
        595                 600                 605
Phe Leu Met Leu Val Pro Leu Leu Leu Ala Phe Gly Met Val Pro Val
    610                 615                 620
Tyr Val Gly Pro Pro Thr Val Phe Ser Cys Phe Cys Arg Gln Ala Phe
625                 630                 635                 640
Phe Thr Val Cys Phe Ser Val Cys Leu Ser Cys Ile Thr Val Arg Ser
                645                 650                 655
Phe Gln Ile Val Cys Val Phe Lys Met Ala Arg Arg Leu Pro Ser Ala
            660                 665                 670
Tyr Gly Phe Trp Met Arg Tyr His Gly Pro Tyr Val Phe Val Ala Phe
        675                 680                 685
Ile Thr Ala Val Lys Val Ala Leu Val Ala Gly Asn Met Leu Ala Thr
    690                 695                 700
Thr Ile Asn Pro Ile Gly Arg Thr Asp Pro Asp Pro Asn Ile Ile
705                 710                 715                 720
Ile Leu Ser Cys His Pro Asn Tyr Arg Asn Gly Leu Leu Phe Asn Thr
                725                 730                 735
Ser Met Asp Leu Leu Ser Val Leu Gly Phe Ser Phe Ala Tyr Val
            740                 745                 750
Gly Lys Glu Leu Pro Thr Asn Tyr Asn Glu Ala Lys Phe Ile Thr Leu
        755                 760                 765
Ser Met Thr Phe Ser Phe Thr Ser Ser Ile Ser Leu Cys Thr Phe Met
    770                 775                 780
Ser Val His Asp Gly Val Leu Val Thr Ile Met Asp Leu Leu Val Thr
785                 790                 795                 800
Val Leu Asn Phe Leu Ala Ile Gly Leu Gly Tyr Phe Gly Pro Lys Cys
                805                 810                 815
Tyr Met Ile Leu Phe Tyr Pro Glu Arg Asn Thr Ser Ala Tyr Phe Asn
            820                 825                 830
Ser Met Ile Gln Gly Tyr Thr Met Arg Lys Ser
        835                 840

<210> SEQ ID NO 55
<211> LENGTH: 2559
<212> TYPE: DNA
<213> ORGANISM: Homo sapiens
<220> FEATURE:
<221> NAME/KEY: CDS
<222> LOCATION: (1)..(2559)

<400> SEQUENCE: 55 atg ctg ggc cct gct gtc ctg ggc ctc agc ctc tgg gct ctc ctg cac    48
Met Leu Gly Pro Ala Val Leu Gly Leu Ser Leu Trp Ala Leu Leu His
1               5                   10                  15 cct ggg acg ggg gcc cca ttg tgc ctg tca cag caa ctt agg atg aag    96
Pro Gly Thr Gly Ala Pro Leu Cys Leu Ser Gln Gln Leu Arg Met Lys
                20                  25                  30
```

-continued

| | | |
|---|---|---|
| ggg gac tac gtg ctg ggg ggg ctg ttc ccc ctg ggc gag gcc gag gag<br>Gly Asp Tyr Val Leu Gly Gly Leu Phe Pro Leu Gly Glu Ala Glu Glu<br>35                            40                       45 | 144 | |
| gct ggc ctc cgc agc cgg aca cgg ccc agc agc cct gtg tgc acc agg<br>Ala Gly Leu Arg Ser Arg Thr Arg Pro Ser Ser Pro Val Cys Thr Arg<br>50                           55                       60 | 192 | |
| ttc tcc tca aac ggc ctg ctc tgg gca ctg gcc atg aaa atg gcc gtg<br>Phe Ser Ser Asn Gly Leu Leu Trp Ala Leu Ala Met Lys Met Ala Val<br>65                           70                       75                       80 | 240 | |
| gag gag atc aac aac aag tcg gat ctg ctg ccc ggg ctg cgc ctg ggc<br>Glu Glu Ile Asn Asn Lys Ser Asp Leu Leu Pro Gly Leu Arg Leu Gly<br>                         85                       90                       95 | 288 | |
| tac gac ctc ttt gat acg tgc tcg gag cct gtg gtg gcc atg aag ccc<br>Tyr Asp Leu Phe Asp Thr Cys Ser Glu Pro Val Val Ala Met Lys Pro<br>                       100                    105                    110 | 336 | |
| agc ctc atg ttc ctg gcc aag gca ggc agc cgc gac atc gcc gcc tac<br>Ser Leu Met Phe Leu Ala Lys Ala Gly Ser Arg Asp Ile Ala Ala Tyr<br>                 115                    120                    125 | 384 | |
| tgc aac tac acg cag tac cag ccc cgt gtg ctg gct gtc atc ggg ccc<br>Cys Asn Tyr Thr Gln Tyr Gln Pro Arg Val Leu Ala Val Ile Gly Pro<br>130                           135                       140 | 432 | |
| cac tcg tca gag ctc gcc atg gtc acc ggc aag ttc ttc agc ttc ttc<br>His Ser Ser Glu Leu Ala Met Val Thr Gly Lys Phe Phe Ser Phe Phe<br>145                         150                    155                    160 | 480 | |
| ctc atg ccc cag gtc agc tac ggt gct agc atg gag ctg ctg agc gcc<br>Leu Met Pro Gln Val Ser Tyr Gly Ala Ser Met Glu Leu Leu Ser Ala<br>                 165                    170                    175 | 528 | |
| cgg gag acc ttc ccc tcc ttc ttc cgc acc gtg ccc agc gac cgt gtg<br>Arg Glu Thr Phe Pro Ser Phe Phe Arg Thr Val Pro Ser Asp Arg Val<br>180                           185                       190 | 576 | |
| cag ctg acg gcc gcc gcg gag ctg ctg cag gag ttc ggc tgg aac tgg<br>Gln Leu Thr Ala Ala Ala Glu Leu Leu Gln Glu Phe Gly Trp Asn Trp<br>                 195                    200                    205 | 624 | |
| gtg gcc gcc ctg ggc agc gac gac gag tac ggc cgg cag ggc ctg agc<br>Val Ala Ala Leu Gly Ser Asp Asp Glu Tyr Gly Arg Gln Gly Leu Ser<br>210                           215                    220 | 672 | |
| atc ttc tcg gcc ctg gcc gcg gca cgc ggc atc tgc atc gcg cac gag<br>Ile Phe Ser Ala Leu Ala Ala Ala Arg Gly Ile Cys Ile Ala His Glu<br>225                           230                    235                    240 | 720 | |
| ggc ctg gtg ccg ctg ccc cgt gcc gat gac tcg cgg ctg ggg aag gtg<br>Gly Leu Val Pro Leu Pro Arg Ala Asp Asp Ser Arg Leu Gly Lys Val<br>                 245                    250                    255 | 768 | |
| cag gac gtc ctg cac cag gtg aac cag agc agc gtg cag gtg gtg ctg<br>Gln Asp Val Leu His Gln Val Asn Gln Ser Ser Val Gln Val Val Leu<br>                 260                    265                    270 | 816 | |
| ctg ttc gcc tcc gtg cac gcc gcc cac gcc ctc ttc aac tac agc atc<br>Leu Phe Ala Ser Val His Ala Ala His Ala Leu Phe Asn Tyr Ser Ile<br>275                           280                    285 | 864 | |
| agc agc agg ctc tcg ccc aag gtg tgg gtg gcc agc gag gcc tgg ctg<br>Ser Ser Arg Leu Ser Pro Lys Val Trp Val Ala Ser Glu Ala Trp Leu<br>290                           295                    300 | 912 | |
| acc tct gac ctg gtc atg ggg ctg ccc ggc atg gcc cag atg ggc acg<br>Thr Ser Asp Leu Val Met Gly Leu Pro Gly Met Ala Gln Met Gly Thr<br>305                         310                    315                    320 | 960 | |
| gtg ctt ggc ttc ctc cag agg ggt gcc cag ctg cac gag ttc ccc cag<br>Val Leu Gly Phe Leu Gln Arg Gly Ala Gln Leu His Glu Phe Pro Gln<br>                 325                    330                    335 | 1008 | |
| tac gtg aag acg cac ctg gcc ctg gcc acc gac ccg gcc ttc tgc tct<br>Tyr Val Lys Thr His Leu Ala Leu Ala Thr Asp Pro Ala Phe Cys Ser<br>                 340                    345                    350 | 1056 | |

```
gcc ctg ggc gag agg gag cag ggt ctg gag gag gac gtg gtg ggc cag    1104
Ala Leu Gly Glu Arg Glu Gln Gly Leu Glu Glu Asp Val Val Gly Gln
            355                 360                 365 cgc tgc ccg cag tgt gac tgc atc acg ctg cag aac gtg agc gca ggg    1152
Arg Cys Pro Gln Cys Asp Cys Ile Thr Leu Gln Asn Val Ser Ala Gly
        370                 375                 380 cta aat cac cac cag acg ttc tct gtc tac gca gct gtg tat agc gtg    1200
Leu Asn His His Gln Thr Phe Ser Val Tyr Ala Ala Val Tyr Ser Val
385                 390                 395                 400 gcc cag gcc ctg cac aac act ctt cag tgc aac gcc tca ggc tgc ccc    1248
Ala Gln Ala Leu His Asn Thr Leu Gln Cys Asn Ala Ser Gly Cys Pro
                405                 410                 415 gcg cag gac ccc gtg aag ccc tgg cag ctc ctg gag aac atg tac aac    1296
Ala Gln Asp Pro Val Lys Pro Trp Gln Leu Leu Glu Asn Met Tyr Asn
            420                 425                 430 ctg acc ttc cac gtg ggc ggg ctg ccg ctg cgg ttc gac agc agc gga    1344
Leu Thr Phe His Val Gly Gly Leu Pro Leu Arg Phe Asp Ser Ser Gly
        435                 440                 445 aac gtg gac atg gag tac gac ctg aag ctg tgg gtg tgg cag ggc tca    1392
Asn Val Asp Met Glu Tyr Asp Leu Lys Leu Trp Val Trp Gln Gly Ser
450                 455                 460 gtg ccc agg ctc cac gac gtg ggc agg ttc aac ggc agc ctc agg aca    1440
Val Pro Arg Leu His Asp Val Gly Arg Phe Asn Gly Ser Leu Arg Thr
465                 470                 475                 480 gag cgc ctg aag atc cgc tgg cac acg tct gac aac cag aag ccc gtg    1488
Glu Arg Leu Lys Ile Arg Trp His Thr Ser Asp Asn Gln Lys Pro Val
                485                 490                 495 tcc cgg tgc tcg cgg cag tgc cag gag ggc cag gtg cgc cgg gtc aag    1536
Ser Arg Cys Ser Arg Gln Cys Gln Glu Gly Gln Val Arg Arg Val Lys
            500                 505                 510 ggg ttc cac tcc tgc tgc tac gac tgt gtg gac tgc gag gcg ggc agc    1584
Gly Phe His Ser Cys Cys Tyr Asp Cys Val Asp Cys Glu Ala Gly Ser
        515                 520                 525 tac cgg caa aac cca gac gac atc gcc tgc acc ttt tgt ggc cag gat    1632
Tyr Arg Gln Asn Pro Asp Asp Ile Ala Cys Thr Phe Cys Gly Gln Asp
    530                 535                 540 gag tgg tcc ccg gag cga agc aca cgc tgc ttc cgc cgc agg tct cgg    1680
Glu Trp Ser Pro Glu Arg Ser Thr Arg Cys Phe Arg Arg Arg Ser Arg
545                 550                 555                 560 ttc ctg gca tgg ggc gag ccg gct gtg ctg ctg ctc ctg ctg ctg        1728
Phe Leu Ala Trp Gly Glu Pro Ala Val Leu Leu Leu Leu Leu Leu
                565                 570                 575 agc ctg gcg ctg ggc ctt gtg ctg gct gct ttg ggg ctg ttc gtt cac    1776
Ser Leu Ala Leu Gly Leu Val Leu Ala Ala Leu Gly Leu Phe Val His
            580                 585                 590 cat cgg gac agc cca ctg gtt cag gcc tcg ggg ggg ccc ctg gcc tgc    1824
His Arg Asp Ser Pro Leu Val Gln Ala Ser Gly Gly Pro Leu Ala Cys
        595                 600                 605 ttt ggc ctg gtg tgc ctg ggc ctg gtc tgc ctc agc gtc ctc ctg ttc    1872
Phe Gly Leu Val Cys Leu Gly Leu Val Cys Leu Ser Val Leu Leu Phe
    610                 615                 620 cct ggc cag ccc agc cct gcc cga tgc ctg gcc cag cag ccc ttg tcc    1920
Pro Gly Gln Pro Ser Pro Ala Arg Cys Leu Ala Gln Gln Pro Leu Ser
625                 630                 635                 640 cac ctc ccg ctc acg ggc tgc ctg agc aca ctc ttc ctg cag gcg gcc    1968
His Leu Pro Leu Thr Gly Cys Leu Ser Thr Leu Phe Leu Gln Ala Ala
                645                 650                 655 gag atc ttc gtg gag tca gaa ctg cct ctg agc tgg gca gac cgg ctg    2016
Glu Ile Phe Val Glu Ser Glu Leu Pro Leu Ser Trp Ala Asp Arg Leu
```

```
                     660                 665                 670
agt ggc tgc ctg cgg ggg ccc tgg gcc tgg ctg gtg gtg ctg ctg gcc       2064
Ser Gly Cys Leu Arg Gly Pro Trp Ala Trp Leu Val Val Leu Leu Ala
            675                 680                 685 atg ctg gtg gag gtc gca ctg tgc acc tgg tac ctg gtg gcc ttc ccg       2112
Met Leu Val Glu Val Ala Leu Cys Thr Trp Tyr Leu Val Ala Phe Pro
690                 695                 700 ccg gag gtg gtg acg gac tgg cac atg ctg ccc acg gag gcg ctg gtg       2160
Pro Glu Val Val Thr Asp Trp His Met Leu Pro Thr Glu Ala Leu Val
705                 710                 715                 720 cac tgc cgc aca cgc tcc tgg gtc agc ttc ggc cta gcg cac gcc acc       2208
His Cys Arg Thr Arg Ser Trp Val Ser Phe Gly Leu Ala His Ala Thr
                725                 730                 735 aat gcc acg ctg gcc ttt ctc tgc ttc ctg ggc act ttc ctg gtg cgg       2256
Asn Ala Thr Leu Ala Phe Leu Cys Phe Leu Gly Thr Phe Leu Val Arg
            740                 745                 750 agc cag ccg ggc cgc tac aac cgt gcc cgt ggc ctc acc ttt gcc atg       2304
Ser Gln Pro Gly Arg Tyr Asn Arg Ala Arg Gly Leu Thr Phe Ala Met
        755                 760                 765 ctg gcc tac ttc atc acc tgg gtc tcc ttt gtg ccc ctc ctg gcc aat       2352
Leu Ala Tyr Phe Ile Thr Trp Val Ser Phe Val Pro Leu Leu Ala Asn
770                 775                 780 gtg cag gtg gtc ctc agg ccc gcc gtg cag atg ggc gcc ctg ctc           2400
Val Gln Val Val Leu Arg Pro Ala Val Gln Met Gly Ala Leu Leu Leu
785                 790                 795                 800 tgt gtc ctg ggc atc ctg gct gcc ttc cac ctg ccc agg tgt tac ctg       2448
Cys Val Leu Gly Ile Leu Ala Ala Phe His Leu Pro Arg Cys Tyr Leu
                805                 810                 815 ctc atg cgg cag cca ggg ctc aac acc ccc gag ttc ttc ctg gga ggg       2496
Leu Met Arg Gln Pro Gly Leu Asn Thr Pro Glu Phe Phe Leu Gly Gly
            820                 825                 830 ggc cct ggg gat gcc caa ggc cag aat gac ggg aac aca gga aat cag       2544
Gly Pro Gly Asp Ala Gln Gly Gln Asn Asp Gly Asn Thr Gly Asn Gln
        835                 840                 845 ggg aaa cat gag tga                                                    2559
Gly Lys His Glu
    850

<210> SEQ ID NO 56
<211> LENGTH: 852
<212> TYPE: PRT
<213> ORGANISM: Homo sapiens

<400> SEQUENCE: 56

Met Leu Gly Pro Ala Val Leu Gly Leu Ser Leu Trp Ala Leu Leu His
1               5                   10                  15

Pro Gly Thr Gly Ala Pro Leu Cys Leu Ser Gln Gln Leu Arg Met Lys
            20                  25                  30

Gly Asp Tyr Val Leu Gly Gly Leu Phe Pro Leu Gly Glu Ala Glu Glu
        35                  40                  45

Ala Gly Leu Arg Ser Arg Thr Arg Pro Ser Ser Pro Val Cys Thr Arg
    50                  55                  60

Phe Ser Ser Asn Gly Leu Leu Trp Ala Leu Ala Met Lys Met Ala Val
65                  70                  75                  80

Glu Glu Ile Asn Asn Lys Ser Asp Leu Leu Pro Gly Leu Arg Leu Gly
                85                  90                  95

Tyr Asp Leu Phe Asp Thr Cys Ser Glu Pro Val Val Ala Met Lys Pro
            100                 105                 110
```

```
Ser Leu Met Phe Leu Ala Lys Ala Gly Ser Arg Asp Ile Ala Ala Tyr
        115                 120                 125

Cys Asn Tyr Thr Gln Tyr Gln Pro Arg Val Leu Ala Val Ile Gly Pro
    130                 135                 140

His Ser Ser Glu Leu Ala Met Val Thr Gly Lys Phe Phe Ser Phe Phe
145                 150                 155                 160

Leu Met Pro Gln Val Ser Tyr Gly Ala Ser Met Glu Leu Leu Ser Ala
                165                 170                 175

Arg Glu Thr Phe Pro Ser Phe Phe Arg Thr Val Pro Ser Asp Arg Val
                180                 185                 190

Gln Leu Thr Ala Ala Ala Glu Leu Leu Gln Glu Phe Gly Trp Asn Trp
                195                 200                 205

Val Ala Ala Leu Gly Ser Asp Asp Glu Tyr Gly Arg Gln Gly Leu Ser
    210                 215                 220

Ile Phe Ser Ala Leu Ala Ala Arg Gly Ile Cys Ile Ala His Glu
225                 230                 235                 240

Gly Leu Val Pro Leu Pro Arg Ala Asp Asp Ser Arg Leu Gly Lys Val
                245                 250                 255

Gln Asp Val Leu His Gln Val Asn Gln Ser Ser Val Gln Val Val Leu
                260                 265                 270

Leu Phe Ala Ser Val His Ala Ala His Ala Leu Phe Asn Tyr Ser Ile
    275                 280                 285

Ser Ser Arg Leu Ser Pro Lys Val Trp Val Ala Ser Glu Ala Trp Leu
    290                 295                 300

Thr Ser Asp Leu Val Met Gly Leu Pro Gly Met Ala Gln Met Gly Thr
305                 310                 315                 320

Val Leu Gly Phe Leu Gln Arg Gly Ala Gln Leu His Glu Phe Pro Gln
                325                 330                 335

Tyr Val Lys Thr His Leu Ala Leu Ala Thr Asp Pro Ala Phe Cys Ser
                340                 345                 350

Ala Leu Gly Glu Arg Glu Gln Gly Leu Glu Glu Asp Val Val Gly Gln
                355                 360                 365

Arg Cys Pro Gln Cys Asp Cys Ile Thr Leu Gln Asn Val Ser Ala Gly
    370                 375                 380

Leu Asn His His Gln Thr Phe Ser Val Tyr Ala Ala Val Tyr Ser Val
385                 390                 395                 400

Ala Gln Ala Leu His Asn Thr Leu Gln Cys Asn Ala Ser Gly Cys Pro
                405                 410                 415

Ala Gln Asp Pro Val Lys Pro Trp Gln Leu Leu Glu Asn Met Tyr Asn
                420                 425                 430

Leu Thr Phe His Val Gly Gly Leu Pro Leu Arg Phe Asp Ser Ser Gly
    435                 440                 445

Asn Val Asp Met Glu Tyr Asp Leu Lys Leu Trp Val Trp Gln Gly Ser
    450                 455                 460

Val Pro Arg Leu His Asp Val Gly Arg Phe Asn Gly Ser Leu Arg Thr
465                 470                 475                 480

Glu Arg Leu Lys Ile Arg Trp His Thr Ser Asp Asn Gln Lys Pro Val
                485                 490                 495

Ser Arg Cys Ser Arg Gln Cys Gln Glu Gly Gln Val Arg Arg Val Lys
                500                 505                 510

Gly Phe His Ser Cys Cys Tyr Asp Cys Val Asp Cys Glu Ala Gly Ser
    515                 520                 525

Tyr Arg Gln Asn Pro Asp Asp Ile Ala Cys Thr Phe Cys Gly Gln Asp
```

```
        530                 535                 540
Glu Trp Ser Pro Glu Arg Ser Thr Arg Cys Phe Arg Arg Ser Arg
545                 550                 555                 560

Phe Leu Ala Trp Gly Glu Pro Ala Val Leu Leu Leu Leu Leu Leu
                565                 570                 575

Ser Leu Ala Leu Gly Leu Val Leu Ala Leu Gly Leu Phe Val His
                580                 585                 590

His Arg Asp Ser Pro Leu Val Gln Ala Ser Gly Gly Pro Leu Ala Cys
                595                 600                 605

Phe Gly Leu Val Cys Leu Gly Leu Val Cys Leu Ser Val Leu Leu Phe
        610                 615                 620

Pro Gly Gln Pro Ser Pro Ala Arg Cys Leu Ala Gln Gln Pro Leu Ser
625                 630                 635                 640

His Leu Pro Leu Thr Gly Cys Leu Ser Thr Leu Phe Leu Gln Ala Ala
                645                 650                 655

Glu Ile Phe Val Glu Ser Glu Leu Pro Leu Ser Trp Ala Asp Arg Leu
                660                 665                 670

Ser Gly Cys Leu Arg Gly Pro Trp Ala Trp Leu Val Val Leu Leu Ala
                675                 680                 685

Met Leu Val Glu Val Ala Leu Cys Thr Trp Tyr Leu Val Ala Phe Pro
690                 695                 700

Pro Glu Val Val Thr Asp Trp His Met Leu Pro Thr Glu Ala Leu Val
705                 710                 715                 720

His Cys Arg Thr Arg Ser Trp Val Ser Phe Gly Leu Ala His Ala Thr
                725                 730                 735

Asn Ala Thr Leu Ala Phe Leu Cys Phe Leu Gly Thr Phe Leu Val Arg
                740                 745                 750

Ser Gln Pro Gly Arg Tyr Asn Arg Ala Arg Gly Leu Thr Phe Ala Met
                755                 760                 765

Leu Ala Tyr Phe Ile Thr Trp Val Ser Phe Val Pro Leu Leu Ala Asn
        770                 775                 780

Val Gln Val Val Leu Arg Pro Ala Val Gln Met Gly Ala Leu Leu Leu
785                 790                 795                 800

Cys Val Leu Gly Ile Leu Ala Ala Phe His Leu Pro Arg Cys Tyr Leu
                805                 810                 815

Leu Met Arg Gln Pro Gly Leu Asn Thr Pro Glu Phe Phe Leu Gly Gly
                820                 825                 830

Gly Pro Gly Asp Ala Gln Gly Gln Asn Asp Gly Asn Thr Gly Asn Gln
        835                 840                 845

Gly Lys His Glu
    850

<210> SEQ ID NO 57
<211> LENGTH: 2577
<212> TYPE: DNA
<213> ORGANISM: Mus musculus
<220> FEATURE:
<221> NAME/KEY: CDS
<222> LOCATION: (1)..(2577)

<400> SEQUENCE: 57 atg cca gct ttg gct atc atg ggt ctc agc ctg gct gct ttc ctg gag    48
Met Pro Ala Leu Ala Ile Met Gly Leu Ser Leu Ala Ala Phe Leu Glu
1               5                   10                  15 ctt ggg atg ggg gcc tct ttg tgt ctg tca cag caa ttc aag gca caa    96
Leu Gly Met Gly Ala Ser Leu Cys Leu Ser Gln Gln Phe Lys Ala Gln
```

```
                     20                      25                       30
ggg gac tac ata ctg ggc ggg cta ttt ccc ctg ggc tca acc gag gag      144
Gly Asp Tyr Ile Leu Gly Gly Leu Phe Pro Leu Gly Ser Thr Glu Glu
        35                      40                      45 gcc act ctc aac cag aga aca caa ccc aac agc atc ccg tgc aac agg      192
Ala Thr Leu Asn Gln Arg Thr Gln Pro Asn Ser Ile Pro Cys Asn Arg
 50                      55                      60 ttc tca ccc ctt ggt ttg ttc ctg gcc atg gct atg aag atg gct gtg      240
Phe Ser Pro Leu Gly Leu Phe Leu Ala Met Ala Met Lys Met Ala Val
 65                      70                      75                  80 gag gag atc aac aat gga tct gcc ttg ctc cct ggg ctg cgg ctg ggc      288
Glu Glu Ile Asn Asn Gly Ser Ala Leu Leu Pro Gly Leu Arg Leu Gly
                 85                      90                      95 tat gac cta ttt gac aca tgc tcc gag cca gtg gtc acc atg aaa tcc      336
Tyr Asp Leu Phe Asp Thr Cys Ser Glu Pro Val Val Thr Met Lys Ser
            100                     105                     110 agt ctc atg ttc ctg gcc aag gtg ggc agt caa agc att gct gcc tac      384
Ser Leu Met Phe Leu Ala Lys Val Gly Ser Gln Ser Ile Ala Ala Tyr
        115                     120                     125 tgc aac tac aca cag tac caa ccc cgt gtg ctg gct gtc atc ggc ccc      432
Cys Asn Tyr Thr Gln Tyr Gln Pro Arg Val Leu Ala Val Ile Gly Pro
130                     135                     140 cac tca tca gag ctt gcc ctc att aca ggc aag ttc ttc agc ttc ttc      480
His Ser Ser Glu Leu Ala Leu Ile Thr Gly Lys Phe Phe Ser Phe Phe
145                     150                     155                 160 ctc atg cca cag gtc agc tat agt gcc agc atg gat cgg cta agt gac      528
Leu Met Pro Gln Val Ser Tyr Ser Ala Ser Met Asp Arg Leu Ser Asp
                165                     170                     175 cgg gaa acg ttt cca tcc ttc ttc cgc aca gtg ccc agt gac cgg gtg      576
Arg Glu Thr Phe Pro Ser Phe Phe Arg Thr Val Pro Ser Asp Arg Val
            180                     185                     190 cag ctg cag gca gtt gtg act ctg ttg cag aac ttc agc tgg aac tgg      624
Gln Leu Gln Ala Val Val Thr Leu Leu Gln Asn Phe Ser Trp Asn Trp
        195                     200                     205 gtg gcc gcc tta ggg agt gat gat gac tat ggc cgg gaa ggt ctg agc      672
Val Ala Ala Leu Gly Ser Asp Asp Asp Tyr Gly Arg Glu Gly Leu Ser
210                     215                     220 atc ttt tct agt ctg gcc aat gca cga ggt atc tgc atc gca cat gag      720
Ile Phe Ser Ser Leu Ala Asn Ala Arg Gly Ile Cys Ile Ala His Glu
225                     230                     235                 240 ggc ctg gtg cca caa cat gac act agt ggc caa cag ttg ggc aag gtg      768
Gly Leu Val Pro Gln His Asp Thr Ser Gly Gln Gln Leu Gly Lys Val
                245                     250                     255 ctg gat gta cta cgc caa gtg aac caa agt aaa gta caa gtg gtg gtg      816
Leu Asp Val Leu Arg Gln Val Asn Gln Ser Lys Val Gln Val Val Val
            260                     265                     270 ctg ttt gcc tct gcc cgt gct gtc tac tcc ctt ttt agt tac agc atc      864
Leu Phe Ala Ser Ala Arg Ala Val Tyr Ser Leu Phe Ser Tyr Ser Ile
        275                     280                     285 cat cat ggc ctc tca ccc aag gta tgg gtg gcc agt gag tct tgg ctg      912
His His Gly Leu Ser Pro Lys Val Trp Val Ala Ser Glu Ser Trp Leu
290                     295                     300 aca tct gac ctg gtc atg aca ctt ccc aat att gcc cgt gtg ggc act      960
Thr Ser Asp Leu Val Met Thr Leu Pro Asn Ile Ala Arg Val Gly Thr
305                     310                     315                 320 gtg ctt ggg ttt ttg cag cgg ggt gcc cta ctg cct gaa ttt tcc cat     1008
Val Leu Gly Phe Leu Gln Arg Gly Ala Leu Leu Pro Glu Phe Ser His
                325                     330                     335 tat gtg gag act cac ctt gcc ctg gcc gct gac cca gca ttc tgt gcc     1056
```

```
                Tyr Val Glu Thr His Leu Ala Leu Ala Ala Asp Pro Ala Phe Cys Ala
                            340                 345                 350 tca ctg aat gcg gag ttg gat ctg gag gaa cat gtg atg ggg caa cgc          1104
Ser Leu Asn Ala Glu Leu Asp Leu Glu Glu His Val Met Gly Gln Arg
            355                 360                 365 tgt cca cgg tgt gac gac atc atg ctg cag aac cta tca tct ggg ctg          1152
Cys Pro Arg Cys Asp Asp Ile Met Leu Gln Asn Leu Ser Ser Gly Leu
370                 375                 380 ttg cag aac cta tca gct ggg caa ttg cac cac caa ata ttt gca acc          1200
Leu Gln Asn Leu Ser Ala Gly Gln Leu His His Gln Ile Phe Ala Thr
385                 390                 395                 400 tat gca gct gtg tac agt gtg gct caa gcc ctt cac aac acc cta cag          1248
Tyr Ala Ala Val Tyr Ser Val Ala Gln Ala Leu His Asn Thr Leu Gln
                405                 410                 415 tgc aat gtc tca cat tgc cac gta tca gaa cat gtt cta ccc tgg cag          1296
Cys Asn Val Ser His Cys His Val Ser Glu His Val Leu Pro Trp Gln
            420                 425                 430 ctc ctg gag aac atg tac aat atg agt ttc cat gct cga gac ttg aca          1344
Leu Leu Glu Asn Met Tyr Asn Met Ser Phe His Ala Arg Asp Leu Thr
            435                 440                 445 cta cag ttt gat gct gaa ggg aat gta gac atg gaa tat gac ctg aag          1392
Leu Gln Phe Asp Ala Glu Gly Asn Val Asp Met Glu Tyr Asp Leu Lys
450                 455                 460 atg tgg gtg tgg cag agc cct aca cct gta tta cat act gtg ggc acc          1440
Met Trp Val Trp Gln Ser Pro Thr Pro Val Leu His Thr Val Gly Thr
465                 470                 475                 480 ttc aac ggc acc ctt cag ctg cag cag tct aaa atg tac tgg cca ggc          1488
Phe Asn Gly Thr Leu Gln Leu Gln Gln Ser Lys Met Tyr Trp Pro Gly
                485                 490                 495 aac cag gtg cca gtc tcc cag tgt tcc cgc cag tgc aaa gat ggc cag          1536
Asn Gln Val Pro Val Ser Gln Cys Ser Arg Gln Cys Lys Asp Gly Gln
            500                 505                 510 gtt cgc cga gta aag ggc ttt cat tcc tgc tgc tat gac tgc gtg gac          1584
Val Arg Arg Val Lys Gly Phe His Ser Cys Cys Tyr Asp Cys Val Asp
            515                 520                 525 tgc aag gcg ggc agc tac cgg aag cat cca gat gac ttc acc tgt act          1632
Cys Lys Ala Gly Ser Tyr Arg Lys His Pro Asp Asp Phe Thr Cys Thr
530                 535                 540 cca tgt aac cag gac cag tgg tcc cca gag aaa agc aca gcc tgc tta          1680
Pro Cys Asn Gln Asp Gln Trp Ser Pro Glu Lys Ser Thr Ala Cys Leu
545                 550                 555                 560 cct cgc agg ccc aag ttt ctg gct tgg ggg gag cca gtt gtg ctg tca          1728
Pro Arg Arg Pro Lys Phe Leu Ala Trp Gly Glu Pro Val Val Leu Ser
                565                 570                 575 ctc ctc ctg ctg ctt tgc ctg gtg ctg ggt cta gca ctg gct gct ctg          1776
Leu Leu Leu Leu Leu Cys Leu Val Leu Gly Leu Ala Leu Ala Ala Leu
            580                 585                 590 ggg ctc tct gtc cac cac tgg gac agc cct ctt gtc cag gcc tca ggt          1824
Gly Leu Ser Val His His Trp Asp Ser Pro Leu Val Gln Ala Ser Gly
            595                 600                 605 ggc tca cag ttc tgc ttt ggc ctg atc tgc cta ggc ctc ttc tgc ctc          1872
Gly Ser Gln Phe Cys Phe Gly Leu Ile Cys Leu Gly Leu Phe Cys Leu
610                 615                 620 agt gtc ctt ctg ttc cca ggg cgg cca agc tct gcc agc tgc ctt gca          1920
Ser Val Leu Leu Phe Pro Gly Arg Pro Ser Ser Ala Ser Cys Leu Ala
625                 630                 635                 640 caa caa cca atg gct cac ctc cct ctc aca ggc tgc ctg agc aca ctc          1968
Gln Gln Pro Met Ala His Leu Pro Leu Thr Gly Cys Leu Ser Thr Leu
                645                 650                 655
```

| | | |
|---|---|---|
| ttc ctg caa gca gct gag acc ttt gtg gag tct gag ctg cca ctg agc<br>Phe Leu Gln Ala Ala Glu Thr Phe Val Glu Ser Glu Leu Pro Leu Ser<br>660 665 670 | | 2016 |
| tgg gca aac tgg cta tgc agc tac ctt cgg gga ctc tgg gcc tgg cta<br>Trp Ala Asn Trp Leu Cys Ser Tyr Leu Arg Gly Leu Trp Ala Trp Leu<br>675 680 685 | | 2064 |
| gtg gta ctg ttg gcc act ttt gtg gag gca gca cta tgt gcc tgg tat<br>Val Val Leu Leu Ala Thr Phe Val Glu Ala Ala Leu Cys Ala Trp Tyr<br>690 695 700 | | 2112 |
| ttg atc gct ttc cca cca gag gtg gta aca gac tgg tca gtg ctg ccc<br>Leu Ile Ala Phe Pro Pro Glu Val Val Thr Asp Trp Ser Val Leu Pro<br>705 710 715 720 | | 2160 |
| aca gag gta ctg gag cac tgc cac gtg cgt tcc tgg gtc agc ctg ggc<br>Thr Glu Val Leu Glu His Cys His Val Arg Ser Trp Val Ser Leu Gly<br>725 730 735 | | 2208 |
| ttg gtg cac atc acc aat gca atg tta gct ttc ctc tgc ttt ctg ggc<br>Leu Val His Ile Thr Asn Ala Met Leu Ala Phe Leu Cys Phe Leu Gly<br>740 745 750 | | 2256 |
| act ttc ctg gta cag agc cag cct ggc cgc tac aac cgt gcc cgt ggt<br>Thr Phe Leu Val Gln Ser Gln Pro Gly Arg Tyr Asn Arg Ala Arg Gly<br>755 760 765 | | 2304 |
| ctc acc ttc gcc atg cta gct tat ttc atc acc tgg gtc tct ttt gtg<br>Leu Thr Phe Ala Met Leu Ala Tyr Phe Ile Thr Trp Val Ser Phe Val<br>770 775 780 | | 2352 |
| ccc ctc ctg gcc aat gtg cag gtg gcc tac cag cca gct gtg cag atg<br>Pro Leu Leu Ala Asn Val Gln Val Ala Tyr Gln Pro Ala Val Gln Met<br>785 790 795 800 | | 2400 |
| ggt gct atc cta gtc tgt gcc ctg ggc atc ctg gtc acc ttc cac ctg<br>Gly Ala Ile Leu Val Cys Ala Leu Gly Ile Leu Val Thr Phe His Leu<br>805 810 815 | | 2448 |
| ccc aag tgc tat gtg ctt ctt tgg ctg cca aag ctc aac acc cag gag<br>Pro Lys Cys Tyr Val Leu Leu Trp Leu Pro Lys Leu Asn Thr Gln Glu<br>820 825 830 | | 2496 |
| ttc ttc ctg gga agg aat gcc aag aaa gca gca gat gag aac agt ggc<br>Phe Phe Leu Gly Arg Asn Ala Lys Lys Ala Ala Asp Glu Asn Ser Gly<br>835 840 845 | | 2544 |
| ggt ggt gag gca gct cag gga cac aat gaa tga<br>Gly Gly Glu Ala Ala Gln Gly His Asn Glu<br>850 855 | | 2577 |

<210> SEQ ID NO 58
<211> LENGTH: 858
<212> TYPE: PRT
<213> ORGANISM: Mus musculus

<400> SEQUENCE: 58

Met Pro Ala Leu Ala Ile Met Gly Leu Ser Leu Ala Ala Phe Leu Glu
1               5                   10                  15

Leu Gly Met Gly Ala Ser Leu Cys Leu Ser Gln Gln Phe Lys Ala Gln
                20                  25                  30

Gly Asp Tyr Ile Leu Gly Gly Leu Phe Pro Leu Gly Ser Thr Glu Glu
            35                  40                  45

Ala Thr Leu Asn Gln Arg Thr Gln Pro Asn Ser Ile Pro Cys Asn Arg
        50                  55                  60

Phe Ser Pro Leu Gly Leu Phe Leu Ala Met Ala Met Lys Met Ala Val
65                  70                  75                  80

Glu Glu Ile Asn Asn Gly Ser Ala Leu Leu Pro Gly Leu Arg Leu Gly
                85                  90                  95

Tyr Asp Leu Phe Asp Thr Cys Ser Glu Pro Val Val Thr Met Lys Ser

```
                100                 105                 110
Ser Leu Met Phe Leu Ala Lys Val Gly Ser Gln Ser Ile Ala Ala Tyr
            115                 120                 125
Cys Asn Tyr Thr Gln Tyr Gln Pro Arg Val Leu Ala Val Ile Gly Pro
            130                 135                 140
His Ser Ser Glu Leu Ala Leu Ile Thr Gly Lys Phe Phe Ser Phe Phe
145                 150                 155                 160
Leu Met Pro Gln Val Ser Tyr Ser Ala Ser Met Asp Arg Leu Ser Asp
                165                 170                 175
Arg Glu Thr Phe Pro Ser Phe Phe Arg Thr Val Pro Ser Asp Arg Val
                180                 185                 190
Gln Leu Gln Ala Val Val Thr Leu Leu Gln Asn Phe Ser Trp Asn Trp
            195                 200                 205
Val Ala Ala Leu Gly Ser Asp Asp Tyr Gly Arg Glu Gly Leu Ser
            210                 215                 220
Ile Phe Ser Ser Leu Ala Asn Ala Arg Gly Ile Cys Ile Ala His Glu
225                 230                 235                 240
Gly Leu Val Pro Gln His Asp Thr Ser Gly Gln Gln Leu Gly Lys Val
                245                 250                 255
Leu Asp Val Leu Arg Gln Val Asn Gln Ser Lys Val Gln Val Val Val
                260                 265                 270
Leu Phe Ala Ser Ala Arg Ala Val Tyr Ser Leu Phe Ser Tyr Ser Ile
            275                 280                 285
His His Gly Leu Ser Pro Lys Val Trp Val Ala Ser Glu Ser Trp Leu
            290                 295                 300
Thr Ser Asp Leu Val Met Thr Leu Pro Asn Ile Ala Arg Val Gly Thr
305                 310                 315                 320
Val Leu Gly Phe Leu Gln Arg Gly Ala Leu Leu Pro Glu Phe Ser His
                325                 330                 335
Tyr Val Glu Thr His Leu Ala Leu Ala Ala Asp Pro Ala Phe Cys Ala
                340                 345                 350
Ser Leu Asn Ala Glu Leu Asp Leu Glu Glu His Val Met Gly Gln Arg
            355                 360                 365
Cys Pro Arg Cys Asp Asp Ile Met Leu Gln Asn Leu Ser Ser Gly Leu
            370                 375                 380
Leu Gln Asn Leu Ser Ala Gly Gln Leu His His Gln Ile Phe Ala Thr
385                 390                 395                 400
Tyr Ala Ala Val Tyr Ser Val Ala Gln Ala Leu His Asn Thr Leu Gln
                405                 410                 415
Cys Asn Val Ser His Cys His Val Ser Glu His Val Leu Pro Trp Gln
                420                 425                 430
Leu Leu Glu Asn Met Tyr Asn Met Ser Phe His Ala Arg Asp Leu Thr
            435                 440                 445
Leu Gln Phe Asp Ala Glu Gly Asn Val Asp Met Glu Tyr Asp Leu Lys
            450                 455                 460
Met Trp Val Trp Gln Ser Pro Thr Pro Val Leu His Thr Val Gly Thr
465                 470                 475                 480
Phe Asn Gly Thr Leu Gln Leu Gln Gln Ser Lys Met Tyr Trp Pro Gly
                485                 490                 495
Asn Gln Val Pro Val Ser Gln Cys Ser Arg Gln Cys Lys Asp Gly Gln
                500                 505                 510
Val Arg Arg Val Lys Gly Phe His Ser Cys Cys Tyr Asp Cys Val Asp
            515                 520                 525
```

```
Cys Lys Ala Gly Ser Tyr Arg Lys His Pro Asp Asp Phe Thr Cys Thr
            530                 535                 540

Pro Cys Asn Gln Asp Gln Trp Ser Pro Glu Lys Ser Thr Ala Cys Leu
545                 550                 555                 560

Pro Arg Arg Pro Lys Phe Leu Ala Trp Gly Glu Pro Val Val Leu Ser
                565                 570                 575

Leu Leu Leu Leu Leu Cys Leu Val Leu Gly Leu Ala Leu Ala Ala Leu
            580                 585                 590

Gly Leu Ser Val His His Trp Asp Ser Pro Leu Val Gln Ala Ser Gly
            595                 600                 605

Gly Ser Gln Phe Cys Phe Gly Leu Ile Cys Leu Gly Leu Phe Cys Leu
            610                 615                 620

Ser Val Leu Leu Phe Pro Gly Arg Pro Ser Ser Ala Ser Cys Leu Ala
625                 630                 635                 640

Gln Gln Pro Met Ala His Leu Pro Leu Thr Gly Cys Leu Ser Thr Leu
                645                 650                 655

Phe Leu Gln Ala Ala Glu Thr Phe Val Glu Ser Glu Leu Pro Leu Ser
            660                 665                 670

Trp Ala Asn Trp Leu Cys Ser Tyr Leu Arg Gly Leu Trp Ala Trp Leu
            675                 680                 685

Val Val Leu Leu Ala Thr Phe Val Glu Ala Ala Leu Cys Ala Trp Tyr
690                 695                 700

Leu Ile Ala Phe Pro Pro Glu Val Val Thr Asp Trp Ser Val Leu Pro
705                 710                 715                 720

Thr Glu Val Leu Glu His Cys His Val Arg Ser Trp Val Ser Leu Gly
                725                 730                 735

Leu Val His Ile Thr Asn Ala Met Leu Ala Phe Leu Cys Phe Leu Gly
            740                 745                 750

Thr Phe Leu Val Gln Ser Gln Pro Gly Arg Tyr Asn Arg Ala Arg Gly
            755                 760                 765

Leu Thr Phe Ala Met Leu Ala Tyr Phe Ile Thr Trp Val Ser Phe Val
770                 775                 780

Pro Leu Leu Ala Asn Val Gln Val Ala Tyr Gln Pro Ala Val Gln Met
785                 790                 795                 800

Gly Ala Ile Leu Val Cys Ala Leu Gly Ile Leu Val Thr Phe His Leu
                805                 810                 815

Pro Lys Cys Tyr Val Leu Leu Trp Leu Pro Lys Leu Asn Thr Gln Glu
            820                 825                 830

Phe Phe Leu Gly Arg Asn Ala Lys Ala Ala Asp Glu Asn Ser Gly
            835                 840                 845

Gly Gly Glu Ala Ala Gln Gly His Asn Glu
    850                 855

<210> SEQ ID NO 59
<211> LENGTH: 1125
<212> TYPE: DNA
<213> ORGANISM: Rattus norvegicus
<220> FEATURE:
<221> NAME/KEY: CDS
<222> LOCATION: (1)..(1125)

<400> SEQUENCE: 59 atg gcc cgg tcc ctg act tgg ggc tgc tgt ccc tgg tgc ctg acg gaa      48
Met Ala Arg Ser Leu Thr Trp Gly Cys Cys Pro Trp Cys Leu Thr Glu
1               5                   10                  15
```

| | | |
|---|---|---|
| gag gag aag act gcc gcc aga atc gac cag gag atc aac aag att ttg<br>Glu Glu Lys Thr Ala Ala Arg Ile Asp Gln Glu Ile Asn Lys Ile Leu<br>20 25 30 | | 96 |
| ttg gaa cag aag aaa caa gag cgc ggg gaa ttg aaa ctc ctg ctg ttg<br>Leu Glu Gln Lys Lys Gln Glu Arg Gly Glu Leu Lys Leu Leu Leu Leu<br>35 40 45 | | 144 |
| ggg ccc ggt gag agc ggg aaa agc acg ttc atc aag caa atg cgc atc<br>Gly Pro Gly Glu Ser Gly Lys Ser Thr Phe Ile Lys Gln Met Arg Ile<br>50 55 60 | | 192 |
| att cac ggc gcc ggc tac tct gag gag gac cgc aga gcc ttc cgg ctg<br>Ile His Gly Ala Gly Tyr Ser Glu Glu Asp Arg Arg Ala Phe Arg Leu<br>65 70 75 80 | | 240 |
| ctc gtc tac cag aac atc ttc gtc tcc atg cag gcc atg att gaa gca<br>Leu Val Tyr Gln Asn Ile Phe Val Ser Met Gln Ala Met Ile Glu Ala<br>85 90 95 | | 288 |
| atg gac agg ctg cag atc ccc ttc agc agg ccg gac agc aaa cag cac<br>Met Asp Arg Leu Gln Ile Pro Phe Ser Arg Pro Asp Ser Lys Gln His<br>100 105 110 | | 336 |
| gcc agc ctg gtg atg acc cag gac ccc tat aaa gtg agc tcg ttc gag<br>Ala Ser Leu Val Met Thr Gln Asp Pro Tyr Lys Val Ser Ser Phe Glu<br>115 120 125 | | 384 |
| aag cca tat gca gtg gcc atg cag tac ctg tgg cgg gac gcg ggc atc<br>Lys Pro Tyr Ala Val Ala Met Gln Tyr Leu Trp Arg Asp Ala Gly Ile<br>130 135 140 | | 432 |
| cgc gca tgc tac gag cgg agg cgt gaa ttc cac ctg ctg gac tcc gcg<br>Arg Ala Cys Tyr Glu Arg Arg Arg Glu Phe His Leu Leu Asp Ser Ala<br>145 150 155 160 | | 480 |
| gtg tac tac ctg tca cac ctg gag cgc atc gcc gag gac gac tac atc<br>Val Tyr Tyr Leu Ser His Leu Glu Arg Ile Ala Glu Asp Asp Tyr Ile<br>165 170 175 | | 528 |
| ccc act gcg cag gac gtg ctg cgc agt cgc atg ccc acc act ggc atc<br>Pro Thr Ala Gln Asp Val Leu Arg Ser Arg Met Pro Thr Thr Gly Ile<br>180 185 190 | | 576 |
| aat gag tac tgc ttt tcc gtg cag aaa acc aaa ctg cgc atc gtg gat<br>Asn Glu Tyr Cys Phe Ser Val Gln Lys Thr Lys Leu Arg Ile Val Asp<br>195 200 205 | | 624 |
| gct ggc ggc cag aag tca gaa cgt aag aaa tgg atc cac tgt ttc gag<br>Ala Gly Gly Gln Lys Ser Glu Arg Lys Lys Trp Ile His Cys Phe Glu<br>210 215 220 | | 672 |
| aac gtg att gcc ctc atc tac ctg gcg tct ctg agc gag tat gac cag<br>Asn Val Ile Ala Leu Ile Tyr Leu Ala Ser Leu Ser Glu Tyr Asp Gln<br>225 230 235 240 | | 720 |
| tgt ctg gag gag aac agt cag gag aac cgt atg aag gag agt ctc gct<br>Cys Leu Glu Glu Asn Ser Gln Glu Asn Arg Met Lys Glu Ser Leu Ala<br>245 250 255 | | 768 |
| ctg ttt agc acg atc cta gag ctg ccc tgg ttc aag agc acc tcg gtc<br>Leu Phe Ser Thr Ile Leu Glu Leu Pro Trp Phe Lys Ser Thr Ser Val<br>260 265 270 | | 816 |
| atc ctc ttc ctc aac aag aca gac atc ctg gag gat aaa atc cac acc<br>Ile Leu Phe Leu Asn Lys Thr Asp Ile Leu Glu Asp Lys Ile His Thr<br>275 280 285 | | 864 |
| tcc cac cta gcc tca tac ttc ccc agc ttc cag gga ccc cgg agg gac<br>Ser His Leu Ala Ser Tyr Phe Pro Ser Phe Gln Gly Pro Arg Arg Asp<br>290 295 300 | | 912 |
| gca gag gcc gcc aag cgc ttc atc ttg gac atg tac gcg cgc gtg tac<br>Ala Glu Ala Ala Lys Arg Phe Ile Leu Asp Met Tyr Ala Arg Val Tyr<br>305 310 315 320 | | 960 |
| gcg agc tgt gca gag ccc cac gac ggt ggc agg aag gga tcc cgc gcg<br>Ala Ser Cys Ala Glu Pro His Asp Gly Gly Arg Lys Gly Ser Arg Ala<br>325 330 335 | | 1008 |

```
cgc cgc ctc ttc gca cac ttc acc tgt gcc acg gac acg cac agc gtc    1056
Arg Arg Leu Phe Ala His Phe Thr Cys Ala Thr Asp Thr His Ser Val
        340                 345                 350 cgc agc gtg ttc aag gac gtg cgg gac tca gtg ctg gcc cgg tac ctg    1104
Arg Ser Val Phe Lys Asp Val Arg Asp Ser Val Leu Ala Arg Tyr Leu
        355                 360                 365 gac gag atc aac ctg ttg tga                                        1125
Asp Glu Ile Asn Leu Leu
        370

<210> SEQ ID NO 60
<211> LENGTH: 374
<212> TYPE: PRT
<213> ORGANISM: Rattus norvegicus

<400> SEQUENCE: 60

Met Ala Arg Ser Leu Thr Trp Gly Cys Cys Pro Trp Cys Leu Thr Glu
1               5                   10                  15

Glu Glu Lys Thr Ala Ala Arg Ile Asp Gln Glu Ile Asn Lys Ile Leu
            20                  25                  30

Leu Glu Gln Lys Lys Gln Glu Arg Gly Glu Leu Lys Leu Leu Leu Leu
        35                  40                  45

Gly Pro Gly Glu Ser Gly Lys Ser Thr Phe Ile Lys Gln Met Arg Ile
    50                  55                  60

Ile His Gly Ala Gly Tyr Ser Glu Glu Asp Arg Ala Phe Arg Leu
65                  70                  75                  80

Leu Val Tyr Gln Asn Ile Phe Val Ser Met Gln Ala Met Ile Glu Ala
                85                  90                  95

Met Asp Arg Leu Gln Ile Pro Phe Ser Arg Pro Asp Ser Lys Gln His
            100                 105                 110

Ala Ser Leu Val Met Thr Gln Asp Pro Tyr Lys Val Ser Ser Phe Glu
        115                 120                 125

Lys Pro Tyr Ala Val Ala Met Gln Tyr Leu Trp Arg Asp Ala Gly Ile
    130                 135                 140

Arg Ala Cys Tyr Glu Arg Arg Glu Phe His Leu Leu Asp Ser Ala
145                 150                 155                 160

Val Tyr Tyr Leu Ser His Leu Glu Arg Ile Ala Glu Asp Asp Tyr Ile
                165                 170                 175

Pro Thr Ala Gln Asp Val Leu Arg Ser Arg Met Pro Thr Thr Gly Ile
            180                 185                 190

Asn Glu Tyr Cys Phe Ser Val Gln Lys Thr Lys Leu Arg Ile Val Asp
        195                 200                 205

Ala Gly Gly Gln Lys Ser Glu Arg Lys Lys Trp Ile His Cys Phe Glu
    210                 215                 220

Asn Val Ile Ala Leu Ile Tyr Leu Ala Ser Leu Ser Glu Tyr Asp Gln
225                 230                 235                 240

Cys Leu Glu Glu Asn Ser Gln Glu Asn Arg Met Lys Glu Ser Leu Ala
                245                 250                 255

Leu Phe Ser Thr Ile Leu Glu Leu Pro Trp Phe Lys Ser Thr Ser Val
            260                 265                 270

Ile Leu Phe Leu Asn Lys Thr Asp Ile Leu Glu Asp Lys Ile His Thr
        275                 280                 285

Ser His Leu Ala Ser Tyr Phe Pro Ser Phe Gln Gly Pro Arg Arg Asp
    290                 295                 300

Ala Glu Ala Ala Lys Arg Phe Ile Leu Asp Met Tyr Ala Arg Val Tyr
```

```
                305                 310                 315                 320
Ala Ser Cys Ala Glu Pro His Asp Gly Gly Arg Lys Gly Ser Arg Ala
                325                 330                 335

Arg Arg Leu Phe Ala His Phe Thr Cys Ala Thr Asp Thr His Ser Val
                340                 345                 350

Arg Ser Val Phe Lys Asp Val Arg Asp Ser Val Leu Ala Arg Tyr Leu
                355                 360                 365

Asp Glu Ile Asn Leu Leu
                370

<210> SEQ ID NO 61
<211> LENGTH: 1065
<212> TYPE: DNA
<213> ORGANISM: Rattus norvegicus
<220> FEATURE:
<221> NAME/KEY: CDS
<222> LOCATION: (1)..(1065)

<400> SEQUENCE: 61 atg ggg agt ggc atc agt gct gag gac aaa gaa ctt gcc aag agg tcc      48
Met Gly Ser Gly Ile Ser Ala Glu Asp Lys Glu Leu Ala Lys Arg Ser
1               5                   10                  15 agg gag ctg gaa aag aag ctg cag gag gat gct gac aag gaa gcc aag      96
Arg Glu Leu Glu Lys Lys Leu Gln Glu Asp Ala Asp Lys Glu Ala Lys
                20                  25                  30 act gtc aag ctg ctg ctg ctt ggt gcg gga gag tca ggg aag agc acg     144
Thr Val Lys Leu Leu Leu Leu Gly Ala Gly Glu Ser Gly Lys Ser Thr
            35                  40                  45 atc gtc aaa caa atg aag atc att cac cag gat ggc tac tca ccc gaa     192
Ile Val Lys Gln Met Lys Ile Ile His Gln Asp Gly Tyr Ser Pro Glu
        50                  55                  60 gaa tgc cta gaa ttc aaa tct gtc atc tat ggg aac gtg ttg cag tcc     240
Glu Cys Leu Glu Phe Lys Ser Val Ile Tyr Gly Asn Val Leu Gln Ser
65                  70                  75                  80 atc ctg gct atc atc aga gcc atg tcc aca cta ggc att gac tat gct     288
Ile Leu Ala Ile Ile Arg Ala Met Ser Thr Leu Gly Ile Asp Tyr Ala
                85                  90                  95 gaa cca agc tgt gcg gaa gcg ggg aga cag ctc aac aac ctg gct gac     336
Glu Pro Ser Cys Ala Glu Ala Gly Arg Gln Leu Asn Asn Leu Ala Asp
                100                 105                 110 tcc acc gag gag ggg acc atg cct tcc gag ctg gtg gag gtc atc aga     384
Ser Thr Glu Glu Gly Thr Met Pro Ser Glu Leu Val Glu Val Ile Arg
            115                 120                 125 aag ttg tgg aag gac ggt gga gtt caa gcc tgc ttt gac aga gcc gca     432
Lys Leu Trp Lys Asp Gly Gly Val Gln Ala Cys Phe Asp Arg Ala Ala
        130                 135                 140 gag ttc cag ctc aat gac tcg gca tct tat tac ctg aac cag ctg gac     480
Glu Phe Gln Leu Asn Asp Ser Ala Ser Tyr Tyr Leu Asn Gln Leu Asp
145                 150                 155                 160 cgg att aca gac cct gac tac ctc cct aat gag caa gac gtg ctt cga     528
Arg Ile Thr Asp Pro Asp Tyr Leu Pro Asn Glu Gln Asp Val Leu Arg
                165                 170                 175 tcc aga gtc aag aca aca ggc atc atc gag acc aag ttt tct gta aaa     576
Ser Arg Val Lys Thr Thr Gly Ile Ile Glu Thr Lys Phe Ser Val Lys
                180                 185                 190 gat ttg aat ttt agg atg ttt gac gtg gga ggg cag aga tca gag agg     624
Asp Leu Asn Phe Arg Met Phe Asp Val Gly Gly Gln Arg Ser Glu Arg
            195                 200                 205 aag aaa tgg atc cac tgc ttt gag gga gtc acc tgc atc att ttc tgt     672
Lys Lys Trp Ile His Cys Phe Glu Gly Val Thr Cys Ile Ile Phe Cys
```

```
gct gct ctt agc gcc tat gac atg gtg ctg gtg gag gat gac gag gtg      720
Ala Ala Leu Ser Ala Tyr Asp Met Val Leu Val Glu Asp Asp Glu Val
225                 230                 235                 240 aat cgc atg cat gag tct cta cat ctg ttc aac agc atc tgt aac cac      768
Asn Arg Met His Glu Ser Leu His Leu Phe Asn Ser Ile Cys Asn His
                245                 250                 255 aag ttc ttt gcg gct act tcc att gtt ctc ttt ctc aac aag aag gac      816
Lys Phe Phe Ala Ala Thr Ser Ile Val Leu Phe Leu Asn Lys Lys Asp
            260                 265                 270 ctc ttt gag gaa aaa att aag aaa gtc cac ctc agt atc tgt ttc ccg      864
Leu Phe Glu Glu Lys Ile Lys Lys Val His Leu Ser Ile Cys Phe Pro
        275                 280                 285 gag tat gac ggc aac aat tcc tat gag gat gcc ggg aat tac atc aag      912
Glu Tyr Asp Gly Asn Asn Ser Tyr Glu Asp Ala Gly Asn Tyr Ile Lys
    290                 295                 300 agt cag ttc ctt gac ctc aac atg agg aaa gat gtc aaa gag atc tac      960
Ser Gln Phe Leu Asp Leu Asn Met Arg Lys Asp Val Lys Glu Ile Tyr
305                 310                 315                 320 agc cac atg act tgt gct acg gac aca cag aac gtc aaa ttt gtg ttt     1008
Ser His Met Thr Cys Ala Thr Asp Thr Gln Asn Val Lys Phe Val Phe
                325                 330                 335 gat gca gtc aca gac att atc atc aag gaa aac ctc aag gac tgt ggg     1056
Asp Ala Val Thr Asp Ile Ile Ile Lys Glu Asn Leu Lys Asp Cys Gly
            340                 345                 350 ctc ttt taa                                                         1065
Leu Phe <210> SEQ ID NO 62
<211> LENGTH: 354
<212> TYPE: PRT
<213> ORGANISM: Rattus norvegicus

<400> SEQUENCE: 62

Met Gly Ser Gly Ile Ser Ala Glu Asp Lys Glu Leu Ala Lys Arg Ser
1               5                   10                  15

Arg Glu Leu Glu Lys Lys Leu Gln Glu Asp Ala Asp Lys Glu Ala Lys
            20                  25                  30

Thr Val Lys Leu Leu Leu Leu Gly Ala Gly Glu Ser Gly Lys Ser Thr
        35                  40                  45

Ile Val Lys Gln Met Lys Ile Ile His Gln Asp Gly Tyr Ser Pro Glu
    50                  55                  60

Glu Cys Leu Glu Phe Lys Ser Val Ile Tyr Gly Asn Val Leu Gln Ser
65                  70                  75                  80

Ile Leu Ala Ile Ile Arg Ala Met Ser Thr Leu Gly Ile Asp Tyr Ala
                85                  90                  95

Glu Pro Ser Cys Ala Glu Ala Gly Arg Gln Leu Asn Asn Leu Ala Asp
            100                 105                 110

Ser Thr Glu Glu Gly Thr Met Pro Ser Glu Leu Val Glu Val Ile Arg
        115                 120                 125

Lys Leu Trp Lys Asp Gly Gly Val Gln Ala Cys Phe Asp Arg Ala Ala
    130                 135                 140

Glu Phe Gln Leu Asn Asp Ser Ala Ser Tyr Tyr Leu Asn Gln Leu Asp
145                 150                 155                 160

Arg Ile Thr Asp Pro Asp Tyr Leu Pro Asn Glu Gln Asp Val Leu Arg
                165                 170                 175

Ser Arg Val Lys Thr Thr Gly Ile Ile Glu Thr Lys Phe Ser Val Lys
```

-continued

```
              180                 185                 190
Asp Leu Asn Phe Arg Met Phe Asp Val Gly Gly Gln Arg Ser Glu Arg
            195                 200                 205

Lys Lys Trp Ile His Cys Phe Glu Gly Val Thr Cys Ile Ile Phe Cys
        210                 215                 220

Ala Ala Leu Ser Ala Tyr Asp Met Val Leu Val Glu Asp Glu Val
225                 230                 235                 240

Asn Arg Met His Glu Ser Leu His Leu Phe Asn Ser Ile Cys Asn His
                245                 250                 255

Lys Phe Phe Ala Ala Thr Ser Ile Val Leu Phe Leu Asn Lys Lys Asp
                260                 265                 270

Leu Phe Glu Glu Lys Ile Lys Lys Val His Leu Ser Ile Cys Phe Pro
            275                 280                 285

Glu Tyr Asp Gly Asn Asn Ser Tyr Glu Asp Ala Gly Asn Tyr Ile Lys
        290                 295                 300

Ser Gln Phe Leu Asp Leu Asn Met Arg Lys Asp Val Lys Glu Ile Tyr
305                 310                 315                 320

Ser His Met Thr Cys Ala Thr Asp Thr Gln Asn Val Lys Phe Val Phe
                325                 330                 335

Asp Ala Val Thr Asp Ile Ile Ile Lys Glu Asn Leu Lys Asp Cys Gly
                340                 345                 350

Leu Phe
```